United States Patent
Miller et al.

(10) Patent No.: US 9,212,205 B2
(45) Date of Patent: Dec. 15, 2015

(54) NUCLEIC ACID BINDING COMPOUNDS AND METHODS OF USE

(75) Inventors: Benjamin L. Miller, Penfield, NY (US); Brian R. McNaughton, Rochester, NY (US); Peter C. Gareiss, Rochester, NY (US); Joseph Wedekind, Rochester, NY (US); Charles Thornton, Rochester, NY (US); Krzysztof Sobczak, Poznan (PL)

(73) Assignee: University of Rochester, Rochester, NY (US)

( * ) Notice: Subject to any disclaimer, the term of this patent is extended or adjusted under 35 U.S.C. 154(b) by 1126 days.

(21) Appl. No.: 12/670,772

(22) PCT Filed: Jul. 28, 2008

(86) PCT No.: PCT/US2008/071341
§ 371 (c)(1),
(2), (4) Date: Jun. 28, 2010

(87) PCT Pub. No.: WO2009/015384
PCT Pub. Date: Jan. 29, 2009

(65) Prior Publication Data
US 2010/0266677 A1 Oct. 21, 2010

Related U.S. Application Data

(60) Provisional application No. 60/952,104, filed on Jul. 26, 2007.

(51) Int. Cl.
| | | |
|---|---|---|
| *C07K 5/08* | (2006.01) | |
| *A61K 38/00* | (2006.01) | |
| *C07K 1/113* | (2006.01) | |
| *C07K 5/083* | (2006.01) | |
| *C07K 5/087* | (2006.01) | |
| *C07K 5/09* | (2006.01) | |
| *C07K 5/097* | (2006.01) | |
| *C07K 1/04* | (2006.01) | |

(52) U.S. Cl.
CPC ............ *C07K 5/0806* (2013.01); *C07K 5/081* (2013.01); *C07K 5/0812* (2013.01); *C07K 5/0815* (2013.01); *C07K 5/0821* (2013.01); *A61K 38/00* (2013.01); *C07K 1/047* (2013.01)

(58) Field of Classification Search
None
See application file for complete search history.

(56) References Cited

U.S. PATENT DOCUMENTS

| | | |
|---|---|---|
| 5,552,282 A | 9/1996 | Caskey et al. |
| 5,811,515 A | 9/1998 | Grubbs et al. |
| 5,958,379 A | 9/1999 | Regenold et al. |
| 2002/0127581 A1 | 9/2002 | Rajendran et al. |
| 2007/0032636 A1 | 2/2007 | Sakalian et al. |
| 2007/0123465 A1 | 5/2007 | Adermann et al. |

FOREIGN PATENT DOCUMENTS

| | | |
|---|---|---|
| WO | 9014422 A1 | 11/1990 |
| WO | 9311154 A1 | 6/1993 |
| WO | 2007018843 A2 | 2/2007 |

OTHER PUBLICATIONS

Grant & Hackh's Chemical Dictionary (5th Ed. 1987) at p. 148.*
McNaughton, Brian R. Resin-Bound Dynamic Combinatorial Chemistry. Organic Letters. 2006, 8(9), 1803-1806.*
Chayajarus et al. "Efficient Synthesis of Carbohydrate Thionolactones", Tetrahedron Letters 47:3517-3520 2006.
Xie et al. "Selection of TAR RNA-Binding Chameleon Peptides by Using a Retroviral Replication System," Journal of Virology 78(3):1456-1463 2004.
PCT International Search Report and Written Opinion for PCT/US2008/071341 Jul. 28, 2008.

* cited by examiner

*Primary Examiner* — Samantha Shterengarts
(74) *Attorney, Agent, or Firm* — LeClairRyan, a Professional Corporation

(57) ABSTRACT

The present invention relates to homo- and hetero-dimer compounds formed by a disulfide, sulfinyl thio, or olefin bond between two monomers. A method of making a homo- or hetero-dimer compound is also disclosed. The present invention also relates to monomer compounds capable of forming homo- or hetero-dimer compounds, as well as oligomers formed via linkage of one or more dimers. Also disclosed are methods of inhibiting the activity of target RNA molecules, particularly those having a secondary structure that include a stem or stem-loop formation. Dimer compounds capable of inhibiting the activity of an HIV-I RNA frameshifting stem-loop and a (CUG)n expanded repeat stem-loop are disclosed, as are methods of treating diseases associated with these target RNA molecules. The dimer compounds can also be used for selectively detecting presence of the target RNA molecule in a sample.

18 Claims, 20 Drawing Sheets

Top: Bead Number
Bottom: Bead Size

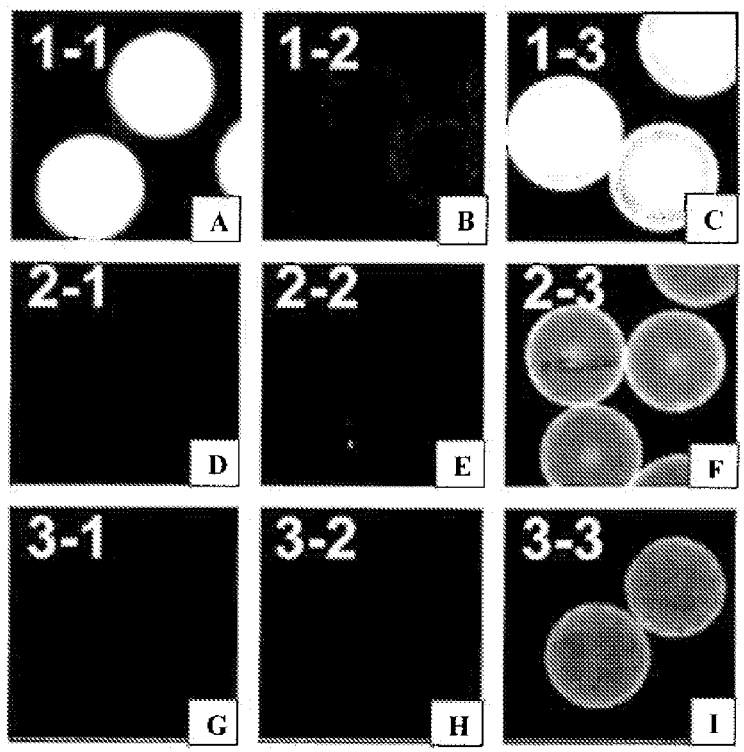
Figures 6A-I
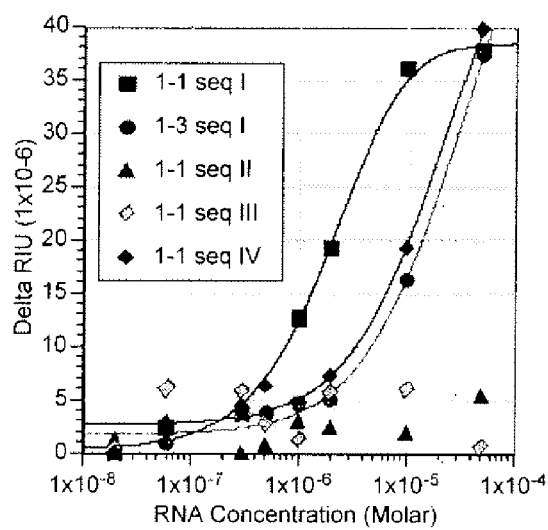
Figures 7A-E (Scheme 1)

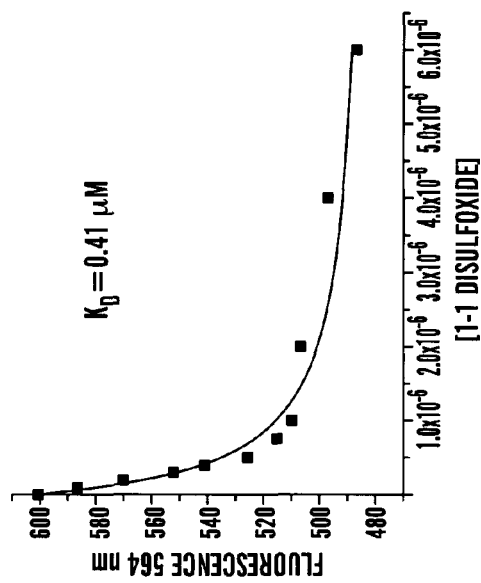
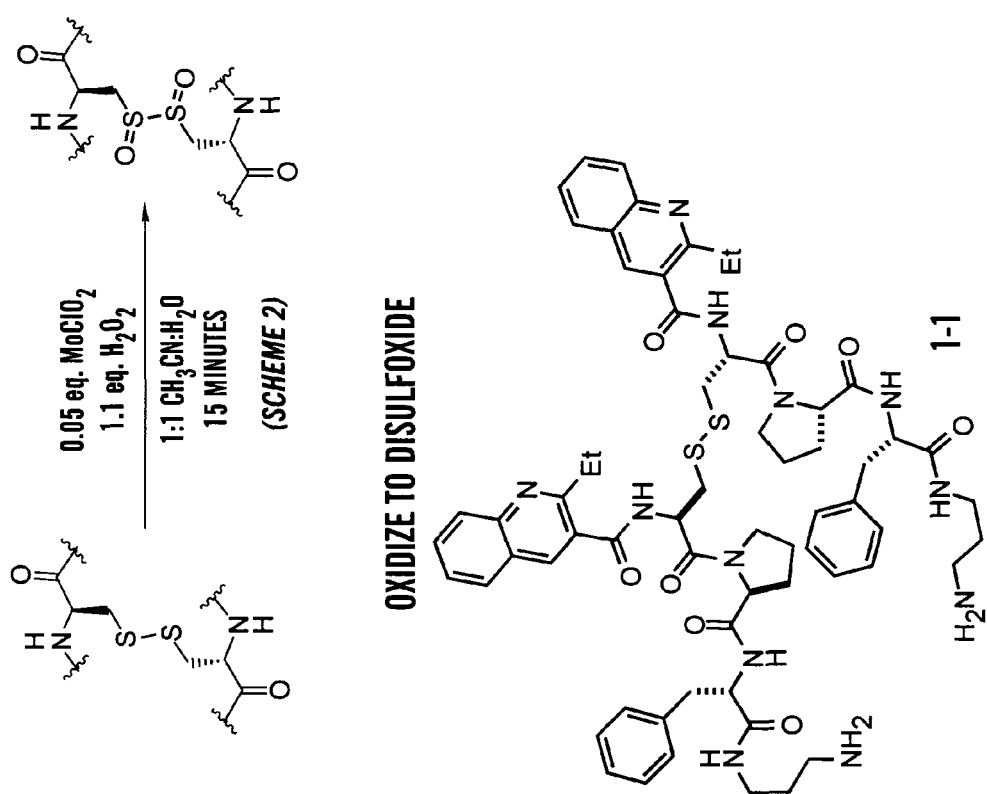
FIG. 13

NUCLEIC ACID BINDING COMPOUNDS AND METHODS OF USE

This application claims benefit of U.S. Provisional Patent Application Ser. No. 60/952,104, filed Jul. 26, 2007, which is hereby incorporated by reference in its entirety.

This invention was made with government support under grant number T32AR007472 awarded by the National Institutes of Health. The government has certain rights in the invention.

FIELD OF THE INVENTION

The present invention relates to nucleic acid binding compounds, libraries containing the same, and dimeric and oligomeric compounds formed by covalent binding of monomeric compounds. The use of the dimeric and oligomeric compounds to bind target nucleic acids and inhibit their activity is also described herein.

BACKGROUND OF THE INVENTION

Resin bound dynamic combinatorial chemistry ("RB-DCC") alleviates common problems associated with traditional solution phase dynamic combinatorial chemistry. In the RBDCC approach, immobilized library constituents are spatially segregated on a solid support and allowed to equilibrate with library constituents in solution via reversible bond formation. This solid phase immobilization thereby eliminates the need for chromatographic solution separation during dynamic combinatorial library ("DCL") analysis. Expanding on the utilization of phase separations in dynamic combinatorial chemistry (Klekota et al., "Generation of Novel DNA-binding Compounds by Selection and Amplification from Self-assembled Combinatorial Libraries," *Tetrahedron Letters* 38:8639-8642 (1997); Whitney et al., "Templated Ligand Assembly by Using G-quadruplex DNA and Dynamic Covalent Chemistry," *Angewandte Chemie International Edition English* 43:1143-1146 (2004), each of which is hereby incorporated by reference in its entirety), RBDCC represents the first example of phase tagging library members (McNaughton et al., "Resin-bound Dynamic Combinatorial Chemistry," *Organic Letters* 8:1803-1806 (2006), which is hereby incorporated by reference in its entirety). The RBDCC screening procedure utilizes a labeled target. When the library is screened against a fluorescently labeled target, any immobilized library member that binds the target is easily visualized, spatially separated, and identified by mass spectrometry, greatly simplifying DCL analysis.

The present invention is directed to the identification of compounds that are capable of modifying the activity of target RNA molecules associated with a particular disease state, and therefore also capable of treating those disease states.

SUMMARY OF THE INVENTION

A first aspect of the present invention relates to a homo- or hetero-dimer compound formed by a disulfide, sulfinyl thio, or olefin bond between two monomers having a structure

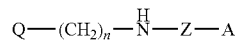

where, for each monomer (I),
Q is independently selected from H, $NH_2$,

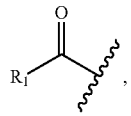

a cell uptake peptide moiety, and an inert substrate, where $R_1$ is selected from a straight or branched chain $C_1$ to $C_6$ hydrocarbon and an aromatic or heteroaromatic group;
n is independently an integer from 0 to about 5;
Z is independently a peptide containing at least two and up to about ten amino acids, where one of the amino acids is capable of forming a disulfide bond, sulfinyl thio linkage, or olefin bond; and
A is independently an aromatic or heteroaromatic group connected to Z via a carbonyl linkage.

A second aspect of the present invention relates to a method of inhibiting HIV-1 proliferation. This method involves providing a dimer compound according to the first aspect of the present invention and contacting an HIV-1 mRNA that encodes Pol polypeptide with the dimer compound under conditions effective to alter normal expression of the Pol polyprotein and thereby inhibit HIV-1 proliferation.

A third aspect of the present invention relates to a method of treating HIV-1 in a human patient. This method involves administering to a human patient a dimer compound according to the first aspect of the present invention under conditions effective to alter normal expression of HIV-1 Pol polyprotein, thereby disrupting HIV-1 proliferation to treat the human patient for HIV-1.

A fourth aspect of the present invention relates to a method of selecting homo- and/or hetero-dimer compounds capable of selectively binding an mRNA sequence containing a stem or stem/loop formation. This method involves providing a heterogeneous mixture of solution phase monomers each having a structure

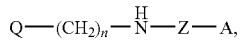

where, for each solution phase monomer,
Q is independently selected from H, $NH_2$, and

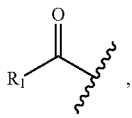

where $R_1$ is selected from a straight or branched chain $C_1$ to $C_6$ hydrocarbon and an aromatic or heteroaromatic group;
n is independently an integer from 0 to about 5;
Z is independently a peptide containing at least two and up to about ten amino acids, where one of the amino acids is capable of forming a disulfide bond, sulfinyl thio linkage, or olefin bond; and A is independently an aromatic or heteroaromatic group connected to Z via a carbonyl linkage.

The heterogeneous mixture of solution phase monomers is equilibrated with a labeled mRNA sequence and a heterogeneous mixture of inert substrate-bound monomers each having a structure

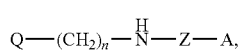  (I)

where, for each substrate-bound monomer, Q is an inert substrate and n, Z, and A are independently selected from the groups defined above. The equilibrating step is carried out under conditions effective to form homo- and/or hetero-dimers containing one solution phase monomer and one substrate-bound monomer. The labeled mRNA sequence is then detected, and the homo- and/or hetero-dimer compounds capable of selectively binding the mRNA sequence are selected based on said detecting.

A fifth aspect of the present invention relates to a method of altering the activity of a target RNA molecule. This method includes the step of contacting the RNA molecule with a dimer compound according to the first aspect of the present invention that selectively binds to the target RNA molecule, where the contacting is effective to alter activity of the RNA molecule. This approach can be used to treat or prevent any disease conditions that involve improper activity of the target RNA molecule as a result of a structural feature (e.g., stem or stem-loop formation) of the target RNA molecule.

A sixth aspect of the present invention is directed to a compound having a structure

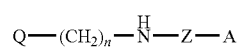  (I)

where
Q is selected from H, NH$_2$,

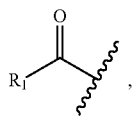, a cell uptake peptide moiety, and an inert substrate, where R$_1$ is selected from a straight or branched chain C$_1$ to C$_6$ hydrocarbon and an aromatic or heteroaromatic group;

n is an integer from 0 to about 5;

Z is a peptide containing at least two and up to about ten amino acids, where one of the amino acids is capable of forming a disulfide bond, sulfinyl thio linkage, or olefin bond; and A is an aromatic or heteroaromatic group connected to Z via a carbonyl linkage.

A seventh aspect of the present invention is directed to a composition containing a homo- or hetero-dimer compound according to the first aspect of the present invention and a carrier.

An eighth aspect of the present invention is directed to a method of detecting presence of an HIV-1 virus in a sample. This method involves providing a homo- or hetero-dimer compound according to the first aspect of the present invention, where the dimer compound is immobilized on a surface. The immobilized dimer compound is contacted with a sample under conditions effective to permit an mRNA frameshift regulatory molecule of the HIV-1 virus to bind specifically to the immobilized homo- or hetero-dimer compound. Presence of the mRNA frameshift regulatory molecule is detected in the sample based on the binding. Detection of the mRNA frameshift regulatory molecule indicates presence of the HIV-1 virus in the sample.

An ninth aspect of the present invention is directed to a method of making a homo- or hetero-dimer compound. This method involves providing a first and second monomer having a structure

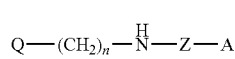  (I)

where
Q is selected from H, NH$_2$,

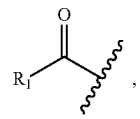, a cell uptake peptide moiety, and an inert substrate, where R$_1$ is selected from a straight or branched chain C$_1$ to C$_6$ hydrocarbon and an aromatic or heteroaromatic group;

n is an integer from 0 to about 5;

Z is a peptide containing at least two and up to about ten amino acids, where one of the amino acids is capable of forming a disulfide bond, sulfinyl thio linkage, or olefin bond; and A is an aromatic or heteroaromatic group connected to Z via a carbonyl linkage.

The first and second monomers are reacted under conditions effective to form a homo- or hetero-dimer compound as set forth in the first aspect of the present invention.

A tenth aspect of the present invention is directed to a method of treating a subject for a disorder caused by an expanded RNA repeat sequence. This method involves administering to the subject a dimer compound according to the first aspect of the present invention under conditions effective to alter function of an expanded RNA repeat sequence, thereby disrupting interaction between the RNA repeat sequence and splicing proteins to treat the subject for the disorder.

An eleventh aspect of the present invention is directed to an oligomer compound comprising two or more covalently linked homo- or hetero-dimer compounds according to the first aspect of the present invention. Use of the oligomers in each of the above-identified therapeutic methods of use is also contemplated.

As demonstrated by the accompanying Examples, a single library has afforded two distinct sets of selective nucleic acid binding compounds that are directed to two different RNA targets, the first an HIV-1 RNA stem/loop frameshift site associated with Gag/Pol expression and the second an RNA CUG$_{(n)}$ repeat associated with a form of muscular dystrophy (and representative of RNA repeats generally). Because these compounds have demonstrated success in inhibiting the activity of the target nucleic acid molecules, these compounds or derivatives thereof should provide effective therapy of the diseases associated with these RNA molecules.

These compounds can be used in combination with other known or hereafter developed therapies for these same diseases. Moreover, the libraries encompassed by the present invention should provide a rich resource to identify other compounds capable of binding other target nucleic acid molecules that are associated with particular disease states. For example, ribosomal frameshifting RNA elements are found in a variety of diseases including SARS-CoV (Brierley et al., "Programmed Ribosomal Frameshifting in HIV-1 and SARS-CoV," *Virus Research* 119:29-42 (2006), which is hereby incorporated by reference in its entirety), Hepatitis (Xu et al., "Synthesis of a Novel Hepatitis C Virus Protein by Ribosomal Frameshift," *EMBO* 20:3840-3848 (2001), which is hereby incorporated by reference in its entirety), Rous Sarcoma Virus (Jacks et al., "Signals for the Ribosomal Frameshifting in the Rous Sarcoma Virus Gag-Pol Region," *Cell* 55:447-458 (1998), which is hereby incorporated by reference in its entirety), Human T-Cell Leukemia Virus Type II (Kollmus et al., "The Sequences of and Distance Between Two Cis-Acting Signals Determine the Efficiency of Ribosomal Frameshifting in Human Immunodeficiency Virus Type I and Human T-cell Leukemia Virus Type II in vivo," *J. Virol.* 68:6087-6091 (1994), which is hereby incorporated by reference in its entirety), and Coronavirus (Brierley et al., "Characterization of an Efficient Coronavirus Ribosomal Frameshifting Signal: Requirement for an RNA Psuedoknot," *Cell* 57:537-547 (1989), which is hereby incorporated by reference in its entirety).

BRIEF DESCRIPTION OF THE DRAWINGS

FIG. 1B is a schematic illustration showing the solid phase monomer compounds (left side), and their combination with solution phase monomers to form the 11,325 member library.

FIGS. 6A-I are images illustrating determination of the highest-affinity ligands among dimer pairs of library monomer building blocks identified following the initial screen with the HIV-1 frame shifting RNA stem-loop. The coding scheme x-y represents the following: x=resin-bound component, y=solution phase component. Specifically, FIG. 6A is a dimer compound formed from two monomers 1 (dimer 1-1), FIG. 6B is a dimer compound formed from monomer 1 and monomer 2 (dimer 1-2), FIG. 6C is a dimer compound formed from monomer 1 and monomer 3 (dimer 1-3), FIG. 6D is a dimer compound formed from monomer 2 and monomer 1 (dimer 2-1), FIG. 6E is a dimer compound formed from two monomers 2 (dimer 2-2), FIG. 6F is a dimer compound formed from monomer 2 and monomer 3 (dimer 2-3), FIG. 6G is a dimer compound formed from monomer 3 and monomer 1 (dimer 3-1), FIG. 6H is a dimer compound formed from monomer 3 and monomer 2 (dimer 3-2), and FIG. 6I is a dimer compound formed from two monomers 3 (dimer 3-3). Degree of fluorescence indicates the amount of fluorescently labeled HIV-1 RNA stem-loop bound.

FIGS. 7A-E show surface plasmon resonance ("SPR") binding isotherms (FIG. 7A) for selected dimer compounds to the HIV-1 frameshift regulatory RNA sequence (SEQ ID NO:1) (FIG. 7B), a DNA sequence homologous to the HIV-1 frameshift regulatory RNA sequence (SEQ ID NO:2) (FIG. 7C), an alternate RNA stem-loop sequence (SEQ ID NO:3) (FIG. 7D), and an RNA stem loop with an altered loop sequence (SEQ ID NO:4) (FIG. 7E).

FIG. 13 illustrates Scheme 2 for the formation of disulfoxide analogs of the library disulfide dimers.

FIG. 15A illustrates the assembly of filters for filter binding assay, and the corresponding raw filter images of binding analysis of compound 8-8 and SEQ ID NO:8 (bottom left). FIG. 15B is a graph of binding curves of the 10 possible selected disulfide RBDCL ligands for SEQ ID NO:8, the FAM-CUG$_{(109)}$ repeat RNA.

DETAILED DESCRIPTION OF THE INVENTION

Figure 1A:
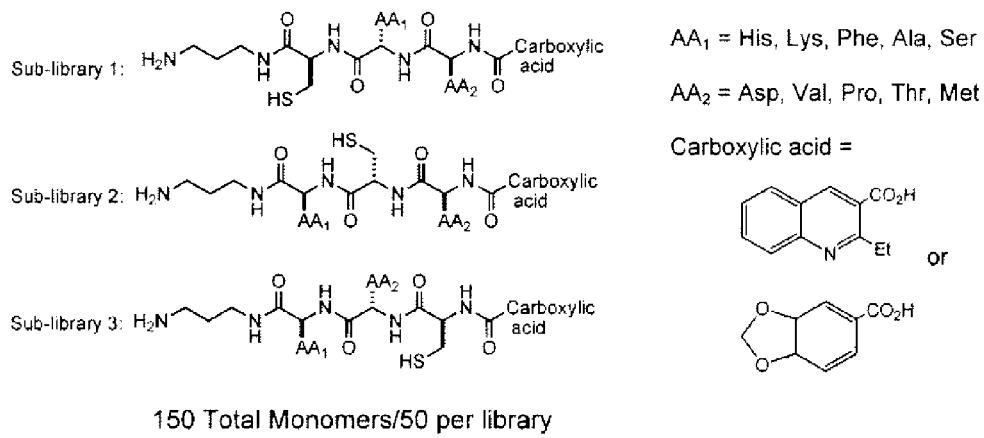
FIGS. 1A-B are illustrations of the solution phase monomer compounds (1A) and solid phase monomer compounds (1B) synthesized by standard split-pool synthesis employing FMOC chemistry. In each case, the three sub-libraries were independently prepared, and each differed by position of the cysteine residue (i.e., first, second, or third position within peptide chain).

The present invention relates to a class of monomer and related homo- and hetero-dimer compounds, which can be synthesized according to a number of approaches including as a self-assembled combinatorial library.

The homo- or hetero-dimer compounds of the invention are formed by a disulfide, sulfinyl thio, or olefin bond between two monomers having the structure

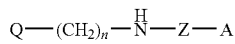 (I)

where, for each monomer (I),

Q is independently selected from H, NH$_2$,

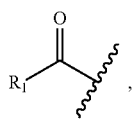

a cell uptake peptide moiety, and an inert substrate, where R$_1$ is selected from a straight or branched chain C$_1$ to C$_6$ hydrocarbon and an aromatic or heteroaromatic group;

n is independently an integer from 0 to about 5;

Z is independently a peptide containing at least two and up to about ten amino acids, where one of the amino acids is capable of forming a disulfide bond, sulfinyl thio linkage, or olefin bond; and A is independently an aromatic or heteroaromatic group connected to Z via a carbonyl linkage.

Aromatic or heteroaromatic groups A and R$_1$ can be any single, multiple, or fused ring structures, but preferably those that function as intercalator moieties capable of binding to a nucleic acid by inserting itself in between base pairs of adjacent nucleotides without unwinding and without extension of the nucleic acid helix. Aromatic or heteroaromatic intercalator compounds typically have a flat configuration, and are preferably polycyclic having at least two rings and typically not more than about six rings, more usually not more than about five rings, where at least two of the rings are fused. The rings may be substituted by a wide variety of substituents including, without limitation, alkyl groups of from one to four carbon atoms; oxy groups, which includes hydroxy, alkoxy and carboxy ester, generally of from one to four carbon atoms; amino groups, including mono- and di-substituted amino groups, particularly mono- and dialkyl amino, of from zero to eight, usually zero to six carbon atoms; thio groups, particularly alkylthio from one to four, usually one or two carbon atoms; cyano groups; non-oxo-carbonyl groups, such as carboxy and derivatives thereof, particularly carboxamide or carboxyalkyl, of from one to eight or one to six carbon atoms, usually two to six carbon atoms and more usually two to four carbon atoms; oxo-carbonyl or acyl, generally from one to four carbon atoms; halo groups, particularly of atomic number 9 to 35 (e.g., F, Cl, or Br).

Specific aromatic or heteroaromatic groups A and R$_1$ (associated carbonyl is shown) include, without limitation:

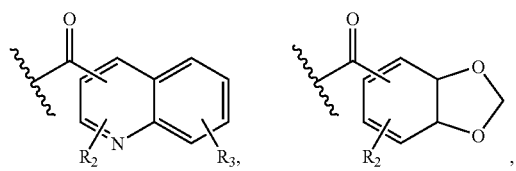

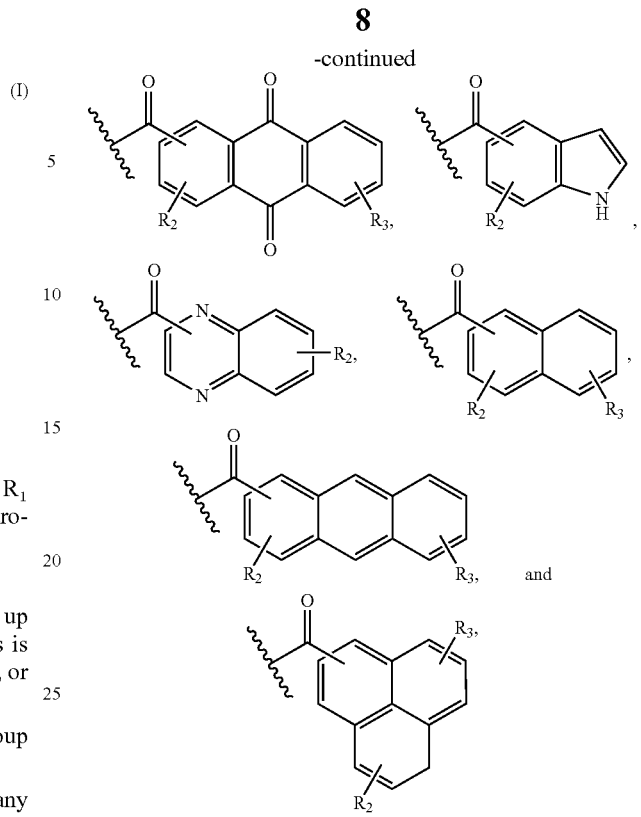

where R$_2$ and R$_3$ are optional, and can be any of the above-identified substituents. Preferably, R$_2$ and R$_3$ are independently selected from the group consisting of hydrogen, methyl, ethyl, propyl, amino, methylamine, ethylamine, dimethylamine, diethylamine, methoxy, ethoxy, propoxy, hydroxyl, cyano, and thiocyanato.

In peptide Z, the amino acid that is capable of forming a disulfide bond, sulfinyl linkage, or olefin bond is present at any position in the 2-10 amino acid peptide sequence. Formation of disulfide bonds, sulfinyl linkages, and olefin bonds is well known in the art. Disulfide bonds are formed by a covalent coupling of thiol groups from a cysteine or cysteine derivative. Sulfinyl linkages can be formed by well-known procedures, either by oxidation of a disulfide bond with mCPBA (Chayajarus et al., "Efficient Synthesis of Carbohydrate Thionolactones," *Tetrahedron Lett.* 47:3517-3520 (2006), which is hereby incorporated by reference in its entirety) or by oxidation with dimethyl dioxirane (Bourles et al., "Direct Synthesis of a Thiolato-S and Sulfinato-S Co$^{III}$ Complex Related to the Active Site of Nitrile Hydratase: A Pathway to the Post-Translational Oxidation of the Protein," *Angew. Chem. Int. Ed.* 44:6162-6165 (2005), which is hereby incorporated by reference in its entirety). Olefin bonds can be formed by α-amino acids having an unsaturated hydrocarbon sidechain using known procedures, such as those disclosed in PCT Patent Application Publication No. WO 2004/101476, which is hereby incorporated by reference in its entirety.

In a preferred embodiment, peptide Z is a dipeptide, tripeptide, or tetrapeptide. When peptide Z is a tripeptide, the tripeptide preferably has the structure —R$_4$—R$_5$—R$_6$—; —R$_5$—R$_4$—R$_6$—; —R$_5$—R$_6$—R$_4$—; —R$_4$—R$_6$—R$_5$—; —R$_6$—R$_4$—R$_5$—; or —R$_6$—R$_5$—R$_4$—, where R$_4$, R$_5$, and R$_6$ are amino acids and the amino acid capable of forming a disulfide bond, sulfinyl thio linkage, or olefin bond is R$_6$.

Any combination of amino acids can be used in the dimer compounds of the present invention including, without limitation, L-amino acids, D-amino acids, and N-methyl amino acids. Preferred amino acids for use in the dimer compound of the present invention include Cys, His, Lys, Phe, Ala, Ser, Asp, Asn, Val, Pro, Thr, Met, allyl-glycine (Al-Gly) and their derivatives, as well as their D-amino acids and N-methyl amino acids.

Inert substrates include, without limitation, resins, glass, thermoplastics, polymer materials, semiconductor materials, and metals. Suitable resins include, without limitation, polystyrene, polystyrene-co-divinylbenzene, and polyethylene glycol/polystyrene-co-divinylbenzene graft polymers. Suitable metals include, without limitation, gold, silver, and platinum. Suitable semiconductor materials include, without limitation, silicon, germanium, doped-silicon alloys, and compound materials such as gallium arsenide and indium phosphide.

In a preferred embodiment, the inert substrate is a resin bead having a diameter of between about 150 μm to about 250 μm.

According to one embodiment of the present invention, the dimer compound of the present invention is a homo- or hetero-dimer formed by a cysteine-cysteine disulfide bond or olefin bond between two monomers having a structure

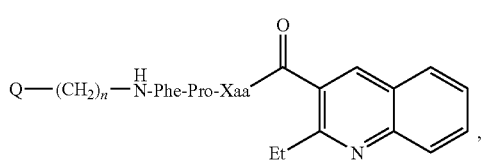

(II)

where, for each monomer (II),
Q is independently selected from H, NH$_2$, a cell uptake peptide moiety, and an inert substrate;
n is independently an integer from 0 to about 5; and
Xaa is Cys or Al-Gly.

In another embodiment, the dimer compound of the present invention is a hetero-dimer formed by a cysteine-cysteine disulfide bond or olefin bond between a first monomer having a structure

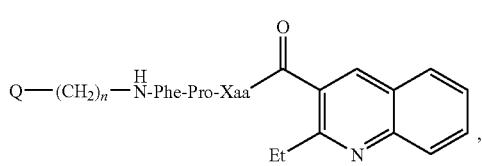

(II)

and a second monomer having a structure

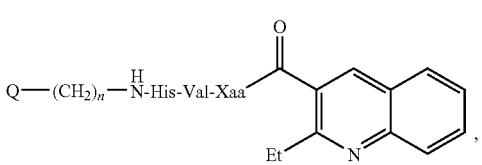

(III)

where, for each of monomers (II) and (III),
Q is independently selected from H, NH$_2$, a cell uptake peptide moiety, and an inert substrate;
n is independently an integer from 0 to about 5; and
Xaa is Cys or Al-Gly.

In yet another embodiment, the dimer compound of the present invention is a homo- or hetero-dimer formed by a cysteine-cysteine disulfide bond or olefin bond between a first and a second monomer, wherein the first and/or second monomers have a structure

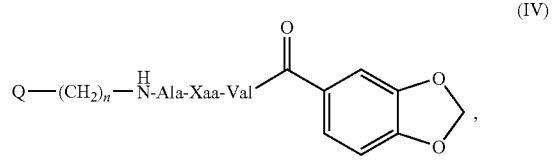

(IV)

where, for each monomer (IV),
Q is independently selected from H, NH$_2$, a cell uptake peptide moiety, and an inert substrate;
n is independently an integer from 0 to about 5; and
Xaa is Cys or Al-Gly.

In a further embodiment, the dimer compound of the present invention is a homo- or hetero-dimer formed by a cysteine-cysteine disulfide bond or olefin bond between a first and a second monomer, wherein the first and/or second monomers have a structure

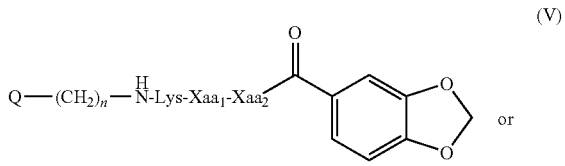

(V)

or

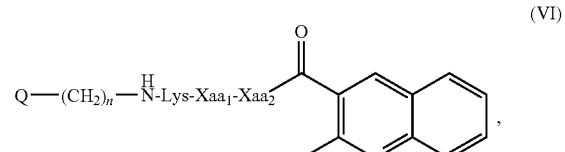

(VI)

where, for each of monomers (V) and (VI),
Q is independently selected from H, NH$_2$, a cell uptake peptide moiety, and an inert substrate;
n is independently an integer from 0 to about 5;
Xaa$_1$ is Cys or Al-Gly; and
Xaa$_2$ is Pro or Asn.

The present invention also relates to a method of selecting homo- and/or hetero-dimer compounds capable of selectively binding a target mRNA molecule. The target mRNA molecule can be the full length RNA product that exists in nature, or merely a fragment thereof that possesses the region of interest. In the latter approach, molecular modeling using appropriate software (e.g., RNA Structure) is preferable for determining whether the RNA molecule fragment will retain its shape when part of a minimal structure. Regardless, the target RNA preferably includes a structural- or sequence-specific configuration (i.e., secondary structure) that is targeted by the dimer compounds of the present invention. Preferably, the target mRNA molecule is characterized by a unique stem or stem-loop configuration, and the dimer or oligomer compounds of the present invention specifically target the unique stem or stem-loop structure.

As exemplified in the appended examples, the HIV-1 gal-pol mRNA possesses a regulatory sequence containing a stem/loop formation that can be targeted in this manner.

Another suitable target is the −1 ribosomal frameshifting of SARS coronavirus (Su et al., "An Atypical RNA Pseudoknot Stimulator and an Upstream Attenuation Signal for −1 Ribosomal Frameshifting of SARS Coronavirus," *Nucleic Acids Research* 33:4265-4275 (2005); Dos Ramos et al., "Programmed −1 Ribosomal Frameshifting in the SARS Coronavirus," *Biochemical Society Transactions* 32:1081-1083 (2004), each of which is hereby incorporated by reference in its entirety). It is expected that any mRNA having a similar frameshift site can be targeted in this manner. Moreover, applicants have demonstrated that the compounds of the present invention can also be used to target other regulatory sequences, such as repeat sequences associated with one or more disease states (e.g., inherited neuropathies, muscular dystrophies, Friedreich ataxia, lysosomal storage diseases, mitochondrial disorders, Huntington's disease, spinocerebellar ataxis (Machado-Joseph disease), dentatorubral pallidoluysian atrophy, and spinobulbar muscular atrophy (Kennedy's disease), fragile X syndrome, Jacobsen syndrome, diabetes mellitus, and myoclonus epilepsy).

Screening for target RNA binding involves providing a heterogeneous mixture of solution phase monomers according to formula (I) each having a structure where Q is independently selected from H, $NH_2$, and

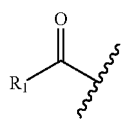

, $R_1$ is selected from a straight or branched chain $C_1$ to $C_6$ hydrocarbon and an aromatic or heteroaromatic group, and then equilibrating the heterogeneous mixture of solution phase monomers with a labeled target RNA molecule and a heterogeneous mixture of inert substrate-bound monomers each having a structure of formula (I) except where Q is an inert substrate. Inert substrate-bound monomers are preferably covalently attached to the solid support (Q). Methods of attaching compounds to solid supports are well-known in the art, and are exemplified in the accompanying Examples.

The equilibrating step is carried out under conditions effective to form homo- and/or hetero-dimers containing one solution phase monomer and one substrate-bound monomer. The target mRNA molecule is detected via the label, which becomes bound to the substrate after binding of the RNA molecule by the dimer. Homo- and/or hetero-dimer compounds capable of selectively binding the target RNA molecule are selected (and identified) based on detection of the label in this manner.

Preferably, the RNA target molecule is fluorescently labeled with fluorescent dyes, proteins, or nanocrystalline particles as is well known in the art. Detection of fluorescently labeled compounds can be carried out by methods well-known in the art.

After identifying a particular compound for its binding properties (i.e., for targeting a particular RNA molecule), screening for non-binding to non-target RNA molecules can be carried out using, e.g., total cellular RNA from mammalian cells, yeast, bacteria, plants, etc. This can be used to confirm specificity for the target RNA molecule.

Having thus screened a library of compounds for their ability to bind the target RNA molecule, the dimer compounds of the present invention can be synthesized in substantially pure form. Basically, the synthesis involves providing first and second monomers according to formula (I), which can be the same or different, and then reacting the monomers together under conditions effective to form a homo- or hetero-dimer compound as described above.

In one embodiment, peptide Z of each monomer contains a cysteine residue and the homo- or hetero-dimer compound is formed by a disulfide bond. In yet another embodiment, a dimer compound having a disulfide bond is treated under conditions effective to convert the disulfide bond into a sulfinyl thio linkage.

In an alternative embodiment, peptide Z of each monomer contains an α-amino acid containing an unsaturated hydrocarbon sidechain, such as allylglycine (Al-Gly), and the dimer is formed by an olefin bond.

These homo- and hetero-dimers can also be linked together to form longer oligomer chains. Oligomerization can be carried out by synthesizing an analog of the cysteine containing peptide in which an allylglycine is incorporated immediately after the diamine linker, followed by gamma-aminobutyric acid or other amino-alkanoic acid. Olefin cross-metathesis following cleavage of the compound from the bead provides the desired oligomer.

The dimer and oligomer compounds of the present invention can also be in the form of a salt, preferably a pharmaceutically acceptable salt. The term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

The dimer and oligomer compounds of the present invention can also be present in the form of a composition that comprises a carrier, preferably a pharmaceutically acceptable carrier. The compositions of the present invention can be in solid or liquid form, such as tablets, capsules, powders, solutions, suspensions, or emulsions.

The dimer and oligomer compounds may be orally administered, for example, with an inert diluent, or with an assimilable edible carrier, or it may be enclosed in hard or soft shell capsules, or it may be compressed into tablets, or it may be incorporated directly with food. For oral therapeutic administration, the agent of the present invention may be incorporated with excipients and used in the form of tablets, capsules, elixirs, suspensions, syrups, and the like. Such compositions and preparations should contain at least 0.1% of the agent. The percentage of the agent in these compositions may, of course, be varied and may conveniently be between about 2% to about 60% of the weight of the unit. The amount of agent in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar, or both. A syrup may contain, in addition to an active ingredient, sucrose as a sweetening agent, methyl and propylparabens as preservatives, a dye, and flavoring such as cherry or orange flavor.

The agent of the present invention may also be administered parenterally. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The dimer and oligomer compounds of the present invention may also be administered directly to the airways in the form of an aerosol. For use as aerosols, the agent of the present invention in solution or suspension may be packaged in a pressurized aerosol container together with suitable propellants, for example, hydrocarbon propellants like propane, butane, or isobutane with conventional adjuvants. The agent of the present invention also may be administered in a non-pressurized form such as in a nebulizer or atomizer.

Sustained release formulations include implantable devices that include a slow-dissolving polymeric matrix and one or more homo- or hetero-dimer compounds retained within the polymeric matrix. The matrix can be designed to deliver substantially the entire payload of the vehicle over a predetermined period of time, such as about one to two weeks up to about one to three months.

Although the formulations and compositions can also be delivered topically, it is also contemplated that the compositions can be delivered by various transdermal drug delivery systems, such as transdermal patches as known in the art.

In addition, the compounds of the present invention can be administered in using a delivery vehicle for passive or targeted delivery to particular cells that are known to possess the target RNA molecule. Any suitable passive or targeted delivery vehicle can be employed, including liposomes, polymeric nanoparticles, polyethylene glycol conjugates, and cell uptake peptides.

Targeting to the delivery vehicle to a cell of interest is typically achieved through the use of antibodies, binding fragments thereof, or nucleic acid aptamers that are bound or suspended to the surface of the delivery vehicle.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner where the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., Wang et al., "pH-sensitive Immunoliposomes Mediate Target-cell-specific Delivery and Controlled Expression of a Foreign Gene in Mouse," Proc. Natl. Acad. Sci. USA 84:7851 (1987), which is hereby incorporated by reference in its entirety). When liposomes are endocytosed by a target cell, for example, they can be routed to acidic endosomes which will destabilize the liposome and result in drug release.

The liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al., "Diffusion of Univalent Ions Across the Lamellae of Swollen Phospholipids," *J. Mol. Biol.* 13:238-252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference in its entirety.

Polymeric nanoparticles can be target to cell-surface marked using aptamers designed using the SELEX procedure (Farokhzad et al., "Targeted Nanoparticle-aptamer Bioconjugates for Cancer Chemotherapy In Vivo," *Proc. Natl. Acad. Sci. USA* 103(16):6315-6320 (2006), which is hereby incorporated by reference in its entirety). Nanoparticles and microparticles may comprise a concentrated core of drug that is surrounded by a polymeric shell (nanocapsules) or as a solid or a liquid dispersed throughout a polymer matrix (nanospheres). General methods of preparing nanoparticles and microparticles are described by Soppimath et al., "Biodegradable Polymeric Nanoparticles as Drug Delivery Devices," *J. Control Release* 70(1-2):1-20 (2001), which is hereby incorporated by reference in its entirety. Other polymeric delivery vehicles that may be used include block copolymer micelles that comprise a drug containing a hydrophobic core surrounded by a hydrophilic shell; they are generally utilized as carriers for hydrophobic drugs and can be prepared as found in Allen et al., "Colloids and Surfaces," *Biointerfaces* 16(1-4):3-27 (1999), which is hereby incorporated by reference in its entirety. Polymer-lipid hybrid systems consist of a polymer nanoparticle surrounded by a lipid monolayer. The polymer particle serves as a cargo space for the incorporation of hydrophobic drugs while the lipid monolayer provides a stabilizing interference between the hydrophobic core and the external aqueous environment. Polymers such as polycaprolactone and poly(D,L-lactide) may be used while the lipid monolayer is typically composed of a mixture of lipids. Suitable methods of preparation are similar to those referenced above for polymer nanoparticles. Derivatized single chain polymers are polymers adapted for covalent linkage of a biologically active agent to form a polymer-drug conjugate. Numerous polymers have been proposed for synthesis of polymer-drug conjugates including polyaminoacids, polysaccharides such as dextrin or dextran, and synthetic polymers such as N-(2-hydroxypropyl)methacrylamide (HPMA) copolymer. Suitable methods of preparation are detailed in Veronese and Morpurgo, "Bioconjugation in Pharmaceutical Chemistry," *IL Farmaco* 54(8):497-516 (1999), which is hereby incorporated by reference in its entirety.

By modifying the dimer compounds, the compounds can be administered as a conjugate with a pharmaceutically acceptable water-soluble polymer moiety. By way of example, a polyethylene glycol conjugate is useful to increase the circulating half-life of the dimer compound, and to reduce the immunogenicity of the molecule. Specific PEG conjugates are described in U.S. Patent Application Publ. No. 20060074200 to Daugs et al., which is hereby incorporated by reference in its entirety. Liquid forms, including liposome-encapsulated formulations, are illustrated by injectable solutions and oral suspensions. Exemplary solid forms include capsules, tablets, and controlled-release forms, such as a miniosmotic pump or an implant. Other dosage forms can be devised by those skilled in the art, as shown, for example, by Ansel and Popovich, Pharmaceutical Dosage Forms and Drug Delivery Systems, $5^{th}$ Edition (Lea & Febiger 1990), Gennaro (ed.), Remington's Pharmaceutical Sciences, $19^{th}$ Edition (Mack Publishing Company 1995), and by Ranade and Hollinger, Drug Delivery Systems (CRC Press 1996), each of which is hereby incorporated by reference in its entirety.

The dimer and oligomer compounds can be further modified to enhance cellular uptake of the compounds. For example, the dimers and oligomers can be modified with a cell uptake peptide, such as HIV-1 TAT polypeptide or derivative thereof, oligoarginine polypeptide, or *Mycobacterium tuberculosis* McelA polypeptide (22-amino acid sequence termed Inv3), linked to carboxy-terminal end of the peptide chain (de Coupade et al., "Novel Human-derived Cell-penetrating Peptides for Specific Subcellular Delivery of Therapeutic Biomolecules," *Biochem J.* 390(2):407-418 (2005); U.S. Patent Application Publ. No. 20030032593 to Wender et al.; Wender et al., "The Design, Synthesis, and Evaluation of Molecules that Enable or Enhance Cellular Uptake: Peptoid Molecular Transporters," *Proc Natl Acad Sci U.S.A.* 97:13003-13008 (2000); Brunner et al., "Targeting DNA Mismatches with Rhodium Intercalators Functionalized with a Cell-penetrating Peptide," *Biochemistry* 45:12295-12302 (2006), Turner et al., "Synthesis, Cellular Uptake and HIV-1 Tat-dependent Trans-activation Inhibition Activity of Oligonucleotide Analogues Disulphide-conjugated to Cell-penetrating Peptides," *Nucl Acids Res.* 33(1):27-42 (2005); Lu et al., "A Cell-penetrating Peptide Derived from Mammalian Cell Uptake Protein of *Mycobacterium tuberculosis*," *Anal Biochem.* 353(1): 7-14 (2006), each of which is hereby incorporated by reference in its entirety). Thus, in one or more of monomers (I)-(VI) that form the dimer or oligomer, the Q group linked to the carboxy terminus of the peptide chain is replaced by a cell uptake peptide.

As discussed below, and by way of example, several dimer compounds of the present invention are effective in inhibiting the expression of HIV-1 Gag-pol, thereby affording a therapeutic treatment for HIV-1 through the targeting of the Gag-pol mRNA frameshift site. Because HIV-1 infection implicates $CD4^+$ T helper cells, macrophages, and dendritic cells, targeted delivery to one or more of these cell types is desirable though not required.

Figure 10:
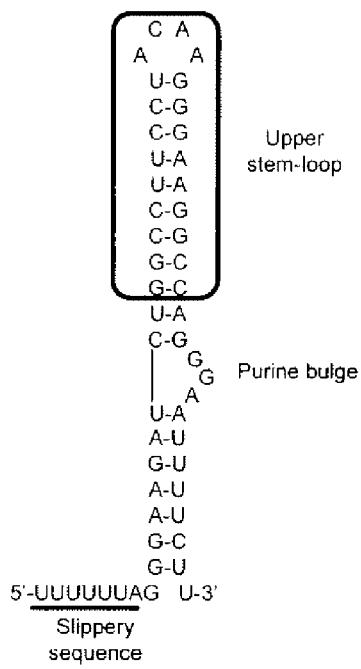
FIG. 10 shows secondary structure (SEQ ID NO:5) of the HIV-1 frameshift-inducing RNA stem-loop with the upper stem-loop sequence used in the binding analysis highlighted in a box. The slippery sequence where the −1 frameshift occurs is underlined.

It has been estimated that 39.5 million people are infected with the Human Immunodeficiency Virus ("HIV") worldwide, 4.3 million of these becoming infected in 2006 alone. Expression and proteolysis of the polyprotein Pol is required for the production of three proteins vital to viral proliferation (HIV-integrase, -protease, and -reverse transcriptase). Pol is produced only as a Gag-Pol fusion protein, which is translated 5-10% with respect to Gag (depending on the technique used for measurement) via a tightly regulated −1 nucleotide ribosomal frameshift (Park et al., "Overexpression of the gag-pol Precursor from Human Immunodeficiency Virus Type 1 Proviral Genomes Results in Efficient Proteolytic Processing in the Absence of Virion Production," *J. Virol.* 65:5111-5117 (1991); Jacks et al., "Characterization of Ribosomal Frameshifting in HIV-1 gag-pol Expression," *Nature* 331:280-283 (1988); Parkin et al., "Human Immunodeficiency Virus Type 1 gag-pol Frameshifting is Dependent on Downstream mRNA Secondary Structure: Demonstration by Expression in vivo" *J. Virol.* 66:5147-5151 (1992), each of which is hereby incorporated by reference in its entirety). Two principal factors responsible for this frameshift are (i) a A "slippery sequence" where the frameshift occurs and (ii) a highly conserved downstream stem-loop which has been shown to play a vital role in frameshifting (Telenti et al., "Analysis of Natural Variants of the Human Immunodeficiency Virus Type 1 gag-pol Frameshift Stem-Loop Structure," *J. Virol.* 76:7868-7873 (2002), which is hereby incorporated by reference in its entirety) (see FIG. 10). Precise control of frameshifting is essential to viral proliferation, as small changes in Gag-Pol expression levels drastically inhibit virus production (Karacostas et al., "Overexpression of the HIV-1 Gag-Pol Polyprotein Results in Intracellular Activation of HIV-1 Protease and Inhibition of Assembly and Budding of Virus-like Particles," *Virology* 193:661-671 (1993); Hung et al., "Importance of Ribosomal Frameshifting for Human Immunodeficiency Virus Type 1 Particle Assembly and Replication," *J. Virol.* 72:4819-4824 (1998); Shehu-Xhilaga et al., "Maintenance of the Gag/Gag-Pol Ratio Is Important for Human Immunodeficiency Virus Type 1 RNA Dimerization and Viral Infectivity," *J. Virol.* 75:1834-1841 (2001), each of which is hereby incorporated by reference in its entirety).

Based on the results demonstrated in the following Examples, several compounds of the present invention have demonstrated affinity for binding selectively to the HIV-1 frameshift regulatory sequence. These compounds are believed to inhibit HIV-1 replication. Thus, a further aspect of the present invention relates to a method of inhibiting HIV-1 proliferation. This method involves providing a dimer or oligomer compound according to the present invention and contacting an HIV-1 mRNA that encodes Pol polypeptide with the dimer or oligomer compound under conditions effective to alter normal expression of the Pol polyprotein and thereby inhibit HIV-1 proliferation.

According to this aspect of the present invention, contacting an HIV-1 mRNA that encodes Pol polypeptide with the dimer or oligomer compound of the present invention may involve contacting an HIV-1 infected cell or (prior to infection) contacting a cell that is targeted by HIV-1 such that the dimer or oligomer compound of the invention is internalized into the cell. Internalization will allow the dimer or oligomer compound to bind an HIV-1 frameshift regulatory sequence which is important to frameshifting of the Gag-pol RNA, which in turn is essential to viral proliferation. For example, small changes in Gag-Pol expression levels in HIV-1 drastically inhibit virus production. Contacting an HIV-1 mRNA that encodes Pol polypeptide with a dimer or oligomer compound of the present invention may be carried out in vitro, such as in a sample, or in vivo in an animal or patient. Thus, this aspect of the present invention can be used to treat blood samples obtained from HIV-1 infected patients.

Another aspect of the present invention relates to a method of treating HIV-1 in a human patient. This method involves administering to a human patient a dimer or oligomer compound according to the first aspect of the present invention under conditions effective to alter normal expression of HIV-1 Pol polyprotein, thereby disrupting HIV-1 proliferation to treat the human patient for HIV-1.

In practicing the methods of treating HIV-1 in a patient of the present invention, the administering step is carried out by administering an agent (i.e., the homo- or hetero-dimer or oligomer compound, or a composition containing the dimer or oligomer compound) orally, intradermally, intramuscularly, intraperitoneally, intravenously, subcutaneously, or intranasally. The agent of the present invention may be administered alone or with suitable pharmaceutical carriers, and can be in solid or liquid form, such as tablets, capsules, powders, solutions, suspensions, or emulsions.

In treating an HIV-1 infected patient, it is intended that the dimer compounds can be used effectively to reduce viral load in a patient or, under certain circumstances, completely eradicate the virus.

The dimer compounds, by virtue of their affinity for binding to the HIV-1 Gag-pol RNA, can also be used for diagnostic screening to detect the presence of HIV-1 virus in a sample. This method involves providing a homo- or heterodimer compound according to the first aspect of the present invention, where the dimer compound is immobilized on a surface. The immobilized dimer compound is contacted with a sample under conditions effective to permit the HIV-1 Gagpol (containing the mRNA frameshift regulatory molecule of HIV-1) to bind specifically to the immobilized homo- or hetero-dimer compound. Presence of the mRNA molecule is detected in the sample based on the binding (i.e., a detectable event). Detection can be achieved using label-free detection schemes like those reported in U.S. Patent Application Publ. No. 20030112446 to Miller and Rothberg, which is hereby incorporated by reference in its entirety. Detection can also be achieved using secondary detection labels, such as aptamers or antibodies.

In a preferred embodiment of this aspect of the present invention, the sample is from a blood sample, preferably a human blood sample. Thus, this method of the present invention can be used to detect the presence of HIV-1 in human blood samples.

The surface on which the homo- or hetero-dimer compound of the present invention is immobilized on may be made from a variety of materials and/or types of devices including, without limitation, a silicon-containing chip or a dipstick-like surface which can be inserted into a liquid sample for testing.

Other diseases and/or disorders are also amenable to treatment using the compounds of the present invention.

For example, there are many lines of evidence supporting a toxic RNA mechanism in myotonic dystrophy. Myotonic dystrophy type 1 (MD1) is the most common form of muscular dystrophy in adults, affecting 1 in 8000 people (Machuca-Tzili et al., "Clinical and Molecular Aspects of the Myotonic Dystrophies: A Review," *Muscle Nerve* 32:1-18 (2005), which is hereby incorporated by reference in its entirety). DM1 is characterized by multisystemic symptoms, including myotonia, wasting of the muscle, testicular atrophy, cataracts, and cardiac defects. Unlike typical genetic diseases, which follow the traditional central dogma (a mutated gene is transcribed and translated to an altered encoded protein which affects cellular function), DM1 is governed by an RNA mediated mechanism (Wheeler et al., "Myotonic Dystrophy: RNA-mediated Muscle Disease," *Curr. Opin. Neurology* 20:572-576 (2007), which is hereby incorporated by reference in its entirety). Specifically, DM1 is caused by expansion of CTG repeats located in the 3' untranslated region of the DMPK (DM protein kinase) gene on chromosome 19 q (Brook et al., "Molecular Basis of Myotonic Dystrophy: Expansion of a Trinucleotide (CTG) Repeat at the 3' End of a Transcript Encoding a Protein Kinase Family Member," *Cell* 68:799-808 (1992), which is hereby incorporated by reference in its entirety). Transcription produces toxic mRNA containing hundreds to thousands of (CUG) repeats, which form long and stable hairpin structures (Michalowski et al., "Visualization of Double-stranded RNAs from the Myotonic Dystrophy Protein Kinase Gene and Interactions with CUG-binding Protein," *J. Nucleic Acids Res.* 27:3534-42 (1999), which is hereby incorporated by reference in its entirety). The (CUG) repeat RNA accumulates in nuclear foci, and sequesters RNA binding proteins such as the MBNL (muscleblind) family of splicing regulators (Lin et al., "Failure of MBNL1-dependent Post-natal Splicing Transitions in Myotonic Dystrophy," *Hum. Mol. Genet.* 15:2087-2097 (2006), which is hereby incorporated by reference in its entirety). (CUG) repeat sequestration of these splicing regulators causes misregulated and aberrant splicing of a variety of gene products, including the chloride channel 1, which is a major cause of myotonia in DM (Mankodi et al., "Expanded CUG Repeats Trigger Aberrant Splicing of ClC-1 Chloride Channel Pre-mRNA and Hyperexcitability of Skeletal Muscle in Myotonic Dystrophy," *Molecular Cell* 10:35-44 (2002); Wheeler et al., "Correction of ClC-1 Splicing Eliminates Chloride Channelopathy and Myotonia in Mouse Models of Myotonic Dystrophy," *J. Clin. Invest.* 117:3952-3957 (2007), each of which is hereby incorporated by reference in its entirety). As such, an RNA mediated model of DM1 pathogenesis has been established.

The expanded $(CUG)_n$ or $(CCUG)_n$ repeat RNA of DM1 and DM2 function in pathogenesis by causing misregulated and aberrant splicing. The $(CUG)_n$ repeat RNA accumulates in the nucleus and interacts with CUG binding proteins. These CUG binding proteins such as CELFs (CUG binding proteins and ETR3 like factors) and MBNLs (muscleblind) are regulators of splicing. CELF proteins, in particular CUGBP1 (CUG binding protein 1) show activity increase in myotonic dystrophy (Timchenko et al., "Identification of a $(CUG)_n$ Triplet Repeat RNA-binding Protein and Its Expression in Myotonic Dystrophy," *Nucleic Acids Research* 24:4407-4414 (1996); Timchenko et al., "RNA CUG Repeats Sequester CUGBP1 and Alter Protein Levels and Activity of CUGBP1," *Journal of Biological Chemistry* 276:7820-7826 (2001), each of which is hereby incorporated by reference in its entirety). The $(CUG)_n$ RNA forms nuclear foci, or inclusions, in muscle cells (Taneja et al., "Foci of Trinucleotide Repeat Transcripts in Nuclei of Myotonic Dystrophy Cells and Tissues," *Journal of Cell Biology* 128:995-1002 (1995), which is hereby incorporated by reference in its entirety) and muscleblind (MBNL) proteins such as MBNL1 are sequestered to these foci (Jiang et al., "Myotonic Dystrophy Type 1 Associated with Nuclear Foci of Mutant RNA, Sequestration of Muscleblind Proteins, and Deregulated Alternative Splicing in Human Neurons," *Human Molecular Genetics* 12:3079-3088 (2004); Mankodi et al., "Muscleblind Localizes to Nuclear Foci of Aberrant RNA in Myotonic Dystrophy Types 1 and 2," *Human Molecular Genetics* 10:2165-2170 (2001), each of which is hereby incorporated by reference in its entirety). The muscleblind and CELF proteins control developmentally programmed mRNA processing. In the regulation of splicing, MBNL proteins antagonize CELF proteins activities. When CELF protein activity dominates, splicing follows an embryonic pattern. Alternatively, when MBNL activity dominates, splicing follows an adult pattern. Specifically, MBNL1 promotes and regulates alternative exon inclusion in muscle differentiation (Pascual et al., "The Muscleblind Family of Proteins: An Emerging Class of Regulators of Developmentally Programmed Alternative Splicing," *Differentiation* 74:65-80 (2006), which is hereby incorporated by reference in its entirety). Thus, the sequestration of MBNL proteins in DM1 leads to an imbalance in the MBNL/CELF activity ratio, thereby causing misregulation of mRNA processing. Importantly, it has been shown in mouse models that $(CUG)_n$ repeat expression or MBNL1 ablation both result in similar splicing defects as seen in human DM1 (Lin et al., "Failure of MBNL1-dependent Postnatal Splicing Transitions in Myotonic Dystrophy," *Human Molecular Genetics* 15:2087-2097 (2006), which is hereby incorporated by reference in its entirety). Additionally, the altered spliceopathy seen in long $CUG)_n$ RNA repeat expressing muscle cells can be reversed by MBNL1 overexpression (Kanadia et al., "Reversal of RNA Missplicing and Myotonia After Muscleblind Overexpression in a Mouse Poly(CUG) Model for Myotonic Dystrophy," *PNAS U.S.A.* 103:11748-11753 (2006), which is hereby incorporated by reference in its entirety). As such, small molecules capable of binding (CUG) repeat RNA and disrupting its interaction with splicing proteins are highly desirable as potential therapeutic agents to restore normal splicing in DM1.

The altered spliceopthy associated with DM1 affects many gene products (Table 1) (Ranum et al., "RNA-mediated Neuromuscular Disorders," *Annual Review of Neuroscience* 29:259-277 (2006), which is hereby incorporated by reference in its entirety). Some of the most prevalent include the altered splice product of the insulin receptor which causes insulin resistance in the DM patients. Also, it has been shown that defects in the splicing of chloride channel 1 (ClC1) are responsible for myotonia in DM1 (Mankodi et al., "Expanded CUG Repeats Trigger Aberrant Splicing of ClC-1 Chloride Channel Pre-mRNA and Hyperexcitability of Skeletal Muscle in Myotonic Dystrophy," *Molecular Cell* 20:35-44 (2002); Wheeler et al., "Correction of ClC-1 Splicing Eliminates Chloride Channelopathy and Myotonia in Mouse Models of Myotonic Dystrophy," *Journal of Clinical Investigation* 117:3952-3957 (2007), each of which is hereby incorporated by reference in its entirety). In addition, altered splicing of cardiac troponin T leads to cardiac abnormalities. In the brain, Tau, APP (amyloid precursor protein), and NMDAR-1 (N-methyl-D-aspartate receptor) are alternatively spliced and this process has been hypothesized to lead to mental retardation commonly associated with DM. Finally, a variety of altered splice products including MTMR1 (myotubularin-related protein 1) and RyR (ryanodine receptor) are associated with muscle wasting (Ranum et al., "RNA-mediated Neuromuscular Disorders," *Annual Review of Neuroscience* 29:259-277 (2006); Osborne et al., "RNA-dominant Diseases," *Human Molecular Genetics* 15(Review 2):R162-R169 (2006), each of which is hereby incorporated by reference in its entirety).

TABLE 1

Genes Identified to be Alternatively Spliced in DM1, their location, and the exons or introns affected

| Tissue | Gene | Target |
| --- | --- | --- |
| Skeletal Muscle | ALP | Ex 5a, 5b |
| | CAPN3 | Ex 16 |
| | CLCN1 | Int 2, ex 7a, 8a |
| | FHOS | Ex 11a |
| | GFATI | Ex 10 |
| | IR | Ex 11 |
| | MBNL1 | Ex 7 |
| | MBNL2 | Ex 7 |
| | NRAP | Ex 12 |
| | MTMR1 | Ex 2.1, 2.2 |
| | RYR1 | Ex 70 |
| | z-titin | Ex Zr4, Zr5 |
| | m-titin | M-line ex 5 |
| | ZASP | Ex 11 |
| | SERCA1 | Ex 22 |
| | SERCA2 | Int 19 |
| Heart | ALP | Ex 5 |
| | TNNT2 | Ex 5 |
| | ZASP | Ex 11 |
| | m-titin | M-line ex 5 |
| | KCNAB1 | Ex 2 |
| Brain | TAU | Ex 2, 10 |
| | APP | Ex 7 |
| | NMDAR1 | Ex 5 |

To date, alternative splicing of these genes has been attributed to myotonia, muscle wasting, insulin resistance, cardiac defects and mental problems.

In addition to muscular dystrophy, other unstable noncoding expanded repeats are commonly associated with neurological and muscular disease (Table 2) (Machuca-Tzili et al., "Clinical and Molecular Aspects of the Myotonic Dystrophies: A Review," *Muscle Nerve* 32:1-18 (2005), which is hereby incorporated by reference in its entirety).

TABLE 2

Common Diseases Associated with Noncoding Expanded Repeat Sequences

| Disease | Repeat | Normal (n) | Disease (n) |
| --- | --- | --- | --- |
| Myotonic Dystrophy 1 | $(CTG)_n$ | 5-37 | 50->2000 |
| Friedreichs Ataxia | $(GAA)_n$ | 6-32 | 200-1700 |
| Spinocerebellar Ataxia 8 | $(CTG)_n$ | 16-92 | >100 |
| Spinocerebellar Ataxia 12 | $(CAG)_n$ | 7-45 | 55-80 |
| Fragile X Syndrome | $(CGG)_n$ | 4-50 | >200 |
| Jacobsen Syndrome | $(CCG)_n$ | 11 | >100 |
| Myotonic Dystrophy 2 | $(CCTG)_n$ | 104-176 | 75-11000 |
| Diabetes Mellitus | $(ACAGGGGT(G/C))_n$ SEQ ID NO: 12 | 110-150 | 30-44 |
| Myoclonus Epilepsy | $(CCCCGCCCCGCG)_n$ SEQ ID NO: 13 | 2-3 | 30-75 |

TABLE 2-continued

Common Diseases Associated with Noncoding
Expanded Repeat Sequences

| Disease | Repeat | Normal (n) | Disease (n) |
|---|---|---|---|
| Spinocere-bellar Ataxia 10 | (ATTCT)$_n$ | 10-22 | 800-4500 |

Based on the results demonstrated in the following Examples, several compounds of the present invention have demonstrated affinity for binding selectively to expanded repeat RNA sequences. These compounds can be used to interfere with the sequestration of splicing proteins by these expanded repeat RNA sequences. Thus, a further aspect of the present invention relates to a method of interfering with the interaction between an expanded repeat RNA sequence and a splicing protein. This method is carried out by contacting the expanded repeat RNA sequence with a dimer or oligomer compound of the present invention under conditions effective to prevent splicing protein sequestration by the expanded repeat RNA sequence. It is intended that compounds of the present invention can reduce the total amount of splicing protein that is sequestered by these repeat sequences, and thereby inhibit formation of dangerous foci.

Another aspect of the present invention relates to a method of treating a disease or disorder associated with expanded repeat RNA sequences. This method involves providing a dimer or oligomer compound according to the present invention, and administering the compound to a patient, preferably a mammal such as a human, under conditions effective to alter function of an expanded repeat RNA sequence, thereby disrupting interaction between the RNA repeat sequence and splicing proteins to treat the subject for the disorder. As used herein, treatment can include stopping or reversing progression of the disease or disorder, or controlling symptoms thereof.

The appropriate dose regimen, the amount of each dose administered, and specific intervals between doses of the active compound will depend upon the particular active compound employed, the conditions of the patient being treated, and the nature and severity of the disorder or conditions being treated. Preferably, the active compound is administered in an amount and at an interval that results in the desired treatment of or improvement in the disorder or condition being treated.

As one skilled in the art will readily appreciate, the compounds of the present invention can be used alone or in combination with other treatments of expanded repeat disorders as a combination therapy.

EXAMPLES

The examples below are intended to exemplify the practice of the present invention but are by no means intended to limit the scope thereof.

Example 1

Preparation of an 11,325 Member Resin Bound Dynamic Combinatorial Library

A Resin Bound Dynamic Combinatorial Library was designed for the construction of compounds that could be screened for binding affinity to target nucleic acid molecules.

As described below, the library members are formed by Cys-Cys disulfide bond formation between resin bound monomers and solution phase monomers. A total of 150 building blocks were prepared, which generated 11,325 unique library members when allowed to equilibrate by disulfide exchange. The 150 building blocks are represented by five amino acid residues at one position, five amino acid residues at a second position, the location of cysteine at each of the three peptide residues, and two carboxylic acid intercalators (or 5×5×3×2=150).

Synthesis of solution phase monomers was performed by standard split-pool synthesis employing FMOC chemistry. Three sub-libraries (see FIG. 1A) were independently prepared in which the position of the cysteine differs so that cleavage of the resin results in a heterogeneous mixture containing an equal distribution of molecules having cysteine in first, second, or third position (i.e., sub-libraries 1, 2, and 3). Briefly, Wang resin (100-200 mesh size, 1 mmol/g loading) was activated through the addition of 1-1'-carbonyl-di-imidizole (1620 mg, 5 mmol, 10 eq) in 12 mL of dimethylformamide ("DMF"). This suspension was rotated on a LabQuake™ rotator for 12 hours. The vessel was then evacuated and washed three times with 15 mL methylene chloride ("DCM"). Propane diamine (421 µL, 5 mmol, 10 eq) was added in 12 ml of DMF and rotated for an additional 12 hours. To this resin (sub-library 1, FIG. 1A) was added FMOC-Cys (trityl ("Trt"))-OH (879 mg, 1.5 mmol, 3 eq), HBTU (570 mg, 1.5 mmol, 3 eq), and diisopropylethylamine ("DIPEA") (424 µL, 2.5 mmol, 5 eq) in 10 ml DMF, and rotated for 1 hour. Following FMOC deprotection (20% piperidine/DMF, 30 min.), the product was washed using a universal washing scheme that was employed for all solid phase synthesis, consisting of three washes with DCM, three washes with THF, three washes with DMF, three washes with MeOH, and three final washes with DMF.

After washing, the resin was split into 5 vessels and amino acids 1-5 (His, Lys, Phe, Ala, Ser) were coupled (in position AA$_1$ of FIG. 1A). Following FMOC deprotection, the resin was pooled, split into five vessels, and amino acids 6-10 (Asp, Val, Pro, Thr, Met) were coupled (in position AA$_2$ of FIG. 1A). Sub-libraries 2 and 3 (FIG. 1A) were prepared similarly, but varying the position of the cysteine residue. Following FMOC deprotection, the resin was pooled, mixed, split into two vessels, and coupled to carboxylic acid

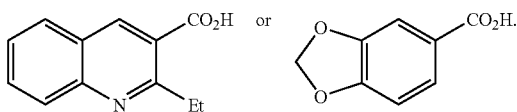 [SMILES: CCc1nc2ccccc2cc1C(=O)O ; "or" ; O=C(O)c1ccc2c(c1)OCO2]

Synthesis of each sub-library was performed as described above. To couple amino acids 1-5 [1: (Fmoc-Lys(Boc)-OH (141 mg, 0.3 mmol, 3 eq), 2: (Fmoc-His(Trt)-OH (186 mg, 0.3 mmol, 3 eq), 3: (Fmoc-Ser(Trt)-OH (170 mg, 0.3 mmol, 3 eq), 4: (Fmoc-Phe-OH (116 mg, 0.3 mmol, 3 eq), 5: (Fmoc-Ala-OH.2H$_2$O (99 mg, 0.3 mmol, 3 eq)] were weighed out into 5 separate vials containing HBTU (114 mg, 0.3 mmol, 3 eq), and DIPEA (85 µL, 0.5 mmol, 5 eq). 5 ml of DMF was added to each vial and the contents were added to separate vessels of washed resin and allowed to rotate for 30 minutes. To couple amino acids 6-10 [6: (Fmoc-Asn(Trt)-OH (178 mg, 0.3 mmol, 3 eq), 7: (Fmoc-Val-OH (102 mg, 0.3 mmol, 3 eq), 8: (Fmoc-Pro-OH (101 mg, 0.3 mmol, 3 eq), 9: (Fmoc-Thr (Trt)-OH 175 mg, 0.3 mmol, 3 eq), 10: (Fmoc-Met-OH (99 mg, 0.3 mmol, 3 eq)] were used and coupled as described above. After synthesis of the 3 amino acids was performed, each sub-library was split into two vessels. To couple carboxylic acids

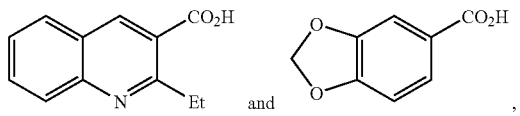 [SMILES: CCc1nc2ccccc2cc1C(=O)O ; O=C(O)c1ccc2c(c1)OCO2]

1: (3-carboxy-2-ethyl-3-quinolinium chloride 357 mg, 2.25 mmole, 3 eq), 2: (piperizinoic acid 452 mg, 2.25 mmole, 3 eq) were used and coupled as described above. The sublibraries were pooled and the resin was washed thoroughly. Lastly, products were cleaved/Boc and Trt deprotected in 10 mL of a 1% triethylsilane ("TES")/50% trifluoroacetic acid ("TFA") solution in DCM for one hour. Compounds were purified by precipitation in chilled ether (−20° C.). Solids were concentrated by centrifugation (2500 rpm, 10 min), the solution was removed, and fresh ether was added. The solution was mixed by vortex and solids were again concentrated by centrifugation. This series was repeated five times. After the last washing step the solids were dried by lyophilization, resulting in an off-white powder.

The synthesis of the solid-phase of the library utilized similar monomer assembly in conjunction with a resin (TentaGel) and a photolabile linker.

Photolabile linker FMOC-Anp-OH was prepared using a published procedure (Tan et al., "Synthesis and Preliminary Evaluation of a Library of Polycyclic Small Molecules for Use in Chemical Genetic Assays," *J. Am. Chem. Soc.* 121:S12 (1999), which is hereby incorporated by reference in its entirety).

Three resins were used to encode the position of the cysteine residue:
  Resin A: 140-170 nm, 0.45 mmol/g, 0.86 nmol/bead
  Resin B: 200-250 nm, 0.24 mmol/g, 1.50 nmol/bead
  Resin C: 280-320 nm, 0.23 mmol/g, 3.50 nmol/bead.
All resin was made to be 0.86 nmol/bead by reacting with appropriate amounts of methoxyacetic acid in the presence of FMOC-Anp-OH. 1 g of each resin type was placed in a separate reaction vessel and washed once with DCM. To resin A was added FMOC-Anp-OH (583 mg, 1.35 mmol, 3 eq.), HBTU (513 mg, 1.35 mmol, 3 eq.), and DIPEA (391 µl, 2.25 mmol, 5 eq.) in 10 ml of DMF. This solution was agitated for 4 hours on a LabQuake™ rotator. To resin B was added FMOC-Anp-OH (332 mg, 0.77 mmol, 1.71 eq.), methoxyacetic acid (45 µl, 0.58 mmol, 1.29 eq.), HBTU (513 mg, 1.35 mmol, 3 eq.), and DIPEA (391 µl, 2.25 mmol, 5 eq.) in 10 ml of DMF. This solution was agitated for 4 hours on a LabQuake™ rotator. To resin C was added FMOC-Anp-OH (138 mg, 0.32 mmol, 0.72 eq.), methoxyacetic acid (79 µl, 1.03 mmol, 2.28 eq.), HBTU (513 mg, 1.35 mmol, 3 eq.), and DIPEA (391 µl, 2.25 mmol, 5 eq.) in 10 ml of DMF. This solution was agitated for 4 hours on a LabQuake™ rotator.

As with the solution phase synthesis, solid phase components were prepared using an analogous split-pool methodology, with the exception of substituting FMOC-Cys-StBu-OH as the cysteine component. This was done to generate a disulfide protected cysteine on solid support, which would facilitate disulfide exchange between solid- and solution-phase components. In addition, the size of the resin bead was coordinated with the amino acid position of the coupled cysteine residue (FIG. 1B), which allowed for easy visualization under 4× magnification. Upon completion of solid phase building blocks, Trt and Boc protecting groups were removed by the addition of 1% TES/50% TFA in DCM for 1 hour. Mass spectrometry data of the cleavage solution showed a single mass corresponding to trityl. Therefore, it was concluded that no peptide product was cleaved from the resin.

Example 2

Figure 1B:
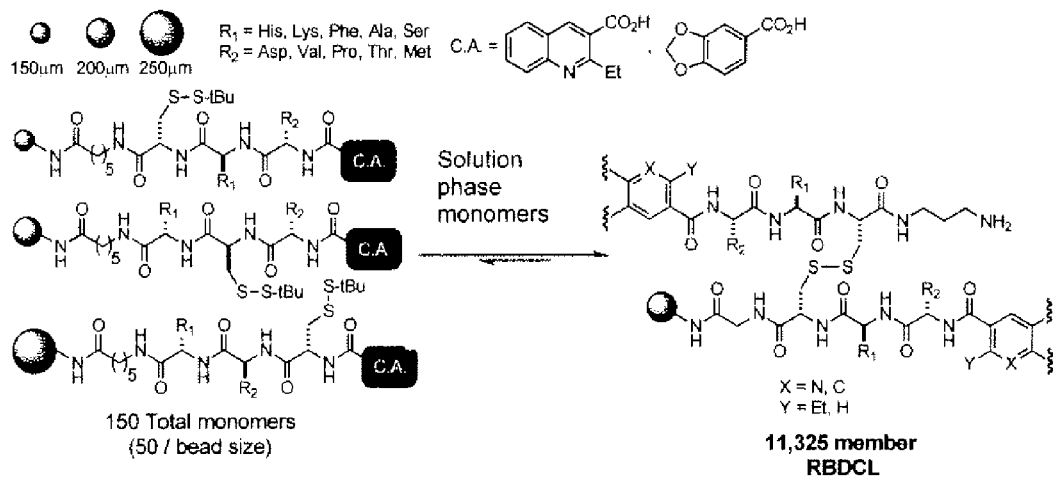

General Protocol for Screening 11,325 Member Resin Bound Dynamic Combinatorial Library Having synthesized the 150 solution-phase and solid-phase monomer components of the RBDCL, the library can be formed by combining the solution-phase and solid-phase monomer components under conditions effective to allow disulfide bond formation (FIG. 1B). Screening of the library can be carried out with any desired fluorescently labeled target nucleic acid molecule (FIG. 2), but preferably those containing a secondary structure having a stem or stem/loop formation.

Basically, the solid phase library members are first transferred to 1.5 mL solid phase reaction vessel and then 150 beads from each size of resin (Resin A, B, and C) are manually counted and transferred to the vessel (387 nmole of total resin bound material), which allows for a 3× copy library coverage. That is, 3 beads of each unique resin bound compound are screened. For all screening procedures 1×PBS at pH 7.4 was used as buffer. Importantly, this pH range is amenable for dynamic disulfide exchange (Corbett et al., "Dynamic Combinatorial Chemistry," *Chemical Reviews*, 106:3652-3711 (2006); Whitesides et al., "Equilibrium Constants for Thiol-disulfide Interchange Reactions: A Coherent Corrected Set," *J. Org. Chem.* 58:642-647 (1993), each of which is hereby incorporated by reference in its entirety). A freshly prepared heterogeneous mixture of solution phase compounds (30 nmole of total solution phase material, 1 mL of 30 µM based on average molecular weight), and fluorescently labeled target nucleic acid molecule (1 nmole) are then added to the resin (Table 3).

TABLE 3

Moles and Equivalents of RBDCL Components Used for Screening

| Solid-phase component | + RNA + | Solution-phase component | $\rightleftharpoons$ RBDCL | High-affinity ligands |
|---|---|---|---|---|
| moles | 387 E$^{-9}$ | 1.00 E$^{-9}$ | | 30 E$^{-9}$ |
| equiv. | 12.9 | 0.03 | | 1.0 |

The RBDCL is allowed to equilibrate in the dark for 72 hours, a period of time shown to be sufficient for equilibrium to be reached with solution phase library monomers by HPLC. After RBDCL equilibration, the contents of the reaction vessel (unbound solution phase RBDCL constituents and unbound labeled target) are drained, and the resin beads are washed repeatedly with buffer and imaged under a fluorescent microscope with appropriate filters. (As exemplified by subsequent Examples, the washing procedure and imaging exposure time of each individual system should be adjusted so only a few beads fluoresce.)

Once fluorescent beads from the library screen are selected (FIG. 2), they are spatially segregated and subjected to photolysis (to break the photolabile linker) and then the dimeric compounds are identified by electrospray ionization mass spectrometry. While the Cys-StBu resin immobilized monomer is the most prevalent species on the individual selected bead, and as such is the most easily identified, the identity of selected "hit" Cys-StBu monomer RBDCL constituents allows for a starting point to deconvolute the identity of RBDCL selected disulfide ligands. For example, if three Cys-StBu monomers (1, 2, and 3) are identified by mass spectometry, then only combinations of these three monomers would produce the selected disulfide ligands (9 possible compounds). To rank the affinity of the possible disulfide ligands two routes can be pursued: a secondary fluorescence based resin assay, or independent synthesis of all possible selected disulfide compounds followed by binding analysis.

Both of these approaches are described in the following Examples, where the library was screened against two biomedically important RNA sequences: a RNA stemloop involved in the HIV-1 frameshift process, and $(CUG)_n$ repeat RNA involved in the pathogenesis of myotonic dystrophy type 1. Importantly, as is shown in the following Examples, screening the RBDCL produced a unique ligand, or set of ligands, for each RNA target.

Example 3

Identification of Selective Small-Molecule Ligands for HIV-1 Frameshift-Inducing Stem-Loop RNA from the 11,325 Member Resin Bound Dynamic Combinatorial Library Using the library generated in Example 1, the library was screened against several Cy-3 labeled stem-loop nucleic acid molecules, including the HIV-1 frameshift-inducing stem-loop RNA.

In addition to the HIV-1 frameshift-inducing stem-loop RNA (GGCCUUCCCACAAGGGAAGGCC, SEQ ID NO:1), several control sequences were used during affinity binding assays, including an analogous DNA sequence (GGCCTTCCCACAAGGGAAGGCC, SEQ ID NO:2), an RNA control bearing a differing stem-loop (UAGUCU-UCGUAGACUA, SEQ ID NO:3), and an RNA molecule bearing an identical stem but an altered loop region (GGC-CUUCCCCACC GGGAAGGCC, SEQ ID NO:4). The secondary structure of these nucleic acid molecules is shown in FIGS. 7B-E. The RNA and DNA were purchased from Integrated DNA Technologies (≥95% purity by HPLC).

Before screening the library against the HIV-1 stem-loop RNA target, an assessment was first made as to whether the nucleic acid molecules will degrade over the course of the screening procedure. This was carried out by Dynamic Light Scattering (DLS) analysis using a DynaPro™ instrument and the same phosphate buffer used for subsequent library screening. DLS data (1 hour) showed a single species accounting for 98.1% of scatter, suggesting a monodisperse solution. This species showed a hydrodynamic radius ($R_H$) of 1.82 nm (18.2 Å) in size. DLS data (72 hours) showed a single species accounting for 95.1% of scatter, suggesting a monodisperse solution. This species showed a hydrodynamic radius ($R_H$) of 1.79 nm (17.9 Å) in size. These data are in agreement with the NMR structure of this sequence (Staple et al., "Solution Structure and Thermodynamic Investigation of the HIV-1 Frameshift Inducing Element," *J. Mol. Biol.* 349:1011-1023 (2005), which is hereby incorporated by reference in its entirety) and confirms that the RNA will not degrade over the course of the screening procedure.

Graphical analysis of Surface Plasmon Resonance (SPR) data was carried out using DeltaGraph (Rockware Inc.). SPR analysis was conducted on a Reichert SR7000 refractometer using Reichert gold sensor slides that consist of a mixed self-assembled monolayer of thiol-PEG-alcohols and thio-PEG-carboxylic acids (~9:1; PEG=polyethylene glycol). Amine functionalized small molecules were attached by NBT/EDC coupling to the carboxy termini of the surface. After activating the monolayer, molecules were covalently attached through the addition of a 1 mg/mL solution of molecule in a sodium acetate buffer (20 mM, pH=5.5). Unreacted activated esters were quenched through the addition of ethanolamine. A flow rate of 10 µL/min and injection volumes of 150 µL was used throughout the experiment. RNA solutions were made to be 15.3 nM, 62.5 nM, 250 nM, 500 nM, 1 µM, 2 µM, 10 µM, and 50 µM. RNA was added from the lowest concentration to the highest concentration over the course of the SPR experiment. Data analysis was performed using Scrubber software (Reichert) by monitoring bound RNA via the change in µRIU after dissociation with PBS. These values were plotted using DeltaGraph and fitted using a logistic fit (Equation 1). The monolayer was regenerated through the addition of a 10 mM glycine solution, pH=2.0, followed by a washing step with PBS.

Logistic Curve Fit          Equation 1

$$y = \frac{A+B}{1+\left(\frac{x}{x_0}\right)^p} + B$$

where; A=min; b=max; x=[RNA]; $x_o$=IQ; p=power (1.0)

NMR spectral data were processed and analyzed using MestReC v. 4.4.1.0 (Mestrelab Research).

Figure 2:
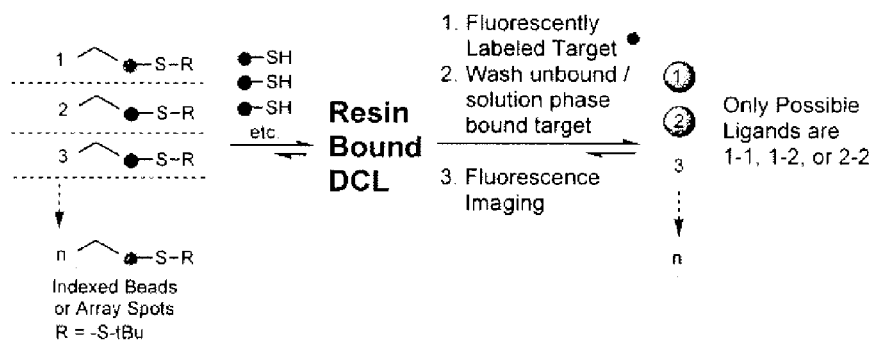
FIG. 2 is a schematic showing RBDCC, in which a heterogeneous mixture of solution phase building blocks was equilibrated with solid phase building blocks and fluorescently labeled target nucleic acid in buffer.

The RBDCC experiments were performed according to the scheme set forth in FIG. 2. First, as a control, 450 beads (150 of each size, 3 beads/compound, 387 nmol total) were placed in a 1.5 ml solid phase reaction vessel. To this was added a 1 ml solution of 1 µM RNA-Cy3 in phosphate buffer. This solution was agitated for 3 hours on a LabQuake™ rotator. After such time, the solution was drained by vacuum and washed three times with buffer (1 ml, 1 min. each). After washing, the resin was suspended in 2 ml buffer and placed in a Petri dish. Subsequent examination of the resin under a fluorescence microscope equipped with a Cy3 filter showed that no resin beads bearing single library building blocks bound the RNA with significant affinity under the conditions used.

Next, RBDCC experiments were run in quadruplet. A heterogeneous mixture of solution phase building blocks (30 µM based on average molecular weight) was equilibrated with solid phase building blocks (450 beads, 150 each size, 387 µM total) and fluorescently labeled stem-loop RNA (1 µM) in buffer (see Table 3, Example 2 above). Solution phase components were prepared in a dimethylsulfoxide ("DMSO") solution (0.1% DMSO final concentration). Libraries were equilibrated in quadruplet for 72 hours, a period of time shown by HPLC to be sufficient for equilibrium to be reached. After such time, the solution was removed from 1 of the 4 experiments and the resin was washed with buffer, plated with 2 ml buffer, and analyzed by fluorescence microscopy as described above. Using a washing scheme and exposure time identical to the control experiment described above resulted in a significant number of resin bearing similar fluorescence intensities. Ideally, only the highest affinity ligands are selected. Therefore, washing schemes as well as the exposure time on the microscope were adjusted while analyzing experiments 2 and 3 such that only a few resin beads were observed to exhibit fluorescence. In the fourth and final analysis, the strictest washing protocol was used (4 times, 90 seconds per wash), and an exposure time of 50 msec. was used.

Figure 3:
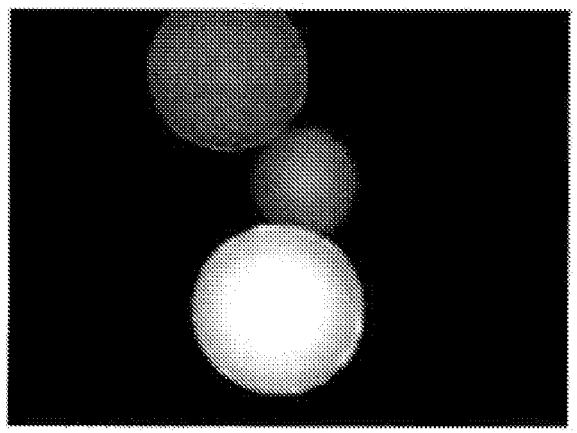
FIG. 3 is an image showing an example of selection of high-affinity ligands from a mixture by fluorescence.
Figure 4:
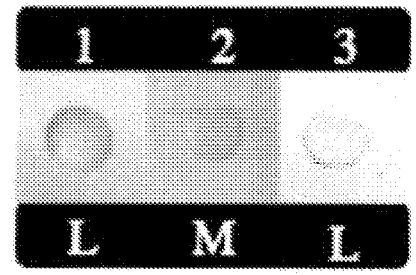
FIG. 4 is an image showing identification of cysteine position in structures on selected resin beads by size differentiation. "L" refers to large resin beads and "M" refers to medium resin beads.
Figure 5A:
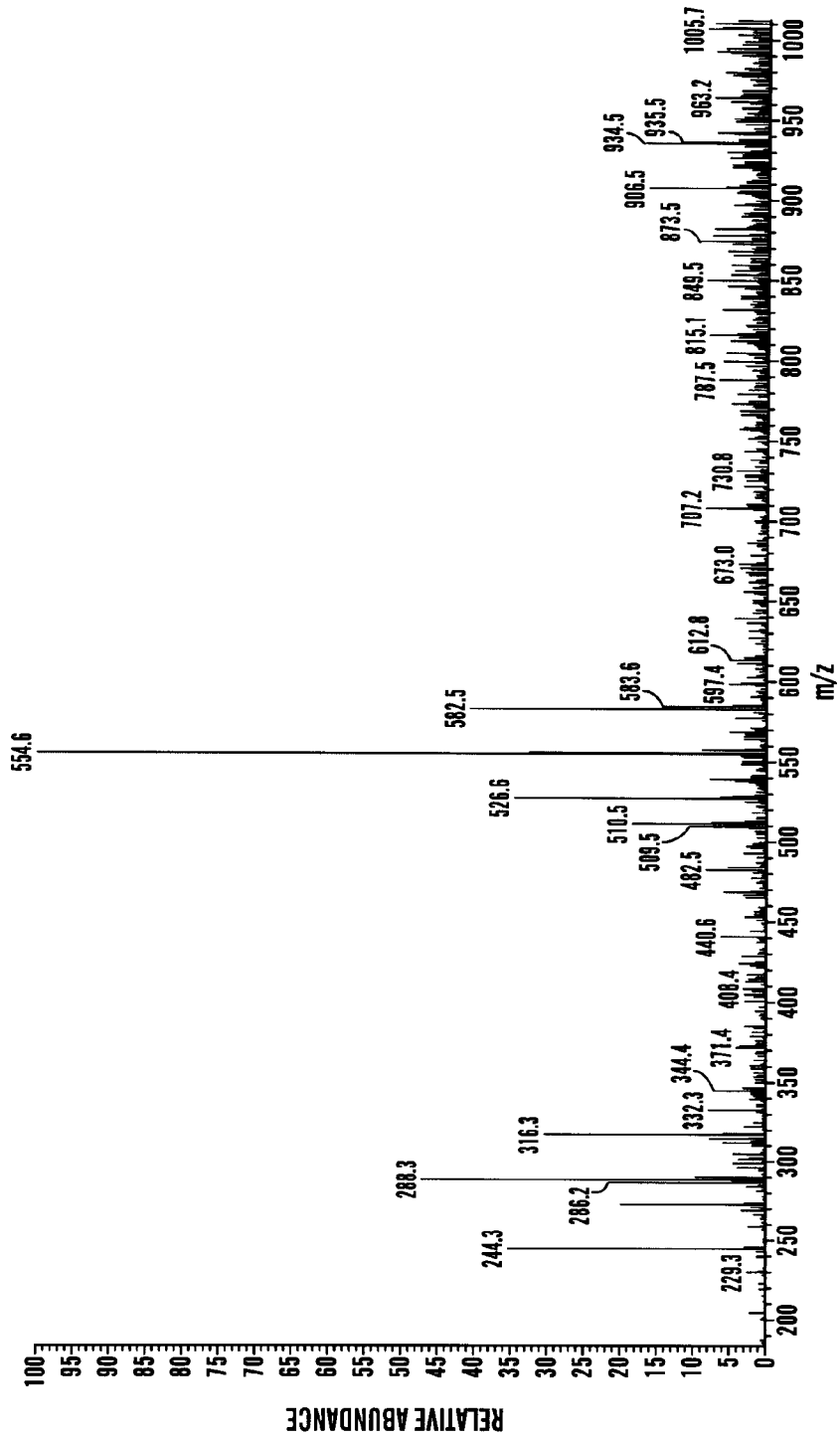
FIGS. 5A-D are graphs showing mass spectrometry data identifying building blocks which participate in the synthesis of high-affinity ligands, including cleavage of resin bearing photo-labile linker (3-amino-3-(2-nitrophenyl) ("Anp")) (FIG. 5A), cleavage of the 1$^{st}$ bead selected for in the RBDCC experiment ((M+1)=749.3; (M+Na)=771.3) (FIG. 5B), cleavage of the 2$^{nd}$ bead selected for in the RBDCC experiment ((M+1)=640.2; (M+Na)=662.3) (FIG. 5C), and cleavage of the 2$^{nd}$ bead selected for in the RBDCC experiment ((M+1)=741.3; (M+Na)=763.1; (M+2/2)=371.4) (FIG. 5D).
Figure 5B:
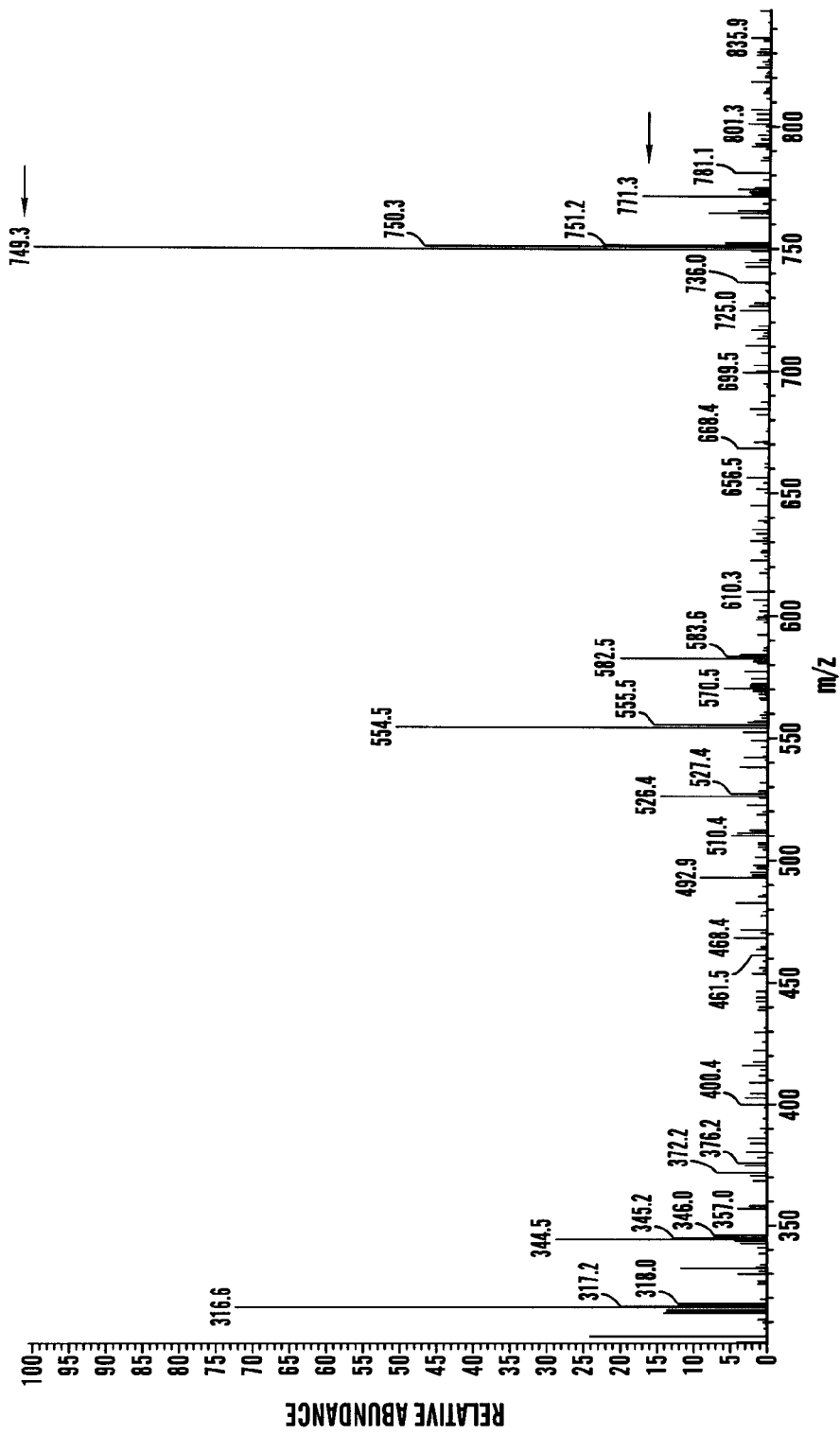
Figure 5C:
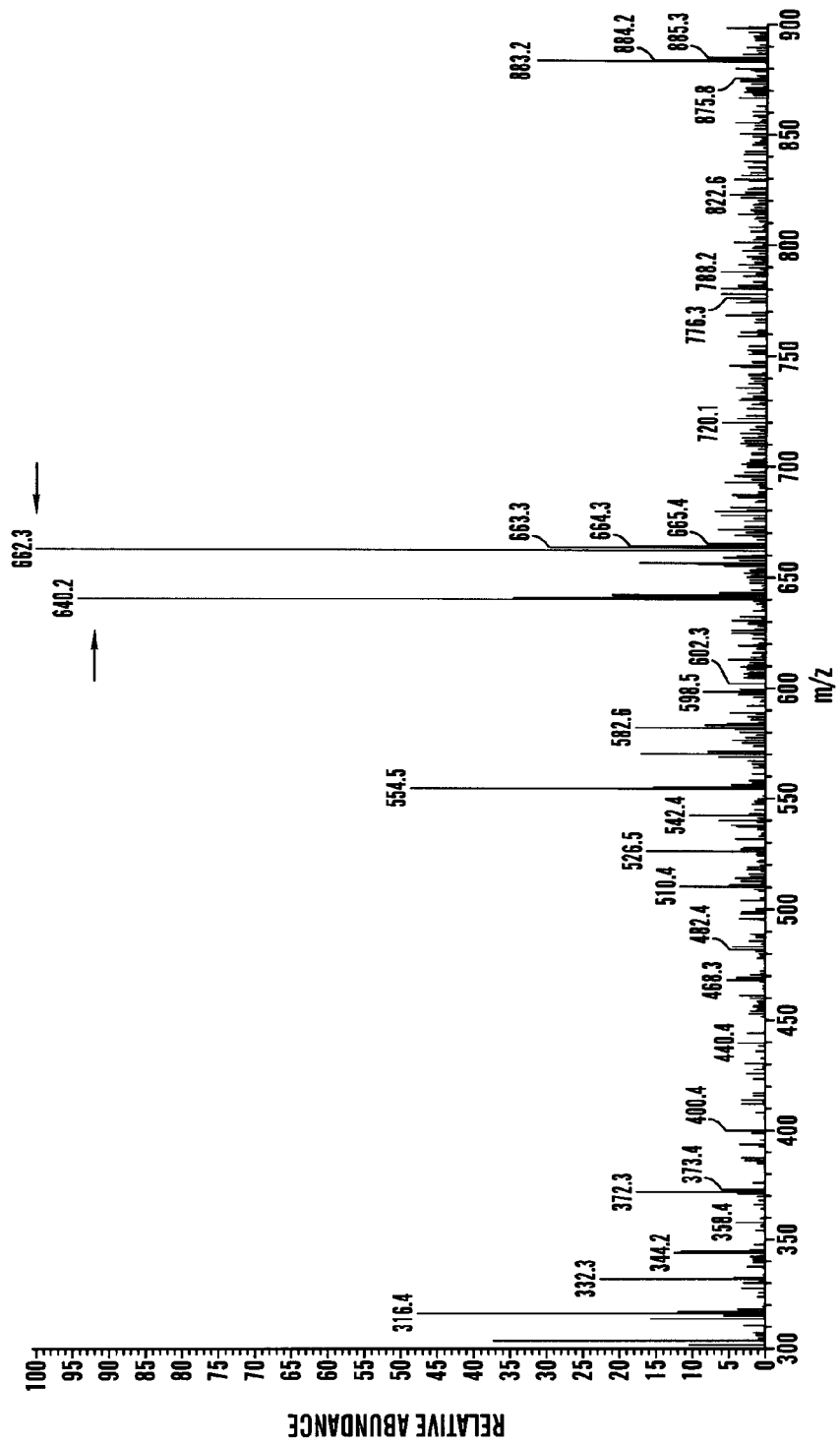
Figure 5D:
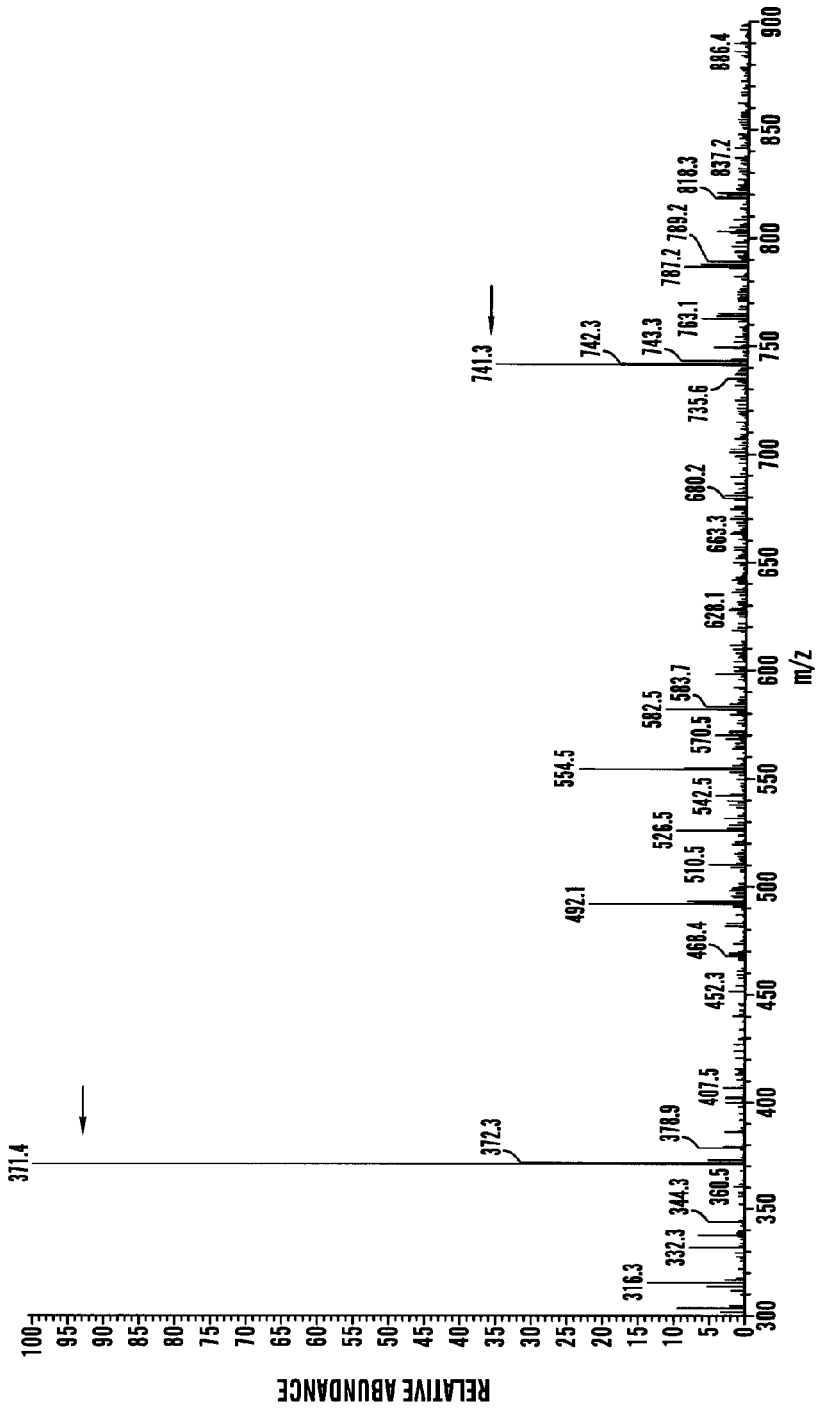

Under these conditions, three beads were selected as exhibiting significant fluorescence (FIG. 3). These beads were removed via syringe, and washed further to remove as much of the bound RNA as possible (5×DMF, 5× tetrahydrofuran ("THF"), 5× acetonitrile). Before cleavage, selected resin beads were measured to identify the position of the cysteine residue within the building block (FIG. 4). Finally, the selected beads were cleaved by photolysis (365 nm) in eppendorf tubes containing 100 μL acetonitrile:methanol (4:1) for 24 hours. The resulting solution was analyzed by mass spectrometry to identify unreacted thio-S-tBu monomers, which where the highest population species on the resin and, therefore, the most easily detected. Mass spectrometry was performed at the University of Buffalo mass spectrometry facility (FIGS. 5A-D). Data was obtained on a ThermoFinnigan MAT 95 XL spectrometer using electrospray ionization.

These data correspond to building block monomers 1, 2, and 3 shown below:

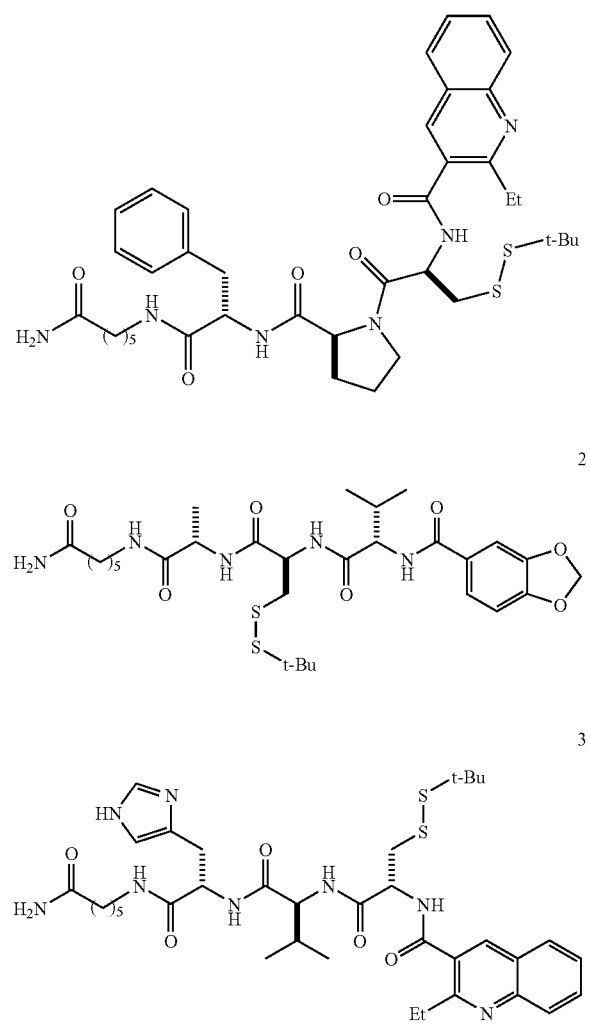

From these building blocks, the highest affinity ligand(s) were next determined. 1, 2, and 3 were individually synthesized on TentaGel (0.86 nmol/bead), and equilibrated as described above in separate vessels containing only 1, 2, or 3 solution phase monomers and 500 nM RNA stem-loop, half the concentration used in the initial screen. After 72 hours the resin was washed in a manner identical to the conditions of screen number 4 (i.e., the highest stringency screen) and analyzed by fluorescence microscopy (50 msec. exposure) (see FIGS. 6A-I). As shown in FIGS. 6A and 6C, dimers 1-1 and 1-3, respectively, were found to have the highest affinity for the RNA stem-loop. Other dimers showing some affinity for the RNA stem-loop include dimers 2-3 and 3-3, although the degree of fluorescence intensity exhibited (i.e., amount of target bound) is relatively low compared to dimers 1-1 and 1-3 (compare FIGS. 6F, 6I versus 6A, 6C).

Interestingly, while compound 1-3 exhibits high levels of fluorescence intensity, 3-1 did not (compare FIG. 6C versus 6G). This highlights an important feature of RBDCC—the ability to readily identify highest affinity compounds due to competition between solid phase and solution phase components. Thus, if the highest affinity dimer can be formed on resin, binding will occur on this phase and one will see high bead fluorescence at the end of the screen. Based on this analysis, the results shown in FIGS. 6A-I led to the expectation that 1-1 would have a higher affinity than 1-3 for the RNA stem-loop.

To confirm this hypothesis, dissociation constants ($K_d$) were measured for dimers 1-1 and 1-3 by SPR (FIG. 7A) (Whitney et al., "Templated Ligand Assembly by Using G-quadruplex DNA and Dynamic Covalent Chemistry," *Angew. Chem. Int. Ed.* 43:1143-1146 (2004); Lacy et al., "Influence of a Terminal Formamido Group on the Sequence Recognition of DNA by Polyamides," *J. Am. Chem. Soc.* 124:2153-2163 (2002); Carrasco et al., "DNA Sequence Recognition by the Indolocarbazole Antitumor Antibiotic AT2433-B1 and Its Diastereoisomer," *Nucleic Acids Res.* 30:1774-1781 (2002), each of which is hereby incorporated by reference in its entirety). Compound 1-1 was found to have an affinity of 1.9 μM to the HIV-1 frameshift regulatory RNA sequence (Seq I, FIG. 7B, SEQ ID NO:1), while the affinity of 1-3 was determined to be >90 μM.

Specificity was assessed by measuring the affinity of 1-1 to three other oligonucleotides: the DNA sequence homologous to I (Seq II, FIG. 7C, SEQ ID NO:2), the alternate RNA stem-loop (Seq III, FIG. 7D, SEQ ID NO:3) (Karan et al., "RNA-Selective Coordination Complexes Identified via Dynamic Combinatorial Chemistry," *J. Am. Chem. Soc.* 123: 7455-7456 (2001), which is hereby incorporated by reference in its entirety), and an RNA stem loop with an altered loop sequence (Seq IV, FIG. 7E, SEQ ID NO:4). As expected, 1-1 showed no measurable affinity for sequences II and III and only marginal (>90 μM) affinity for sequence IV. These results confirm that of the compounds selected, 1-1 has the highest affinity for the HIV-1 frame-shifting regulatory RNA sequence and also that the recognition process is exceptionally sequence-selective.

In conclusion, the RBDCC method has been used to generate and screen an 11,325 member DCL. While this library was small enough to exclude mass overlap of library building blocks, much larger RBDCLs with mass overlap could be deconvoluted using resin-bound tagging schemes employed in this Example. From this screen, several compounds that bind the HIV-1 frameshift-inducing stem loop were identified. One of these was determined to be a selective and high-affinity ligand for the HIV-1 frameshift-inducing stem loop. Based on these results, it is expected that dimers 1-1 and 1-3 will be capable of inhibiting the activity of the HIV-1 frameshift-inducing stem loop.

Example 4

Preparation and Spectral Analysis of Dimers 1-1 and 1-3

Dimers 1-1 and 1-3 were prepared as described below.

Monomers 1 and 3 were prepared as described in the preceding Examples on 3 grams Wang resin using Cys(Trt)-OH except that the carboxyl terminus was capped with 1,3-dipropyl amine. After synthesis was complete, the trityl group was removed through the addition of 2% TFA/DCM for 30 minutes. This was repeated twice to assure removal of this group. Mass spectrometry analysis of the resulting solution showed the presence of the trityl species and not cleaved monomer. After washing the resin, it was split into two 500 mg aliquots. A 2 g aliquot of resin (2.0 mmol) was cleaved by addition of 50% TFA/1% TES/DCM for 1 hour, and ether precipitated as described previously. To 100 mg of Wang monomeric resin (0.1 mmol, 1 eq.) was added 5 ml of a 0.2 M, 0.1% DMSO-phosphate buffer solution (1.0 mmol, 10 eq.) of either monomer 1 or 3. This solution was agitated for 24 hours, drained, and a fresh solution of monomer was added and agitated for an additional 24 hours. After such time the resin was washed, cleaved, and ether precipitated as described previously. The precipitate (an off-white powder) was dried by lyophilization and analyzed.

The structures of 1-1 and 1-3 are shown below:

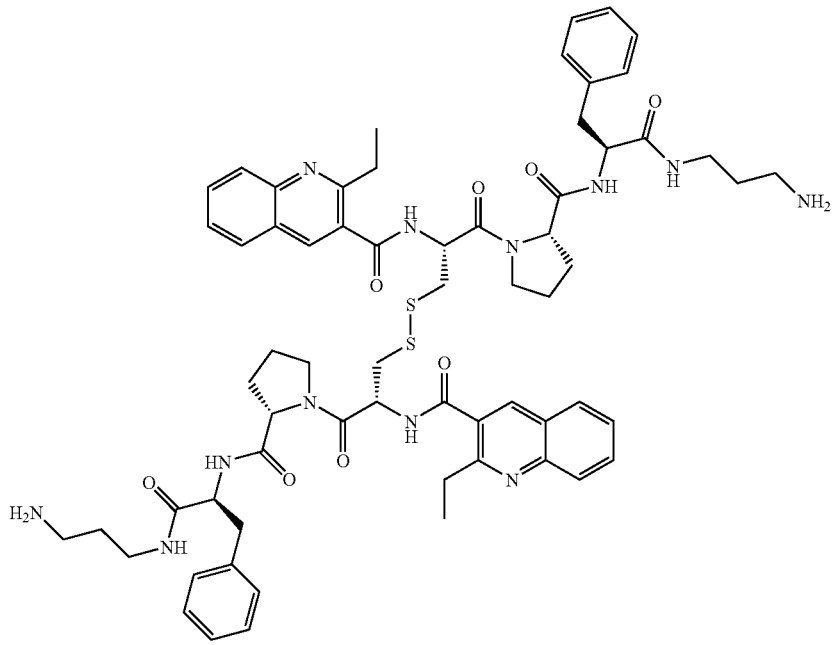

1-1

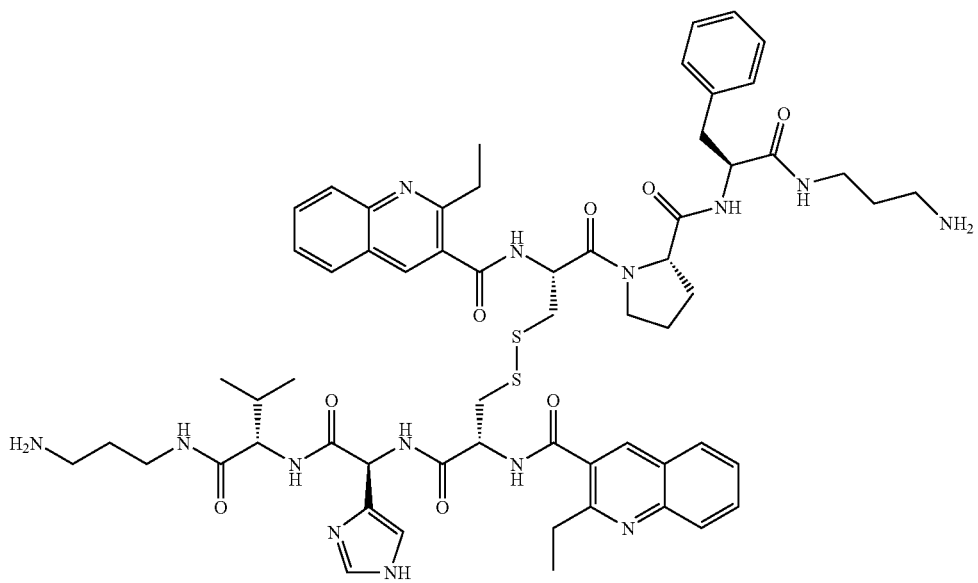

1-3

Figure 8A:
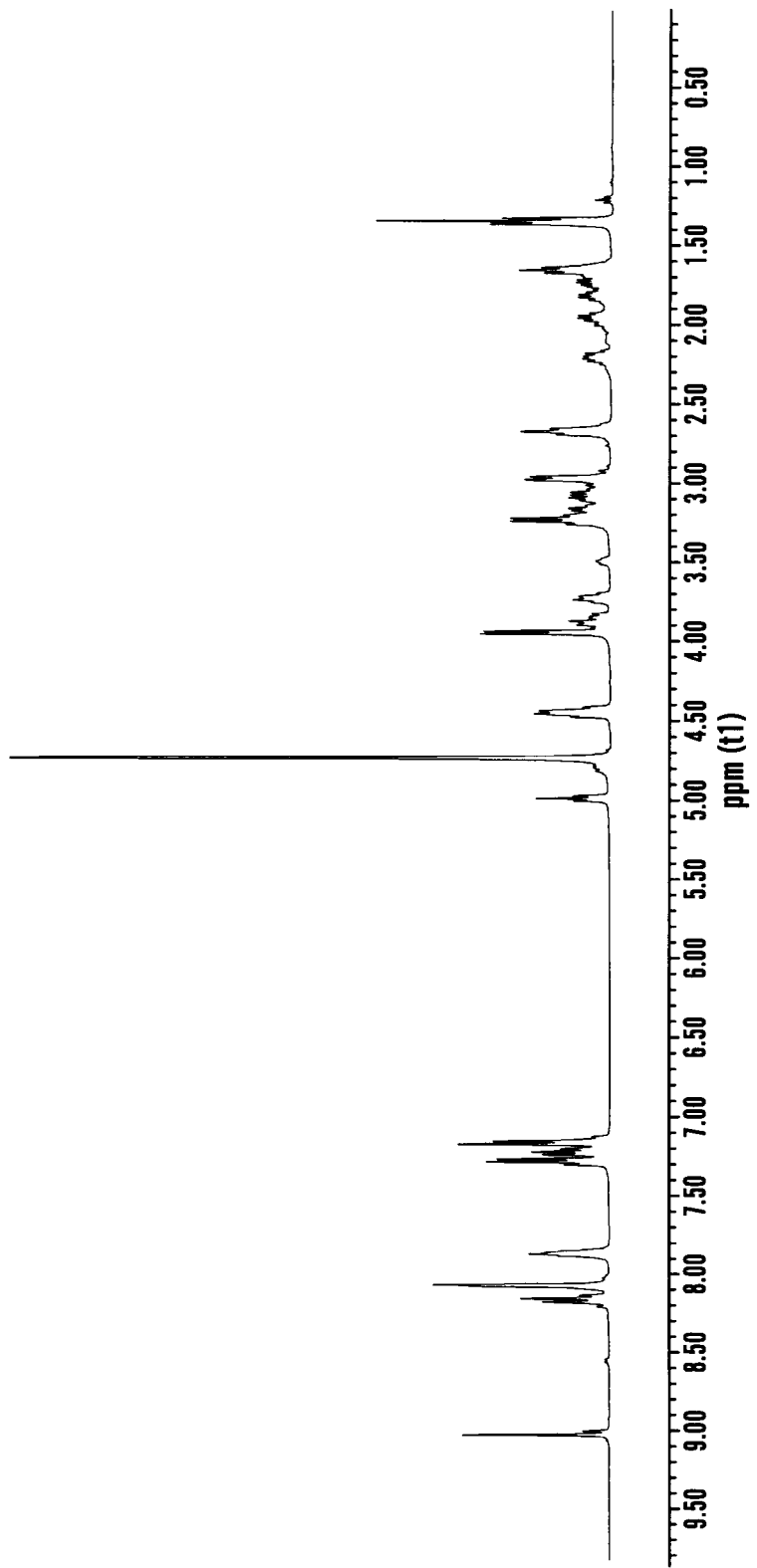
FIGS. 8A-C are graphs showing mass spectrometry data for the dimer compound 1-1.
Figure 8B:
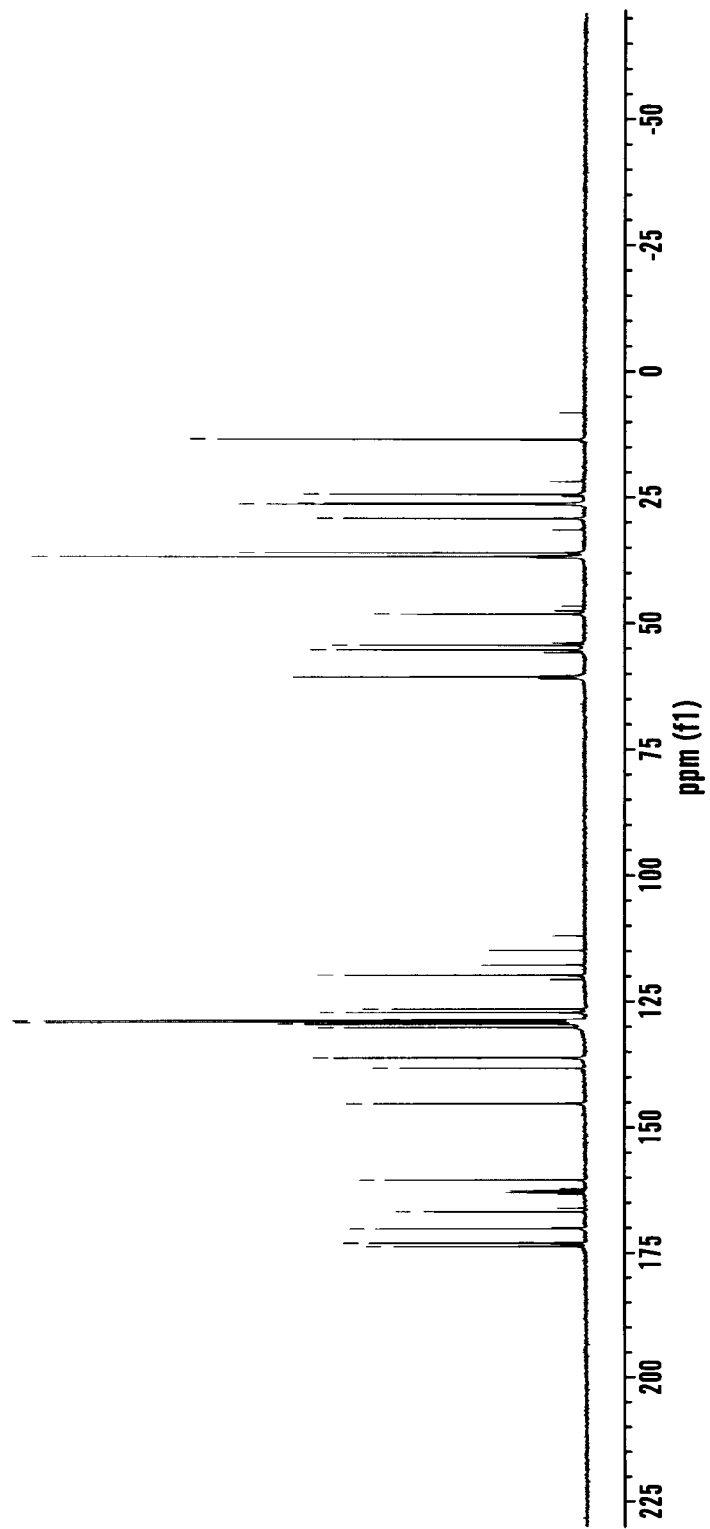
Figure 8C:
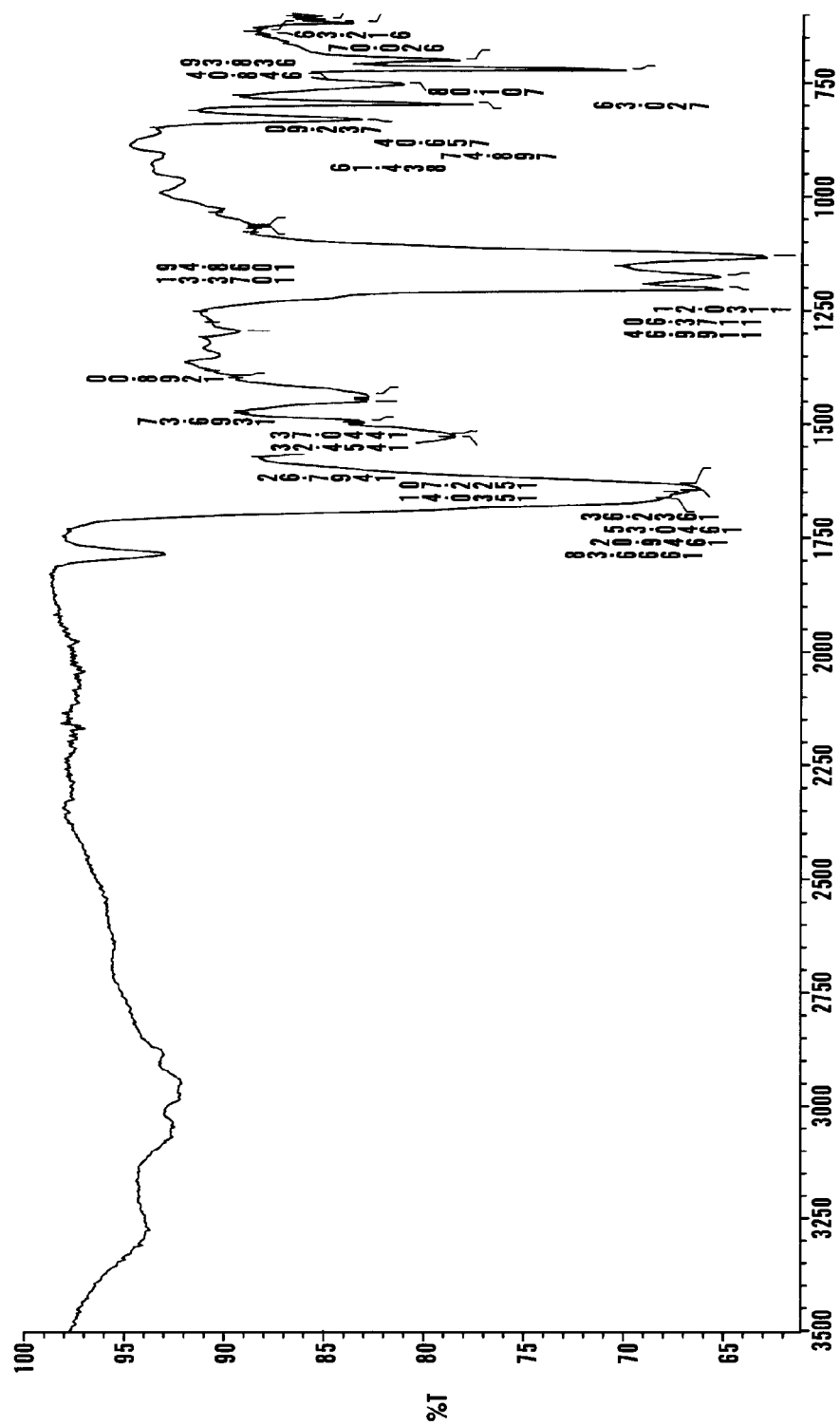

Due to cleavage conditions from the solid support, compounds exhibit peaks in the $^{13}$C spectra from TFA (163 ppm (q, J=155 Hz), 116 ppm (q, J=1125 Hz). These peaks are not listed in the spectral analysis of FIGS. 8A-C.

The spectral data (IR, $^1$H, $^{13}$C, HRMS) for dimer compound 1-1 (FIGS. 8A-C) is as follows: $^1$H (400 MHz, CD$_3$OD): δ: 9.02 (1H, s); 8.18-8.17 (1H, m); 8.11-8.08 (2H, m); 7.88-7.86 (1H, m); 7.28 (2H, t, J=8 Hz); 7.24 (1H, t, J=6 Hz); 7.16 (2H, d, J=8 Hz); 4.98 (1H, t, J=6 Hz); 4.47-4.41 (1H, m); 3.94 (2H, d, J=6 Hz); 3.89-3.83 (1H, m); 3.75-3.64 (1H, m); 3.23 (2H, q, J=8 Hz); 2.96 (2H, d, J=8 Hz); 2.67 (2H, t, J=6 Hz); 2.23-2.18 (1H, m); 2.05-1.93 (1H, m); 1.86-1.79 (1H, m); 1.76-1.70 (1H, m); 1.65 (2H, t, J=7 Hz); 1.35 (3H, t, J=8 Hz). $^{13}$C (75 MHz, CD$_3$OD): δ: 173.6, 172.9, 172.8, 170.0, 166.7, 160.4, 145.2, 138.1, 136.1, 130.1, 129.4, 129.0, 128.9, 128.7, 128.5, 127.1, 126.4, 119.7, 60.6, 60.5, 55.2, 54.3, 48.1, 36.7, 35.9, 29.2, 26.3, 26.1, 24.4, 13.5. IR (neat): cm$^{-1}$: 1761, 1666, 1640, 1530, 1522, 1440, 1286, 1199, 1173, 1159, 883, 788, 756, 720, 701, HRMS m/z calculated for (M$^+$+H); 1207.5585. found: 1207.5593.

Figure 9A:
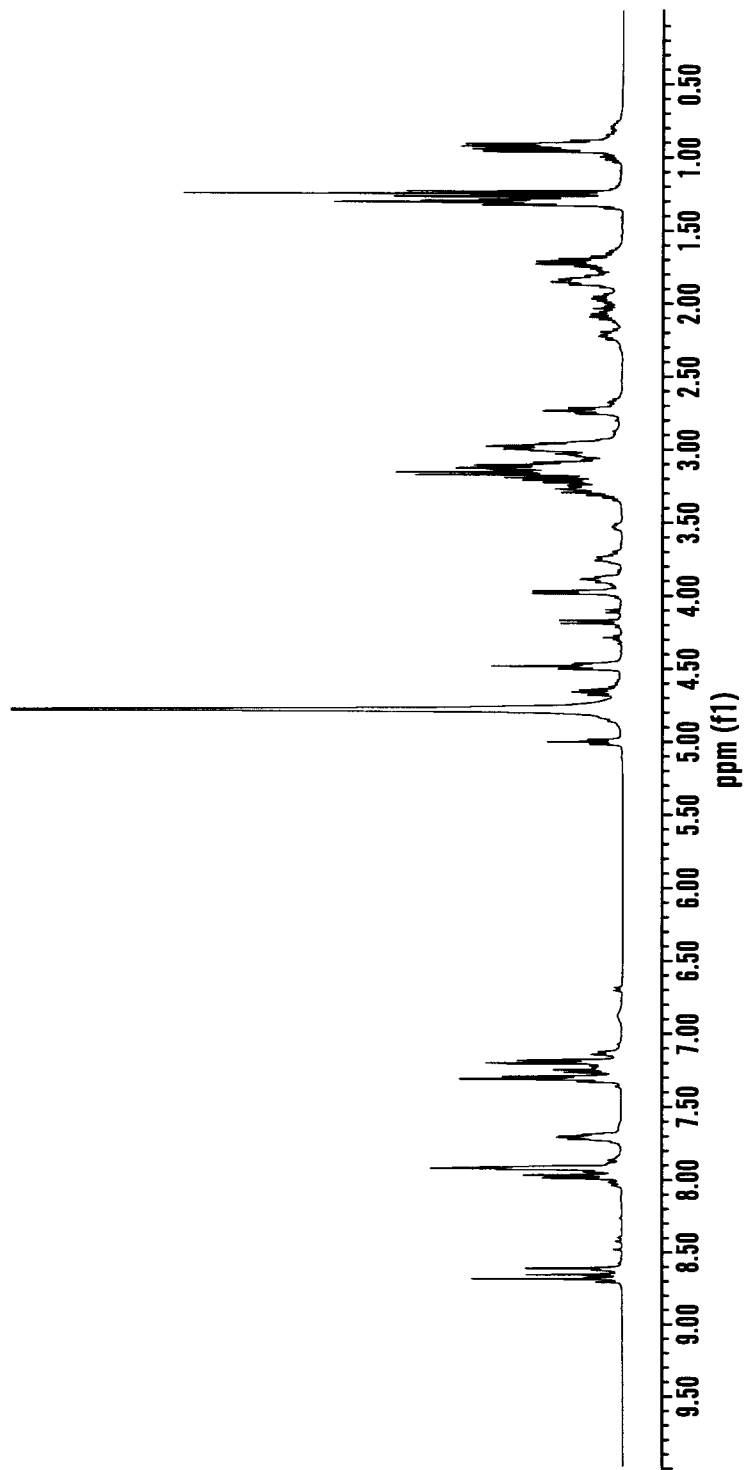
FIGS. 9A-C are graphs showing mass spectrometry data for the dimer compound 1-3.
Figure 9B:
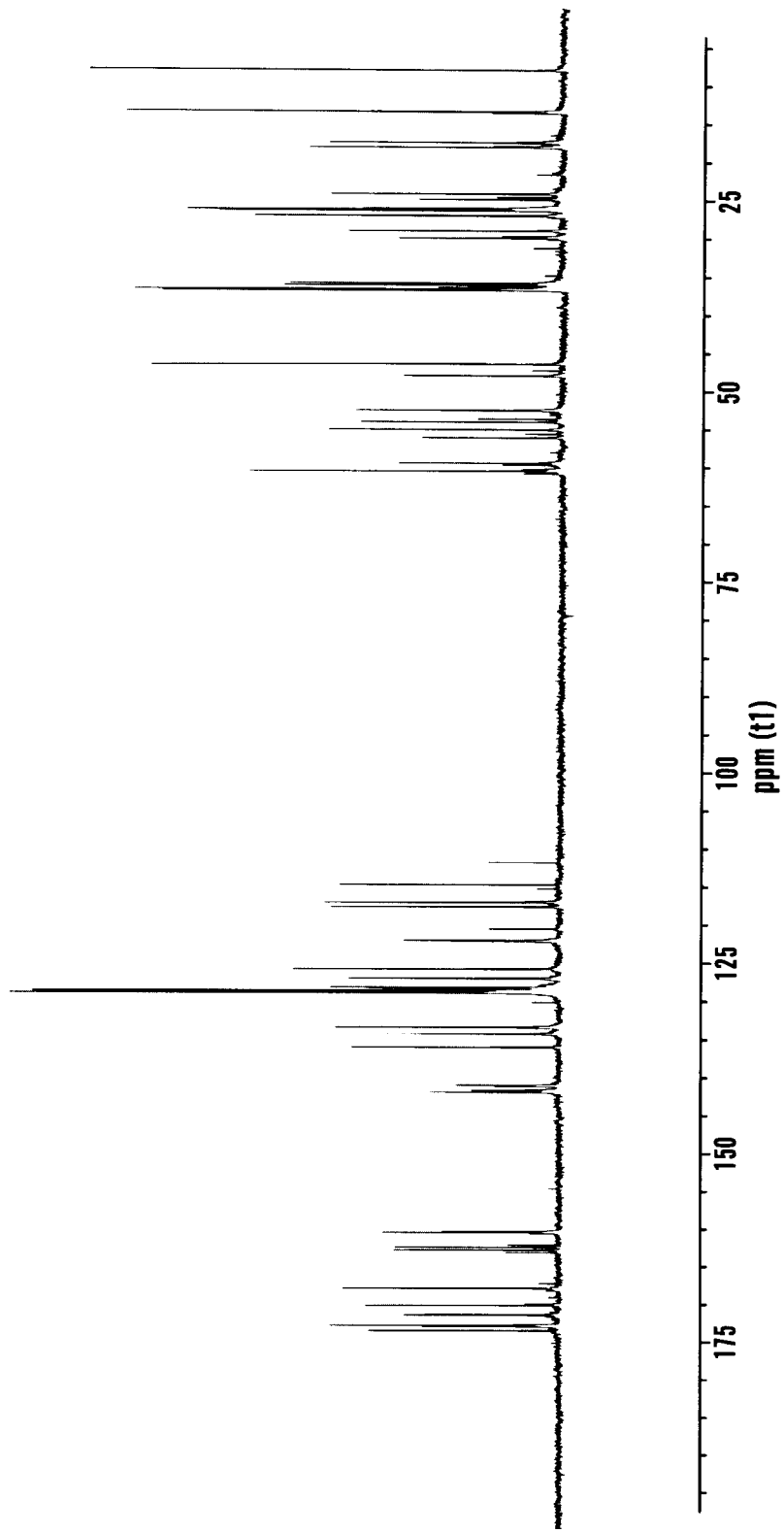
Figure 9C:
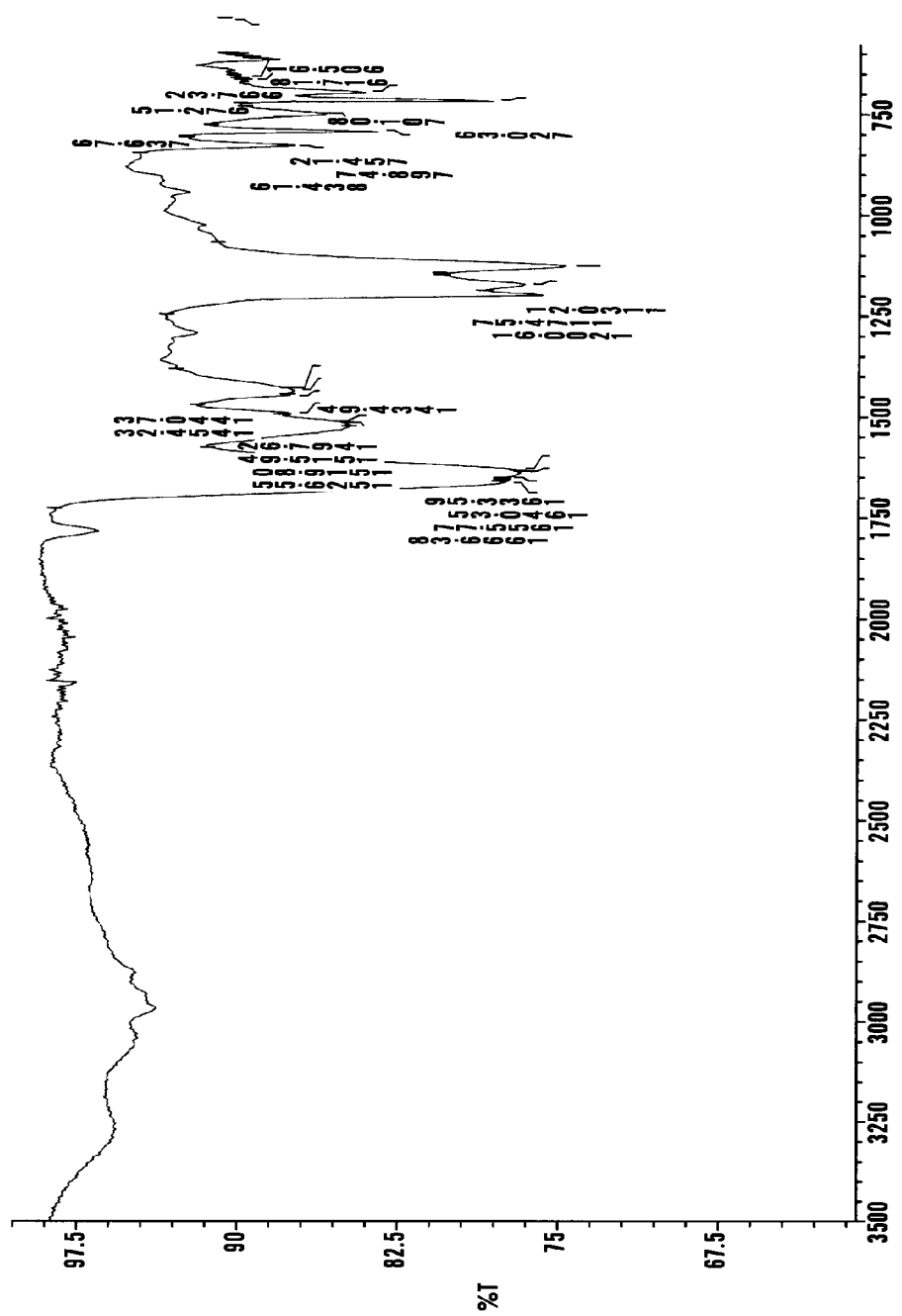

The spectral data (IR, $^1$H, $^{13}$C, HRMS) for dimer compound 1-3 (FIGS. 9A-C) is as follows: IR (neat): cm$^{-1}$; 1760, 1640, 1519, 1454, 1201, 1175, 1130, 834, 798, 754, 720, 701 $^1$H NMR (400 MHz, D$_2$O) δ: 8.69 (1H, s); 8.67 (1H, s); 8.62 (1H, d, J=1.2 Hz); 8.00 (1H, s); 7.98 (1H, s); 7.93 (3H, t, J=2.8 Hz) 7.72 (2H, m); 7.75-7.68 (2H, m); 7.34-7.30 (3H, m); 7.22-7.18 (3H, m); 7.28-7.26 (1H, m); 5.01 (1H, t, J=6.4 Hz); 4.69-4.65 (1H, m); 4.51-4.47 (2H, m); 4.18 (1H, d, J=7.4 Hz); 3.98 (2H, d, J=7.2 Hz); 3.92-3.88 (1H, m); 3.78-3.72 (1H, m); 3.33-3.25 (2H, m); 3.25-3.19 (2H, m); 3.19-3.09 (7H, m); 3.07-2.93 (5H, m); 2.74 (2H, t, J=6.8 Hz); 2.27-2.17 (1H, m); 2.12-2.05 (1H, m); 2.01-1.94 (1H, m); 1.90-1.81 (3H, m); 1.79-1.68 (3H, m); 1.34-1.28 (4H, m); 1.26 (3H, t, J=7.2); 0.97-0.91 (4H, m). $^{13}$C NMR (75 MHz, D$_2$O) δ: 173.6, 173.0, 172.9, 171.5, 171.4, 171.3, 170.2, 167.9, 160.5, 160.4, 142.0, 141.8, 141.2, 141.1, 136.1, 134.4, 134.3, 133.5, 129.0, 128.9, 128.7, 128.4, 128.3, 127.1, 125.9, 122.2, 122.1, 117.7, 60.6, 59.6, 56.2, 55.2, 54.1, 53.8, 52.6, 48.1, 46.6, 36.9, 36.7, 36.5, 36.2, 35.9, 30.1, 29.1, 27.2, 26.5, 26.4, 26.2, 25.0, 24.3, 18.2, 17.6, 13.6, 8.1. HRMS m/z calcd for (M$^+$+H); 1199.5641. found: 1199.5634.

Example 5

Synthesis of Dicarba Analogs of Dimer 1-1

Two cis-acting elements in viral mRNA are responsible for the −1 ribosomal frameshift. In the RNA sequence shown in FIG. 10 (SEQ ID NO:5), the heptameric slippery sequence (UUUUUUA, nts 1-7) is where the frameshift takes place, and a downstream stimulatory signal is present in the form of an upper stem-loop (nts 18-29) (Dulude et al., "Characterization of the Frameshift Stimulatory Signal Controlling a Programmed −1 Ribosomal Frameshift in the Human Immunodeficiency Virus Type 1," *Nucleic Acids Res.* 30:5094-5102 (2002); Gaudin et al., "Structure of the RNA Signal Essential for Translational Frameshifting in HIV-1," *J. Mol. Biol.* 349: 1024-1035 (2005); Staple et al., "Solution Structure and Thermodynamic Investigation of the HIV-1 Frameshift Inducing Element," *J. Mol. Biol.* 349:1011-1023 (2005), each of which is hereby incorporated by reference in its entirety). Small molecules targeting the regulatory stem-loop structure can serve as potential inhibitors of viral replication.

As demonstrated in the previous Examples, dimer 1-1 was shown to be a selective and high affinity ligand for the frameshift-inducing RNA stem-loop as measured by SPR. This molecule, therefore, serves as an important lead for the development of additional high affinity ligands for the frameshift-inducing RNA stem-loop of HIV-1.

The disulfide bridge in this molecule, due to its reversible nature, was helpful for generating structural diversity and dynamic screening in the RBDCC library. However, it's susceptibility to biological environment (pH, enzymes) may present an obstacle in further biological investigation on this class of molecules. It is known that in most of the biological peptides, disulfide linkage serves only a skeletal or structural role and replacing it with isosteric functionalities like thioether (—S—CH$_2$—) or all carbon (olefin, —CH$_2$—CH$_2$—) enhances biostability of the molecule without affecting it's function (Fotouhi et al., "Cyclic Thio ether Peptide Mimetics as VCAM-VLA-4 Antagonists," *Bioorg. Med. Chem. Lett.* 10:1167-1169 (2000); Stymiest et al., "Synthesis of Biologically Active Dicarba Analogues of the Peptide Hormone Oxytocin Using Ring-closing Metathesis," *Org. Lett.* 5:47-49 (2003); Berezowska et al., "Dicarba Analogues of the Cyclic Enkephalin Peptides H-Tyr-c[D-Cys-Gly-Phe-D(or L)-Cys] NH (2) Retain High Opioid Activity," *J. Med. Chem.* 50:1414-1417 (2007); Mollica et al., "Synthesis of Stable and Potent Delta/mu Opioid Peptides: Analogues of H-Tyr-c[d-Cys-Gly-Phe-d-Cys]-OH by Ring-Closing Metathesis," *J. Med. Chem.* 50:3138-3142 (2007), each of which is hereby incorporated by reference in its entirety).

Figure 11:
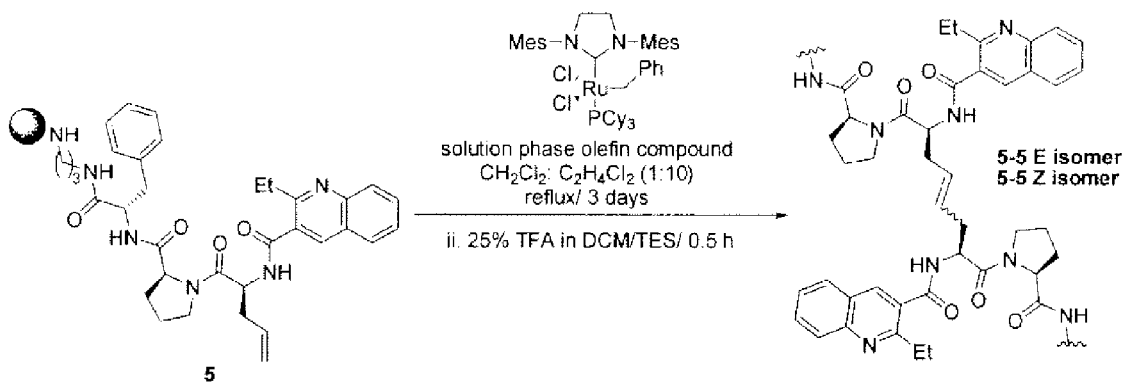
FIG. 11 illustrates Scheme 1 for the formation of dicarba analogs of the library disulfide dimers.

To examine the effect of isosteric substitution of the disulfide linkage in 1-1, its dicarba analogs (5-5 E and 5-5 Z) were synthesized (Scheme 1, FIG. 11) and their binding affinity for the HIV-1 frameshift-inducing RNA stem-loop was measured by fluorescence spectroscopy.

Ruthenium-catalyzed olefin metathesis is an attractive and powerful tool for the formation of carbon-carbon double bonds (Hoveyda et al., "The Remarkable Metal-catalysed Olefin Metathesis Reaction," *Nature* 450:243-251 (2007), which is hereby incorporated by reference in its entirety). Grubbs' catalysts (1$^{st}$ and 2$^{nd}$ generation) have been previously used in the synthesis of cyclic peptides via RCM (Stymiest et al., "Synthesis of Biologically Active Dicarba Analogues of the Peptide Hormone Oxytocin Using Ring-closing Metathesis," *Org. Lett.* 5:47-49 (2003); Berezowska et al., "Dicarba Analogues of the Cyclic Enkephalin Peptides H-Tyr-c[D-Cys-Gly-Phe-D(or L)-Cys]NH (2) Retain High Opioid Activity," *J. Med. Chem.* 50:1414-1417 (2007); Mollica et al., "Synthesis of Stable and Potent Delta/mu Opioid Peptides Analogues of H-Tyr-c[d-Cys-Gly-Phe-d-Cys]-OH by Ring-Closing Metathesis," *J. Med. Chem.* 50:3138-3142 (2007); Wels et al., "Synthesis of a Novel Potent Cyclic Peptide MC4-ligand by Ring-closing Metathesis," *Bioorg. Med. Chem.* 13:4221-4227 (2005); Stymiest et al., "Synthesis of Oxytocin Analogues with Replacement of Sulfur by Carbon Gives Potent Antagonists with Increased Stability," *J. Org. Chem.* 70:7799-7809 (2005), each of which is hereby incorporated by reference in its entirety). The metathesis reaction, when carried out on a resin-bound substrate, helps in obtaining a relatively pure product. A similar strategy was employed by synthesizing a linear peptide (5) on Wang resin using the standard Fmoc methodology. The olefin was introduced in the form of L-allylglycine, a substitute for the cystine amino acid in 1-1. The Fmoc-L-allylglycine used in the synthesis of 5 was prepared by the literature-reported method (Myers et al., "Greatly Simplified Procedures for the Synthesis of Alpha-amino Acids by the Direct Alkylation of Pseudoephedrine Glycinamide Hydrate," *J. Org. Chem.* 64:3322-3327 (1999); Ryan et al., "Convenient Access to Glutamic Acid Side Chain Homologues Compatible with Solid Phase Peptide Synthesis," *Org. Lett.* 7:4765-4767 (2005), each of which is hereby incorporated by reference in its entirety). Half the amount of resin bound peptide was then cleaved, using 30% TFA in dichloromethane in the presence of 1% triethoxysilane, to be used as a solution phase olefin counterpart for the metathesis reaction. Prior to the metathesis reaction, the other half of the peptide (resin bound) was washed with 0.8 M LiCl to prevent the complexation of Grubbs second generation catalyst with the amide bonds of the peptide (Derksen et al., "Antimicrobial Leucocin Analogues with a Disulfide Bridge Replaced by a Carbocycle or by Noncovalent Interactions of Allyl Glycine Residues," *J. Am. Chem. Soc.* 128:14252-14253 (2006), which is hereby incorporated by reference in its entirety). The metathesis was then carried out as shown in Scheme 1.

Resin bound 5 was synthesized using standard Fmoc methodology for peptide synthesis. Wang resin (1.0 g, 100-200 mesh, 1 mmol/g loading) was activated by it's reaction with 1,1'-carbonyl-di-imidazole (3.3 g, 10 mmol) in 12 mL of DMF, for 12 h on LabQuake™ rotator. The resin was then washed three times each with DMF, $CH_2Cl_2$, and DMF again, followed by reaction with 1,3-diamino propane (0.72 mL, 10 mmol) in DMF (12 mL), for another 12 h. The wash cycle was then repeated. The coupling of the first amino acid was carried out by adding Fmoc-L-Phe-OH (1.16 g, 3 mmol), HBTU (1.14 g, 3 mmol), and DIPEA (0.85 mL, 5 mmol) in 12 mL of DMF to the resin and rotating the reaction mixture for 1 h. The Fmoc deprotection was done using 20% piperidine in $CH_2Cl_2$ for 0.5 h followed by the wash cycle. Similarly, Fmoc-L-Pro-OH, Fmoc-L-allylglycine, and 2-Ethyl-quinoline-3-carboxylicacid were coupled to synthesize resin bound monomeric compound (5).

The resin was then split into two equal parts of 0.50 g. One part of resin was treated with 30% TFA in $CH_2Cl_2$ and 1% TEA for 0.5 h to obtain a cleaved product 5 (0.23 g) to be used as in solution olefin component for the metathesis reaction. The other part of the resin was dried in a dessicator under vacuum for 12 h and allowed to swell in dry $CH_2Cl_2$ (12 mL) for 20 min. The resin was then washed with $CH_2Cl_2$ (10 mL×3) followed by 0.8 M LiCl in DMF (10 mL) for 10 min. The resin was then washed with DMF (10 mL) and the 0.8 M LiCl wash was repeated for two more times. This was followed by washing the resin with dry and degassed 1,2-dichloroethane (10 mL) and then suspending the resin in the same solvent. To this suspension were added Grubbs $2^{nd}$ generation catalyst (0.14 g, 0.17 mmol) in 10 mL of 1,2-dichloroethane and the cleaved 5 (0.25 g, 0.42 mmol) in 20 mL of 1:4 mixture of $CH_2Cl_2$ and 1,2 dichloroethane and refluxed for 24 hours. The reaction was cooled to room temperature and additional amount of Grubbs $2^{nd}$ generation catalyst (0.07 g, 0.09 mmol) was added to the reaction mixture and refluxed for 24 hours. This cycle was repeated one more time. The reaction mixture was cooled to room temperature and filtered. The resin was then washed with $CH_2Cl_2$ (10 mL×3), DMF (10 mL×3) and suspended in 10 mL of DMF. DMSO (0.2 mL) was added to the suspension and rotated for 12 h. The resin was then washed and the product cleaved off the resin with 25% TFA in $CH_2Cl_2$ (10 mL) for 0.5 h to obtain a crude mixture of cis and trans olefins (0.25 g, 64%).

Cleavage of the resin bound metathesis adduct gave a mixture of olefin isomers (5-5 E and 5-5 Z) in 64% yield. The olefin isomers were separated by preparative RP-HPLC (30% acetonitrile in water with 0.1% TFA) to give the cis/trans isomer in 3:2 ratio.

Example 6

Screening of Dimers 5-5 E and 5-5 Z

The binding of dicarba analogs to the HIV-1 frameshift-inducing RNA was measured using fluorescence spectroscopy. Fluorescence titrations were performed on a Varian Cary eclipse fluorescence spectrophotometer using 1 cm path-length quartz fluorescence cell. The solution of Cy-3 labeled HIV-1 RNA stem-loop in PBS buffer (400 µL, 400 nM) was taken in the cell and excited with a wavelength of 550 nm. A PMT voltage of 715 V was used for collecting the fluorescence data and the emission spectrum was collected from 555 to 600 nm wavelength range. The ligand solution in PBS buffer was added to the target RNA in the cell in either 2 or 4 µL increments and was allowed to equilibrate for 10 minutes before recording the emission spectrum. Statistical analysis of the data was carried out using Origin 7 (OriginLab corporation). Binding constants were determined by fitting the data to one-site binding model equation.

Figure 12:
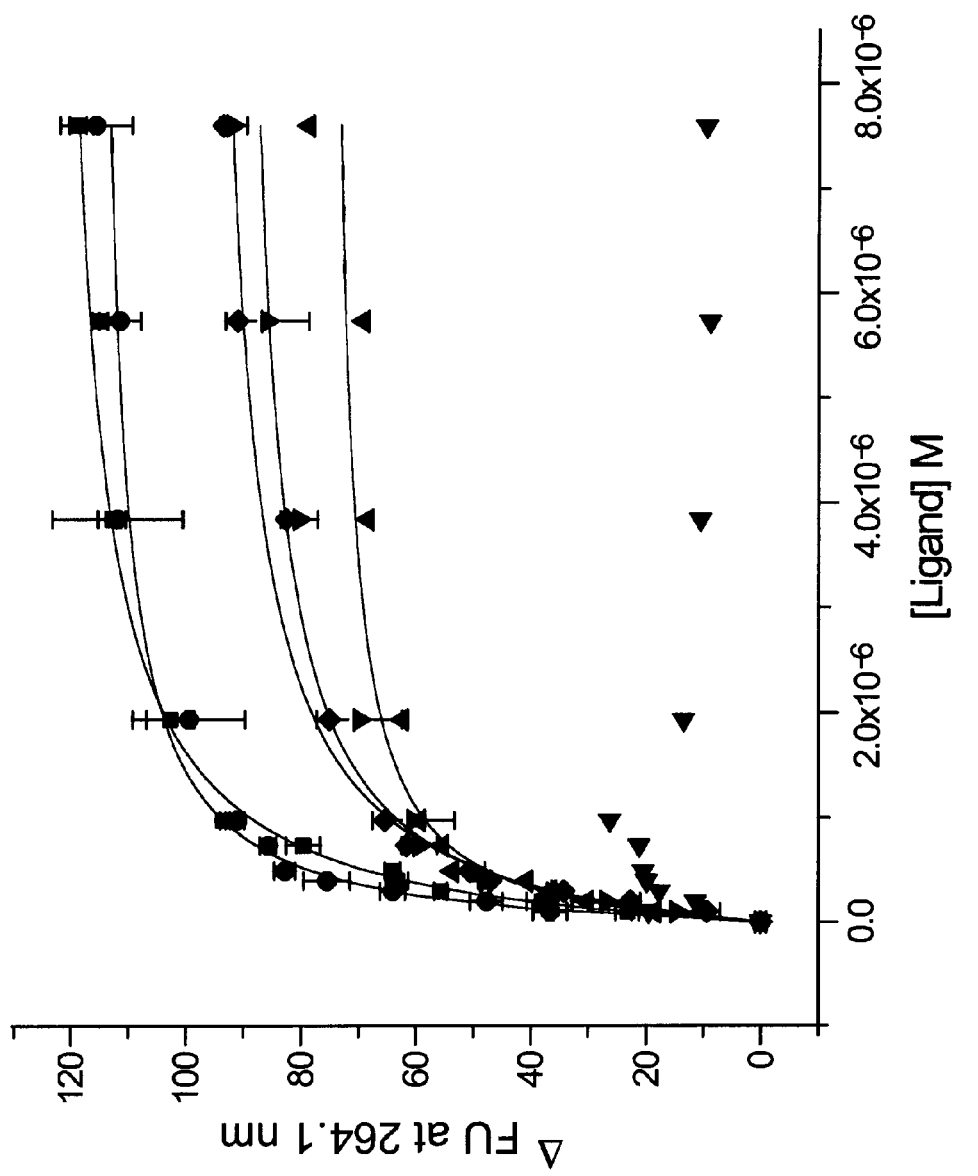
FIG. 12 is a graph showing binding isotherm obtained by plotting change in dilution corrected fluorescence of Cy-3 labeled RNA as a function of the ligand concentration. (■ [5-5 E]; ● [5-5 Z]; ▲ [5-5 E] in presence of excess of yeast tRNA; ▼ [5-5 Z] in presence of excess of yeast tRNA; ♦ [5]; ◄ [5] in presence of excess tRNA.)

A 5'-Cy3 labeled upper stem-loop of HIV-1 RNA (SEQ ID NO:1) was titrated with increasing amount of the dicarba analogs in a phosphate buffer (PBS, pH 7.4) using the same protocol to that described in Example 3 above. The fluorescence intensity of the labeled RNA stem-loop decreased as a function of the ligand concentration. As shown in FIG. 12, both 5-5 E and 5-5 Z were found to bind effectively to the RNA stem-loop with a binding affinity equivalent to ligand 1-1, indicating that isosteric replacement of the disulfide linkage in 1-1 with an olefin does not affect its binding affinity to the RNA stem-loop (see also Table 4 below). The Z-isomer (5-5 Z) was found to bind with slightly better affinity than the E-isomer (5-5 E). Normally, one would expect a greater difference between the affinities of the two isomers. The results here, which suggest otherwise, are justified by the fact that there is free rotation, and thus flexibility, across the C—C bond adjacent to the double bond.

TABLE 4

Binding Affinity of Dicarba Analogs to the HIV-1 Frameshift-Inducing Stem-loop ($4 \times 10^{-7}$ M)

| Ligand[a] | Binding Affinity ($K_d$) (µM) | Binding Affinity ($K_d$) in the presence of excess yeast tRNA[b] (µM) |
|---|---|---|
| 1-1 | 0.35 ± 0.11 | 0.32 ± 0.07 |
| 5 | 0.37 ± 0.02 | No binding |
| 5-5 E | 0.41 ± 0.02 | 0.45 ± 0.09 |
| 5-5 Z | 0.24 ± 0.05 | 0.29 |

[a]Ligand stock concentrations used in the titrations were 20, 50 and 200 µM
[b]Concentration of tRNA used was 8 µM (twenty-fold in excess of the stem-loop concentration) in comparison to 1-1 as measured by fluorescence titrations in PBS buffer at 25° C. The reported $K_d$ values are an average from two separate titration experiments.

To further evaluate the binding selectivity of dicarba analogs to the frameshift-inducing stem-loop, fluorescence titrations were repeated in the presence of twenty-fold excess concentration of yeast tRNA. The binding affinity of the dicarba analogs to the stem-loop was found to be retained (Table 4), suggesting that they exhibit selectivity for binding to the HIV-1 RNA stem-loop. In an interesting result it was discovered that the monomeric compound (5) also bound to the HIV-1 RNA stem-loop with similar affinity as that of the other analogs, but the binding affinity was diminished in the presence of tRNA. Thus, it suggests that the monomer 5 is non-specific in its binding to the HIV-1 RNA stem-loop. Quinoline is a known intercalator of nucleotide bases and has the capability to interact with RNA non-specifically. But it is the peptidic part of the molecule in ligands 5-5 E and 5-5 Z that imparts specificity to the interaction between the ligand and the RNA stem-loop. The peptidic part on monomer 5 is insufficient to impart specificity to the interaction as evident from the results.

In conclusion, biostable analogs of the high affinity and selectivity ligand for HIV-1 frameshift-inducing stem-loop RNA have been synthesized. The binding studies suggest that isosteric replacement of the disulfide bridge by an all carbon bridge did not affect the binding affinity of this ligand. Also, these dicarba analogs show high selectivity for the stem-loop as evident from the competitive binding studies in the presence of tRNA. The ligands 5-5 E and 5-5 Z, due to their high affinity and selectivity and less vulnerability to physiological conditions, are promising candidates for further biological evaluation in a cell-based system.

Example 7

Hydrogenation of Olefin Analogs 5-5 E and 5-5 Z

Hydrogenation of the double bond in dimers 5-5 E and 5-5 Z will be carried out using $H_2$ on Pt/C catalyst. The resulting dimer analog will be screened for its affinity in binding the HIV-1 mRNA stem-loop of SEQ ID NO:1 in the manner described in the preceding Examples.

Example 8

Alteration of Disulfide to Disulfoxide in Ligand

As noted in Example 5, the reducing environment of the cell may hinder the utility of possible therapeutic disulfide based compounds, such as 1-1 and 1-3. A second route for conversion of the disulfide linkage aims to further oxidize the disulfide to a disulfoxide, rendering it incapable of disulfide exchange.

The oxidation of 1-1 (FIG. 13, Scheme 2) to the disulfoxide was achieved by reacting 1-1 with $H_2O_2$ (1.1 eq.) and $MoClO_2$ (0.05 eq) in 1:1 acetonitrile:water for 15 minutes, followed by purification by RP-HPLC (Jeyakumar et al., "Selective Oxidation of Sulfides to Sulfoxides and Sulfones at Room Temperature Using $H_2O_2$ and Mo(VI) Salt as Catalyst," *Tetrahedron Letters* 47:4573-76 (2006), which is hereby incorporated by reference in its entirety). The compound degraded within a few hours of synthesis as evidenced by MS and HPLC. Interestingly, there are limited reports of similar disulfoxide derivatives (Dulude et al., "Decreasing the Frameshift Efficiency Translates into an Equivalent Reduction of the Replication of Human Immunodeficiency Virus Type 1," *Virology* 345:127-136 (2006), which is hereby incorporated by reference in its entirety). However, a fluorescence titration was performed with freshly prepared 1-1 disulfoxide and the HIV1 frameshift inducing stemloop, resulting in a similar $K_D$ of 0.41 µM.

Example 9

Characterization of the Effect of 1-1, 5-5 E, and 5-5 Z on the HIV-1 Frameshifting Process Compounds 1-1, 5-5 E, and 5-5 Z will be modified via incorporation of a oligo-D-Arg permeability enhancing sequence according to previously described procedures (Wender et al., "The Design, Synthesis, and Evaluation of Molecules that Enable or Enhance Cellular Uptake: Peptoid Molecular Transporters," *Proc Natl Acad Sci U.S.A.* 97:13003-13008 (2000); Brunner et al., "Targeting DNA Mismatches with Rhodium Intercalators Functionalized with a Cell-penetrating Peptide," *Biochemistry* 45:12295-12302 (2006), each of which is hereby incorporated by reference in its entirety).

As an alternative to the oligoarginine-conjugated compounds described above, compounds incorporating a reducible form of the oligoarginine transporter are also envisioned as prodrugs. Such conjugates have proven useful elsewhere; for example, Jones et al. have demonstrated that incorporation of a disulfide linkage into an octaarginine—luciferin conjugate allows delivery and release of luciferin into a prostate cancer cell line (Jones et al., "Releasable Luciferin-transporter Conjugates: Tools for the Real-time Analysis of Cellular Uptake and Release," *J. Am. Chem. Soc.* 128:6256-6257 (2006), which is hereby incorporated by reference in its entirety) and into luciferase transgenic mice (Wender et al., "Real-time Analysis of Uptake and Bioactivatable Cleavage of Luciferin-transporter Conjugates in Transgenic Reporter Mice," *Proc. Natl. Acad. Sci. USA* 104:10340-10345 (2007), which is hereby incorporated by reference in its entirety). Similarly, Rothbard et al. successfully achieved transdermal delivery and release of cyclosporin A conjugated to a heptaarginine transporter via a pH-sensitive linker (Rothbard et al., "Conjugation of Arginine Oligomers to Cyclosporine A Facilitates Topical Delivery and Inhibition of Inflammation," *Nature Med.* 6:1253-1257 (2000), which is hereby incorporated by reference in its entirety).

Figure 14:
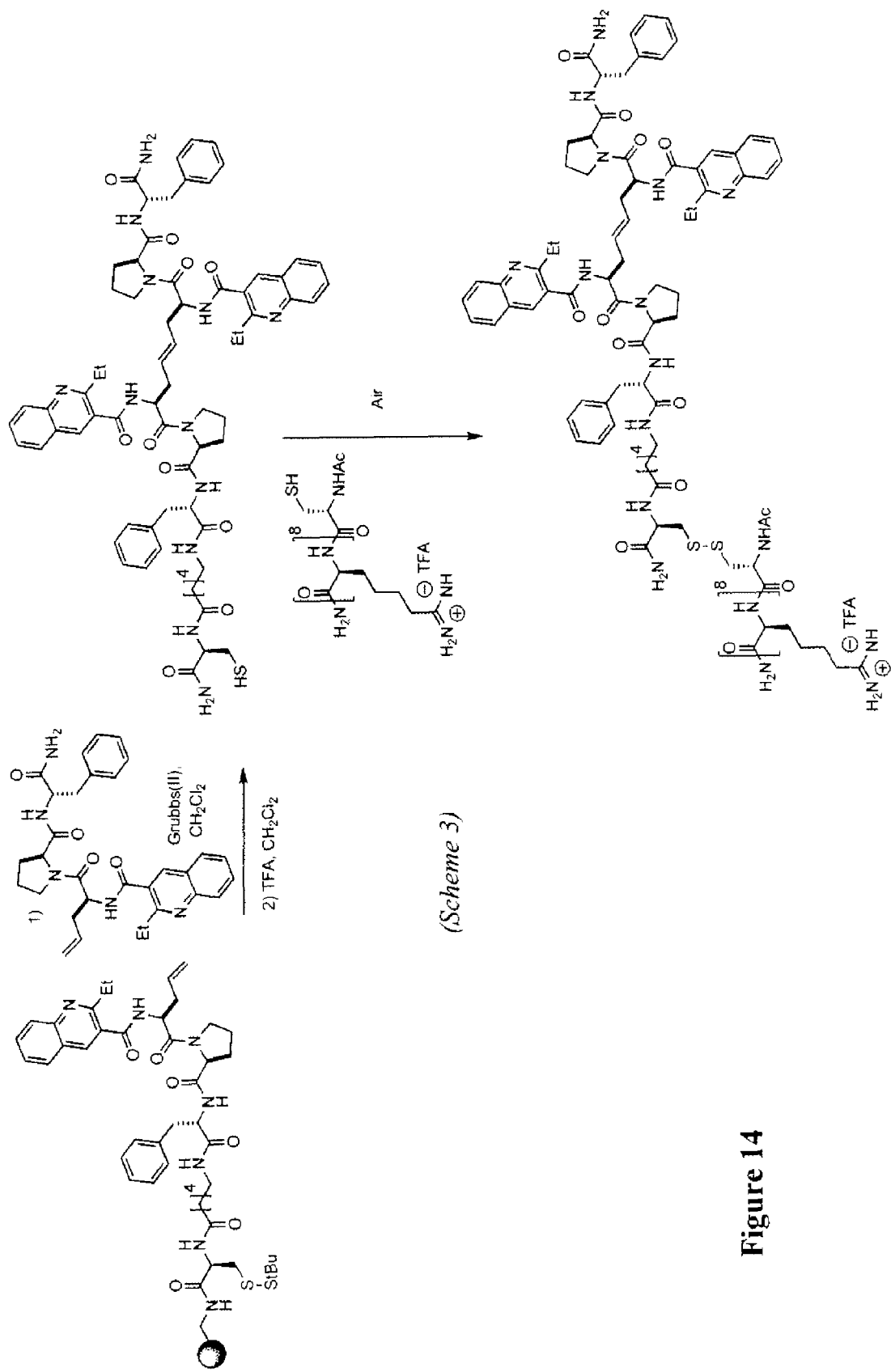
FIG. 14 illustrates Scheme 3 for the formation of oligoarginine prodrug analogs of the dimers.

The synthesis will be accomplished as shown in FIG. 14 (Scheme 3). Air or DMSO-mediated oxidative disulfide formation of the heterodimer will naturally lead to the production of homodimeric disulfides as well. However, it has been have observed that this straightforward (statistical) approach to disulfide formation followed by HPLC purification is the most efficient method of obtaining the desired compound, despite its lack of synthetic selectivity. The resulting compounds should be suitable for cellular uptake, where they may interact directly with the HIV-1 RNA stem-loop and be analyzed for their effects on frameshifting.

Analysis will involve a dual luciferase reporter assay. Compounds will be administered to Hek Dual-luc-(−1)FS (clone 2.1) cells in a DMSO vehicle (0.5% total) for 24 hours (Dulude et al., "Decreasing the Frameshift Efficiency Translates into an Equivalent Reduction of the Replication of Human Immunodeficiency Virus Type 1," *Virology* 345:127-136 (2006), which is hereby incorporated by reference in its entirety). Luciferase will be read and plotted as a function of small molecule concentration. A positive control and DMSO vehicle control will also be analyzed.

Example 10

Identification of Selective Ligands for (CUG) Repeat RNA from the 11,325 Member Resin Bound Dynamic Combinatorial Library Given the success in screening the RBDCL against the HIV-1 slippery frameshift stem/loop, it was reasoned that screening the RBDCL against a (CUG) repeat RNA may afford novel lead compounds for DM1, while constituting an effective test of the ability of the RNA-targeted RBDCL to yield a different ligand when screened against a different sequence from that originally targeted.

RBDCL screening was performed as previously described in the preceding Examples, i.e., in PBS pH 7.2+1 mM $MgCl_2$ at 22° C. for 72 hours. Screening was performed with 1 µM Cy3-CUGCUGCUGCUGCUGCUGCUGCUGCUGCUG (hereinafter Cy3-$(CUG)_{10}$) (SEQ ID NO:6). Electrophoretic RNA analysis confirmed that no RNA degradation occurred during the experiment. Post-screen fluorescence microscopy identified 4 beads exhibiting significant fluorescence. These four beads, representing components critical to high affinity ligands, were removed via syringe, washed, and compounds were photolytically cleaved from the resin (50 μl 4:1 MeOH: H₂O, 365 nm, 24 hrs). Mass spectrometry identified unreacted thiol-S-tBu monomers (which as the highest population species on the resin were most easily detected) corresponding to library monomers 6-9.

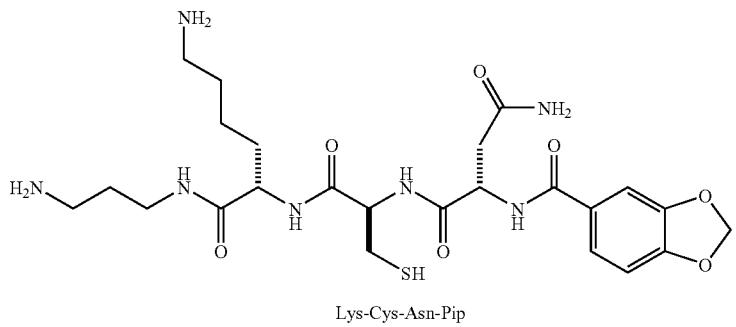

Lys-Cys-Asn-Pip

6

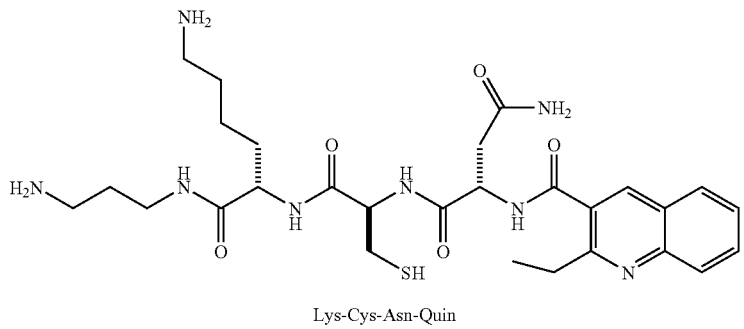

Lys-Cys-Asn-Quin

7

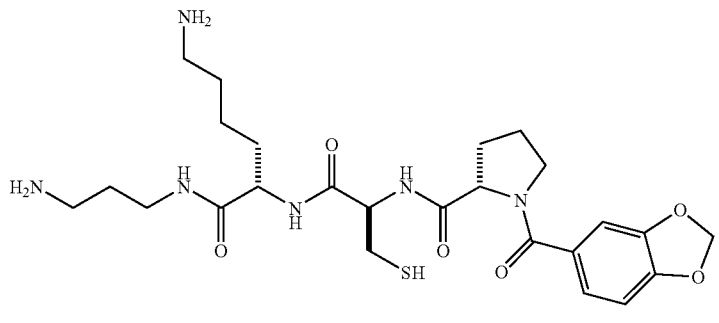

Lys-Cys-Pro-Pip

8

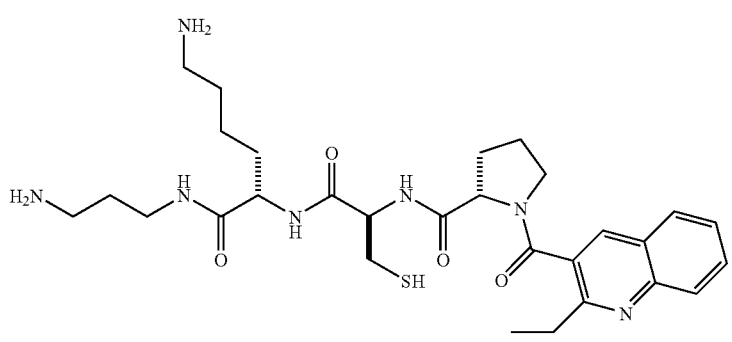

Lys-Cys-Pro-Quin

9

The four selected components had a high degree of sequence similarity: Lys-Cys-(Asn/Pro)-(Quin/Pip). Importantly, these differ from the components obtained from screening this library against the HIV-1 frameshift stimulating RNA stemloop ((Phe-Pro-Cys-Quin)$_2$ or dimer 1-1) as identified in Example 3.

The identities of monomers 6-9 allow for 10 unique possible homo- and heterodisulfides. In previous work, a secondary resin-bound screen of the possible combinations of selected monomers was employed to identify the highest affinity leads. However, in this case, an analogous screen showed no clear differences among the 10 possibilities, suggesting that all 10 could have similar affinities for CUG repeat RNA, such as SEQ ID NO:6.

Example 11

Synthesis of CUG-Repeat Binding Dimers

Selected DCL monomers 6-9 were synthesized on solid phase using standard FMOC main chain and Boc/Trt side chain protecting chemistry. Briefly, each monomer was synthesized on Wang resin (100-200 mesh size, 1 mmol/g loading, 500 mg, 0.5 mmole). First the resin was activated through the addition of 1-1'-carbonyl-di-imidazole (1620 mg, 5 mmol, 10 eq) in 12 mL of DMF. This suspension was rotated on a LabQuake™ rotator for 12 hours. The vessel was then evacuated and washed three times with 15 mL DCM. Propane diamine (421 µL, 5 mmol, 10 eq) was added in 12 mL of DMF and rotated for an additional 12 hours. The resin was then washed 6× with DCM and 6× with DMF. FMOC-Lys(Boc)-OH (702.5 mg, 1.5 mmol, 3 eq), HBTU (570 mg, 1.5 mmol, 3 eq), and DIPEA (424 µL, 2.5 mmol, 5 eq) in 10 ml DMF, was added to each batch of resin, rotated for 1 hour, and the resin was washed. Then FMOC was removed (20% piperidine/DMF, 30 mins.) and resin was washed. FMOC-Cys(Trt)-OH (878 mg, 1.5 mmol, 3 eq), HBTU (570 mg, 1.5 mmol, 3 eq), and DIPEA (424 µL, 2.5 mmol, 5 eq) in 10 mL DMF was added to each batch of resin, rotated for 1 hour, and the resin was washed. FMOC was removed with (20% piperidine/DMF, 30 mins.) and resin was washed. Then either FMOC-Asn(Trt)-OH (895 mg, 1.5 mmol, 3 eq) for compounds 6 and 7 or FMOC-Pro-OH (506 mg, 1.5 mmol, 3 eq) for compounds 8 and 9 HBTU (570 mg, 1.5 mmol, 3 eq), and DIPEA (424 µL, 2.5 mmol, 5 eq) in 10 mL DMF was added, rotated for 1 hour, and the resin was washed. FMOC was removed with (20% piperidine/DMF, 30 mins.) and resin was washed. Finally, piperonylic acid (250 mg, 1.5 mmol, 3 eq) for compounds 6 and 8 or 3-carboxy-2-ethyl-3-quinolinium chloride (353 mg, 1.5 mmol, 3 eq) of compounds 7 and 9, HBTU (570 mg, 1.5 mmol, 3 eq), and DIPEA (424 µL, 2.5 mmol, 5 eq) in 10 mL DMF was added and rotated for 1 hour and the resin was washed. Final products were cleaved from the resin and Boc/Trt groups were removed by treatment with 10 mL of a 1% TES/50% TFA solution in DCM for 2 hours. Products were purified by precipitation in chilled ether (−20° C.). Solids were concentrated by centrifugation (2500 rpm, 10 min), the solution was removed, and fresh ether was added. The solution was mixed by vortex and solids were again concentrated by centrifugation. This series was repeated five times. After the last washing step the solids were dried by lyophilization, resulting in off white powders.

Dynamic combinatorially selected disulfides 6-6, 6-7, 6-8, 6-9, 7-7, 7-8, 7-9, 8-8, 8-9, and 9-9 were prepared by mixing equimolar amounts of 6, 7, 8, or 9 with 6, 7, 8, or 9 in water for a period of 7 days. Disulfide formation was monitored by HPLC. When disulfide formation had reached completion, the resulting desired disulfides were separated and purified by RP-HPLC using a 0.1% TFA acetonitrile:water gradient, and purified disulfides were dried.

Example 12

Screening of Dimers for CUG-Repeat Binding Affinity

A filter binding assay system was utilized to provide a rapid initial assessment of binding affinity. All binding studies were performed in PBS pH 7.2+1 mM MgCl$_2$ at 22° C. Various concentrations of small molecules were incubated with 10 nM FAM-labeled RNA in a total volume of 50 µl for 20 minutes. A slot blot apparatus was then assembled with a wet nitrocellulose filter, on top of a wet nylon filter, on top of filter paper. 40 µl of each binding mixture was then loaded into an individual well of the apparatus and allowed to penetrate the filters for 10 minutes. The peptidic disulfides selected from the DCL efficiently bind to the nitrocellulose filter. In contrast, the FAM-labeled RNA strands penetrate the nitrocellulose filter and are bound by the nylon filter. As such, RNA bound by the peptidic library members remains bound on the nitrocellulose filter, and unbound RNA passes to the nylon filter.

The RNA molecules used in this procedure included, in addition to the HIV-1 frameshift stem-loop (SEQ ID NO:1 as control), the following FAM-U labeled molecules (CUG repeats shown in bold):

```
                                           SEQ ID NO: 7
CCGCUGCUGCUGCUGCUGCUGCUGCUGCUGCUGCGG

SEQ ID NO: 8
GGGCUGCUGCUGCUGCUGCUGCUGCUGCUGCUGCUGCUGC

UGCUGCUGCUGCUGCUGCUGCUGCUGCUGCUGCUGCUGCU

GCUGCUGCUGCUGCUGCUGCUGCUGCUGCUGCUGCUGCUG

CUGCUGCUGCUGCUGCUGCUGCUGCUGCUGCUGCUGCUGC

UGCUGCUGCUGCUGCUGCUGCUGCUGCUGCUGCUGCUGCU

GCUGCUGCUGCUGCUGCUGCUGCUGCUGCUGCUGCUGCUG

CUGCUGCUGCUGCUGCUGCUGCUGCUGCUGCUGCUGCUGC

UGCUGCUGGGG

SEQ ID NO: 9
CCGCUGCUGCUGGGCAACCUGCUGCUGCGG

SEQ ID NO: 10
CCAGCUGGCAACCAGCUGG

SEQ ID NO: 11
CGCGCUGCUGCGCG
```

SEQ ID NOS: 1, 7, 9, 10, and 11 were purchased from IDTDNA (Coralville, Iowa) with RP-HPLC purification. SEQ ID NO:8 was prepared by in vitro transcription as previously described (Yuan et al., "Muscleblind-like 1 interacts with RNA hairpins in splicing target and pathogenic RNAs," Nucl Acids Res. 35(16):5474-86 (2007), which is hereby incorporated by reference in its entirety. All CUG RNA variants were prepared in 1×PBS+1 mM MgCl$_2$ and renatured by heating to 80° C. for 2 minutes followed by slow cooling to room temperature. Total yeast tRNA was purchased (Fluka, 83853, ~20 A260/mg) and prepared in 1×PBS+1 mM MgCl2 and renatured by heating to 80° C. for 2 minutes followed by slow cooling to room temperature.

Figure 15A:
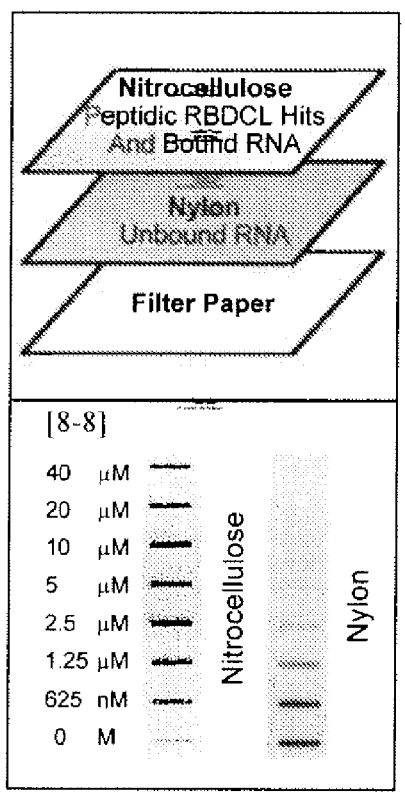
FIGS. 15A-B illustrate the results of RNA filter binding assays.
Figure 15B:
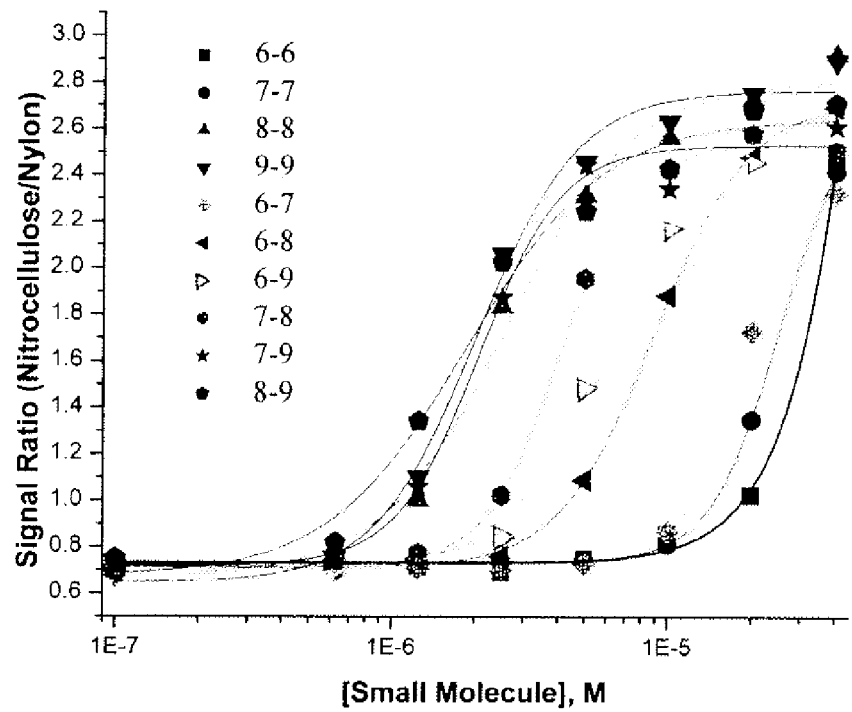

Densitometric analysis of the ratio of labeled RNA on the nitrocellulose to nylon filters allows quantification of binding (FIG. 15A). All binding isotherms were fit to the logistic binding model (Equation 1 above). The repetitive nature of the target sequences may in some cases result in binding stoichiometries that are more complex than a simple 1:1 interaction. However, as all measurements were performed at [RNA]<<$K_D$, this does not affect the validity of the reported $K_D$ values. As seen in FIG. 15B, the 10 possible disulfides identified in the screen all show affinity for $(CUG)_{109}$ RNA (SEQ ID NO:8) (Table 5). Compounds 8-8, 9-9, 7-9, and 8-9 exhibit the highest affinity (~2 µM) and, as such, were chosen as a focus for further study.

TABLE 5

$K_D$ Values for Selected Ligands 8-8, 9-9, 7-9, and 8-9

```
        G-C
       U   U
        C-G
       [G-C
        U   U
        C-G ]
           G-C  4
        C-G
        C-G
   FAM-5 õ   3 õ
```
SEQ ID NO: 7

```
        G-C
       U   U
  FAM   C-G
       [G-C
        U   U
        C-G ]53
           G-C
           G  U
           G   G
    5 õ       G
                G 3 õ
```
SEQ ID NO: 8

```
         CA
        G   A
        G-C
       [G-C
        U   U
        C-G ]3
           G-C
        C-G
        C-G
   FAM-5 õ   3 õ
```
SEQ ID NO: 9

```
         CA
        G   A
        G-C
        U-A
        C-G
        G-C
        A-U
        C-G
        C-G
   FAM-5 õ   3 õ
```
SEQ ID NO: 10

```
        G-C
       U   U
        C-G
        G-C
        C-G
        G-C
        C-G
   FAM-5 õ   3 õ
```
SEQ ID NO: 11

```
         CA
        A   A
        C-G
        C-G
        C-G
        U-A
        U-A
        C-G
        C-G
        G-C
        G-C
   FAM-5 õ   3 õ
```
SEQ ID NO: 1

TABLE 5-continued

| Method | SEQ ID NO: | 8-8 $K_D$ (µM ± SD) | 9-9 $K_D$ (µM ± SD) | 7-9 $K_D$ (µM ± SD) | 8-9 $K_D$ (µM ± SD) |
|---|---|---|---|---|---|
| FBA | 7 | 5.4 ± 0.6 | 6.7 ± 0.2 | 4.5 ± 0.6 | 4.1 ± 0.2 |
| FBA | 7 + 20 x tRNA | 14 ± 04 | 18 ± 2.1 | 10 ± 0.7 | 9.6 ± 0.7 |
| FT | 7 | 1.4 | 2.2 | 2.1 | 2.1 |
| FT | 7 + 20 x tRNA | 2.4 | 3.4 | 2.9 | 4.2 |
| FBA | 8 | 2.5 | 2.1 | 2.1 | 1.9 |
| FBA | 9 | 9.3 ± 0.4 | 7.1 ± 1.1 | 6.4 ± 1.0 | 4.7 ± 0.1 |
| FT | 9 | 2.1 | 1.7 | 1.6 | 2.6 |
| FBA | 10 | 21 ± 1.4 | >40 | 19.5 ± 1 | 21 ± 1.8 |
| FT | 10 | NC | 17 | NC | NC |
| FBA | 11 | 7.5 ± 0.9 | 8.5 ± 0.1 | 4.6 ± 0.1 | 6.0 ± 0.1 |
| FT | 11 | NC | NS | NC | NC |
| FBA | 1 | 41 ± 9 | 24 ± 5 | 22 ± 2 | 16 ± 4 |

Method as determined by filter binding assay (FBA) or fluorescence titration (FT).
FBA were performed in triplicate.
NC = Not Calculable.
NS = Not Saturatable.

To test specificity and to confirm the determined binding affinities, filter binding assays and fluorescence titrations were performed with SEQ ID NOS: 7-11 (Table 5), and the HIV-1 frameshift stimulating RNA hairpin used in preceding Examples (SEQ ID NO:1, Table 5). Fluorescence titrations were performed using a Varian Cary Eclipse spectrophotometer. 2 µl of 50 or 500 µM small molecule were titrated into 400 µl of FAM labeled RNA sequences an allowed to equilibrate for at least 10 minutes, or until no change in fluorescence spectra was observed. Changes in fluorescence emission at 518 nm (excitation at 490 nm) were measured. Raw data were corrected for dilution dependant changes, and $Em_{518}$ was plotted against small molecule concentration and fit to the one site binding equation $y=(b_{max}*x)/(K_D+x)$.) Competition experiments utilizing target RNA (SEQ ID NO:7) and a 20-fold molar excess of total yeast tRNA were performed to measure non-specific RNA binding (Luedtke et al., "RNA-Ligand Interactions: Affinity and Specificity of Aminoglycoside Dimers and Acridine Conjugates to the HIV-1 Rev Response Element," *Biochemistry* 42:11391-11403 (2003), which is hereby incorporated by reference in its entirety). Compound 1-1, the HIV-1 RNA ligand, served as a negative control.

As seen in Table 5, there is good general agreement between the measured dissociation constants from filter binding and fluorescence analysis. 8-8, 9-9, 7-9, and 8-9 all bind with similar affinity to target (CUG) repeat RNA (SEQ ID NOS: 7-9). Competition assays utilizing 20 fold molar (~40-fold base) excess of total yeast tRNA result in only ~2 fold loss in affinity; combined with the >4 fold decrease in affinity to SEQ ID NO:1, these data suggest that the compounds show selectivity towards target (CUG) repeat RNA. Analysis with the variant (CUG) stem (SEQ ID NO:9) and (CUG) loop (SEQ ID NO:11) show that compounds bind (CUG) repeats with a preference for (CUG) repeats in hairpin stems. Analysis with the (CUG)/(CAG) complimentary RNA (SEQ ID NO:10) highlights the necessity of the U-U mismatch for efficient (CUG) repeat binding. As expected, compound 1-1 was found to have minimal affinity ($K_D$>40 µM) for CUG repeat RNA (SEQ ID NO:7).

Example 13

Screening of Dimers for Disruption of CUG-Repeat RNA/MBNL1 Protein Interaction

The ability of the selected ligands to disrupt the (CUG) repeat RNA-MBNL1 protein interaction, a cause of DM1, was next tested.

Figure 16:
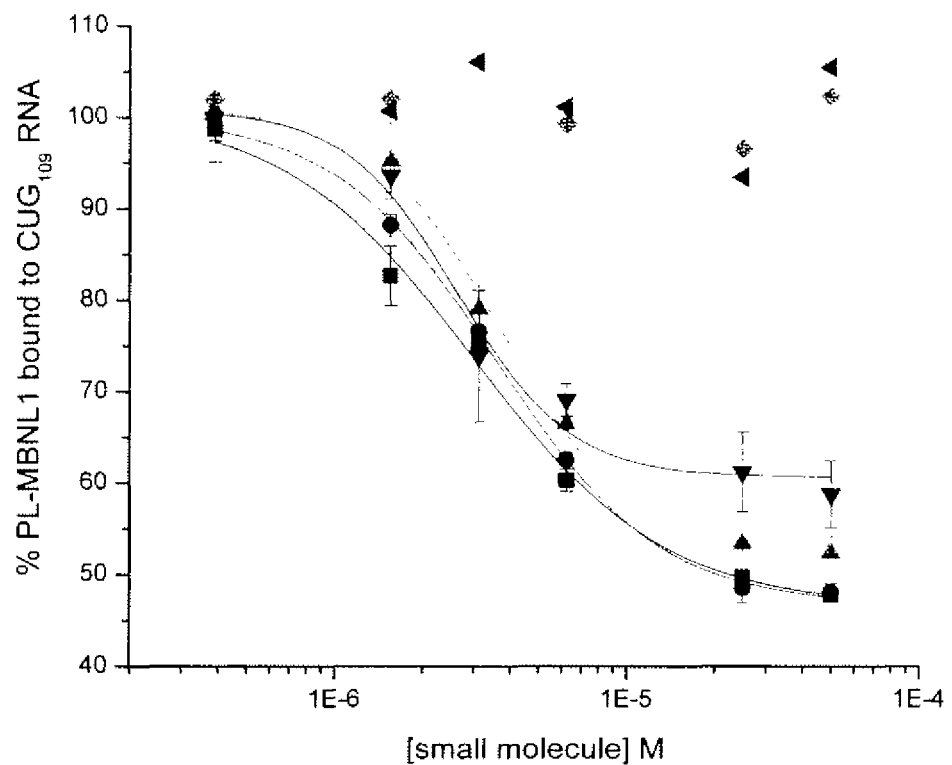
FIG. 16 shows dimer inhibition of the CUG$_{109}$ RNA (SEQ ID NO:8)-MBNL1 protein interaction. Reported K$_i$ are an average of ≥3 independent titrations±SD. ND=Not Determined.

Small molecule-mediated inhibition of $(CUG)_{109}$-MBNL1 binding was determined using an Enzyme Fragmentation Complementation (EFC) assay (Eglen et al., "β-Galactosidase Enzyme Fragment Complementation as A Novel Technology for High Throughput Screening," *Comb. Chem. High Throughput Screening* 6:381-387 (2003), which is hereby incorporated by reference in its entirety). Briefly, this was performed by first immobilizing $(CUG)_{109}$ RNA (SEQ ID NO:8) to a 96 well plate. Next, the immobilized RNA was incubated with recombinant MBNL1 fused to the PL enzyme donor peptide (PL-MBNL1, where "PL" is the commercial "ProLabel" enzyme donor peptide) (DiscoveRx PathHunter ProLabel Detection kit) in the presence of varying concentrations of small molecule inhibitor. The Enzyme Acceptor (EA-β-galactosidase) complement was then added, and the activity of the resulting plate—$(CUG)_{109}$ bound (PL-MBNL1)-(EA-β-galactosidase) activity was monitored via a chemiluminsecent substrate. Only the EA-β-Gal bound to the PL-MBNL1 is capable of performing the luminescent reaction and, as such, any luminescence correlates to the amount of MBNL1 bound to the $(CUG)_{109}$ immobilized on the plate. Wells lacking $(CUG)_{109}$ RNA served as a background measure of non-specific luminescence and were subtracted from each experiment to yield a 0% bound value. Wells containing no small molecule inhibitor added served as 100% bound. Percent bound PL-MBNL1 vs. small molecule concentration were plotted, and data were fit to the logistic equation (Equation 1) to allow extraction of $K_i$ values (FIG. 16).

All of the CUG-selected compounds inhibit the $(CUG)_n$ MBNL1 interaction with $K_i$ values in the same range as their measured dissociation constants ($K_D$). Importantly, the selected compounds are able to inhibit the $(CUG)_n$ MBNL1 interaction in the presence of ~40-fold base excess of yeast tRNA with only ~2-3 fold loss in Compounds 6-6 and 1-1 do not show any inhibitory effect, as expected based on their lack of affinity for $(CUG)_n$ RNA. A maximum 50% total saturable inhibition was observed, which can be explained by the ability of MBNL1 to bind short sequences of (CUG) RNA, and the possibility that the small molecules do not bind and mask all possible MBNL1 binding sites in the $(CUG)_{109}$ hairpin. It is important to note that small changes in levels of splicing factors, such as MBNL1 sequestration by (CUG) RNA, have large effects on splicing (Black et al., "Mechanisms of Alternative Pre-messenger RNA Splicing," *Annu. Rev. Biochem.* 72:291-336 (2003), which is hereby incorporated by reference in its entirety), and thus even modest inhibition of the MBNL1-(CUG) RNA interaction may be therapeutically useful.

In summary, screening an RBDCL with a theoretical diversity of 11,325 members provided a series of ligands with good affinity and selectivity for $(CUG)_n$ repeat RNA, a causative agent of DM1. Importantly, the selected ligands were able to inhibit the (CUG) repeat RNA-MBNL1 protein interaction in vitro with low μM $K_i$ values, consistent with measured $K_D$ values. These compounds provide an excellent platform for ongoing SAR studies aimed at increasing affinity and specificity for (CUG) repeat RNA, as well as efforts to generate compounds suitable for in vivo studies. Finally, these results confirm the power of the RBDCC method in general, and specifically as a strategy for the rapid generation of sequence-selective RNA binding compounds.

Example 14

Oligomerization of CUG-Repeat Binding Monomers

One promising approach to increase the affinity and inhibitory effect of the compounds toward $(CUG)_n$ ligands is to form oligomeric structures of the selected ligands. The repetitive structure of $CUG)_n$ RNA is an excellent target for optimally spaced repetitive ligands.

Figure 17:
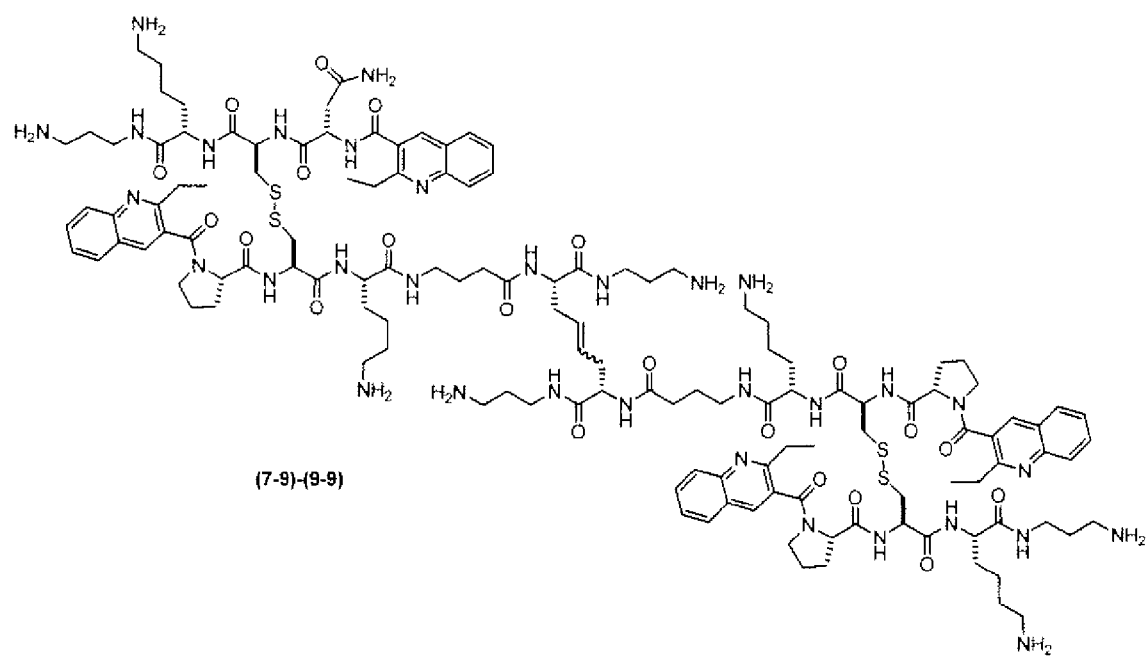
FIG. 17 is an illustration of an oligomerization of (CUG)$_n$ ligands 7-9 and 9-9.

Structural information would greatly aid in designing optimally spaced oligomeric (CUG)n ligands. In the absence of this structural information, a good starting point would be to design dimers or trimers of the disulfide ligands 8-8, 9-9, 7-9, and 8-9, incorporating various linkage lengths and compositions. As shown in FIG. 17, these oligomers can be formed using, e.g., a diamine linker or aminoalkanoic acid linker of various lengths. These oligomers can be screened for their affinity, selectivity, and inhibition as described in the preceding examples. Additionally, higher order oligomers could be designed based on similar principles.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A homo- or hetero-dimer compound of two monomers having a structure $$Q-(CH_2)_n-\overset{H}{N}-Z-A \quad (I)$$

wherein, for each monomer (I)

Q is NH$_2$;

n is independently an integer from 0 to about 5;

Z is independently a tripeptide or tetrapeptide comprising Phe-Pro-allyl-Gly, Val-His-allyl-Gly, Lys-allyl-Gly-Pro, or Lys-allyl-Gly-Asn, where one of the amino acids is linked to an amino acid in the other monomer by an olefin bond; and A is selected from

[structures shown]

wherein R$_2$ and R$_3$ are independently selected from the group consisting of hydrogen, methyl, ethyl, propyl, amino, methylamine, ethylamine, dimethylamine, diethylamine, methoxy, ethoxy, propoxy, hydroxyl, cyano, and thiocyanate and A is connected to Z via a carbonyl linkage.

2. The dimer compound according to claim 1, wherein an olefin bond links together two monomers having a structure $$Q-(CH_2)_n-\overset{H}{N}-Phe-Pro-Xaa\text{-[2-ethylquinoline-3-carbonyl]} \quad (II)$$

wherein, for each monomer (II)

Q is NH$_2$;

n is independently an integer from 0 to about 5; and

Xaa is allyl-Gly.

3. The dimer compound according to claim 1, wherein an olefin bond links together a first monomer having a structure $$Q-(CH_2)_n-\overset{H}{N}-Phe-Pro-Xaa\text{-[2-ethylquinoline-3-carbonyl]} \quad (II)$$

and a second monomer having a structure $$Q-(CH_2)_n-\overset{H}{N}-Val-His-Xaa\text{-[2-ethylquinoline-3-carbonyl]} \quad (III)$$

wherein, for each of monomers (II) and (III),

Q is NH$_2$;

n is independently an integer from 0 to about 5; and

Xaa is allyl-Gly.

4. The dimer compound according to claim 1, wherein an olefin bond links together a first and a second monomer, wherein the first and second monomers independently have the structure $$Q-(CH_2)_n-\overset{H}{N}-Lys-Xaa_1-Xaa_2\text{-[benzodioxole-carbonyl]} \quad (V)$$

or $$Q-(CH_2)_n-\overset{H}{N}-Lys-Xaa_1-Xaa_2\text{-[2-ethylquinoline-3-carbonyl]} \quad (VI)$$

where, for each of monomers (V) and (VI),

Q is NH$_2$;

n is independently an integer from 0 to about 5;

Xaa$_1$ is allyl-Gly; and

Xaa$_2$ is Pro or Asn.

5. A method of inhibiting HIV-1 proliferation, said method comprising:
  providing a dimer compound according to claim 1; and
  contacting an HIV-1 mRNA that encodes Pol polyprotein with the dimer compound under conditions effective to alter normal expression of the Pol polyprotein and thereby inhibit HIV-1 proliferation.

6. A method of treating HIV-1 in a human patient, said method comprising:
  administering to a human patient a dimer compound according to claim 1 under conditions effective to alter normal expression of HIV-1 Pol polyprotein, thereby disrupting HIV-1 proliferation to treat the human patient for HIV-1.

7. A composition comprising a homo- or hetero-dimer compound according to claim 1 and a carrier.

8. The composition according to claim 7, wherein the carrier is a pharmaceutically-acceptable carrier.

9. The composition according to claim 8, wherein the carrier is selected from a polyethylene glycol conjugate, a liposome, oligoarginine, and a nanoparticle carrier.

10. A method of making a homo- or hetero-dimer compound, said method comprising:
  providing a first and second monomer having a structure

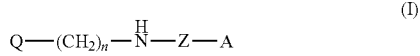
(I)

wherein:
  Q is NH$_2$;
  n is independently an integer from 0 to about 5;
  Z is independently a tripeptide or tetrapeptide comprising Phe-Pro-allyl-Gly, Val-His-allyl-Gly, Lys-allyl-Gly-Pro, or Lys-allyl-Gly-Asn; and
  A is selected from

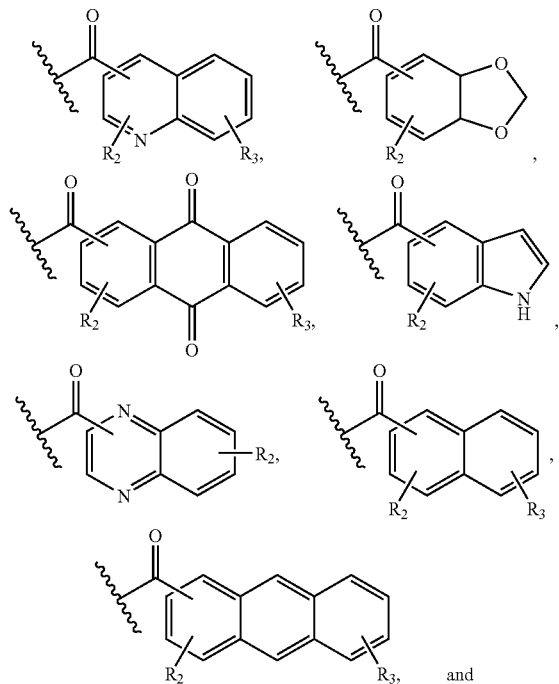

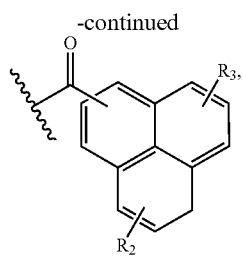

wherein R$_2$ and R$_3$ are independently selected from the group consisting of hydrogen, methyl, ethyl, propyl, amino, methylamine, ethylamine, dimethylamine, diethylamine, methoxy, ethoxy, propoxy, hydroxyl, cyano, and thiocyanate and A is connected to Z via a carbonyl linkage; and reacting the first and second monomers under conditions effective to form an olefin bond, thereby forming the homo- or hetero-dimer compound according to claim 1.

11. A method of altering the activity of a target RNA molecule comprising:
  contacting the RNA molecule with a dimer compound according to claim 1 that selectively binds to the target RNA molecule, said contacting being effective to alter activity of the RNA molecule.

12. The method according to claim 11 wherein the target RNA molecule is an RNA molecule of a pathogen, and the activity of the RNA molecule is critical to survival and/or proliferation of the pathogen.

13. The method according to claim 11 wherein the target RNA molecule is an RNA molecule of a mammal and comprises an expanded repeat sequence, and the activity of the RNA molecule is implicated in a disease state of the mammal.

14. The method according to claim 11 wherein the target RNA molecule contains a frameshift site or an expanded nucleotide repeat.

15. The method according to claim 11, wherein the frameshift site is −1 ribosomal frameshifting of SARS, HIV-1, Hepatitis C virus, Rous Sarcoma Virus, human T-Cell Leukemia Virus Type II, and Coronavirus.

16. A method of treating a subject for a disorder caused by an expanded RNA repeat sequence, said method comprising:
  administering to the subject a dimer compound according to claim 1 under conditions effective to alter function of an expanded RNA repeat sequence, thereby disrupting interaction between the RNA repeat sequence and splicing proteins to treat the subject for the disorder.

17. The method according to claim 16, wherein the expanded repeat sequence is selected from the group of (CUG)$_n$, (GAA)$_n$, (CAG)$_n$, (CGG)$_n$, (CCG)$_n$, (CCTG)$_n$, (ACAGGGGT(G/C))$_n$, (CCCCGCCCCGCG)$_n$, and (ATTCT)$_n$.

18. The method according to claim 16, wherein the disorder is selected from the group consisting of inherited neuropathy, muscular dystrophy, Friedreich ataxia, lysosomal storage disease, mitochondrial disorder, Huntington's disease, spinocerebellar ataxia (Machado-Joseph disease), dentatorubral pallidoluysian atrophy, spinobulbar muscular atrophy (Kennedy's disease), fragile X syndrome, Jacobsen syndrome, diabetes mellitus, and myoclonus epilepsy.

* * * * *

SEQUENCE LISTING

<160> NUMBER OF SEQ ID NOS: 13

<210> SEQ ID NO 1
<211> LENGTH: 22
<212> TYPE: RNA
<213> ORGANISM: Artificial
<220> FEATURE:
<223> OTHER INFORMATION: HIV-1 frameshifting stem-loop

<400> SEQUENCE: 1
ggccuuccca caagggaagg cc          22

<210> SEQ ID NO 2

```
<211> LENGTH: 22
<212> TYPE: DNA
<213> ORGANISM: Artificial
<220> FEATURE:
<223> OTHER INFORMATION: DNA sequence corresponding to SEQ ID NO: 1

<400> SEQUENCE: 2
ggccttccca caagggaagg cc                                              22

<210> SEQ ID NO 3
<211> LENGTH: 16
<212> TYPE: RNA
<213> ORGANISM: Artificial
<220> FEATURE:
<223> OTHER INFORMATION: control sequence with replaced stem and loop

<400> SEQUENCE: 3
uagucuucgu agacua                                                     16

<210> SEQ ID NO 4
<211> LENGTH: 22
<212> TYPE: RNA
<213> ORGANISM: Artificial
<220> FEATURE:
<223> OTHER INFORMATION: control sequence with replaced loop

<400> SEQUENCE: 4
ggccuucccc accgggaagg cc                                              22

<210> SEQ ID NO 5
<211> LENGTH: 52
<212> TYPE: RNA
<213> ORGANISM: Artificial
<220> FEATURE:
<223> OTHER INFORMATION: HIV-1 mRNA -1 ribosomal frameshift sequence

<400> SEQUENCE: 5
uuuuuuaggg aagaucuggc cuuccuacaa gggaaggcca gggaauuuuc uu             52

<210> SEQ ID NO 6
<211> LENGTH: 30
<212> TYPE: RNA
<213> ORGANISM: Artificial
<220> FEATURE:
<223> OTHER INFORMATION: CUG repeat decamer

<400> SEQUENCE: 6
cugcugcugc ugcugcugcu gcugcugcug                                      30

<210> SEQ ID NO 7
<211> LENGTH: 36
<212> TYPE: RNA
<213> ORGANISM: Artificial
<220> FEATURE:
<223> OTHER INFORMATION: CUG repeat decamer

<400> SEQUENCE: 7
ccgcugcugc ugcugcugcu gcugcugcug cugcgg                               36

<210> SEQ ID NO 8
<211> LENGTH: 333
<212> TYPE: RNA
<213> ORGANISM: Artificial
<220> FEATURE:
<223> OTHER INFORMATION: CUG repeat 109-mer

<400> SEQUENCE: 8
```

-continued

```
gggcugcugc ugcugcugcu gcugcugcug cugcugcugc ugcugcugcu gcugcugcug    60
cugcugcugc ugcugcugcu gcugcugcug cugcugcugc ugcugcugcu gcugcugcug   120
cugcugcugc ugcugcugcu gcugcugcug cugcugcugc ugcugcugcu gcugcugcug   180
cugcugcugc ugcugcugcu gcugcugcug cugcugcugc ugcugcugcu gcugcugcug   240
cugcugcugc ugcugcugcu gcugcugcug cugcugcugc ugcugcugcu gcugcugcug   300
cugcugcugc ugcugcugcu gcugcugcug ggg                                333
```

```
<210> SEQ ID NO 9
<211> LENGTH: 30
<212> TYPE: RNA
<213> ORGANISM: Artificial
<220> FEATURE:
<223> OTHER INFORMATION: CUG repeat trimer in stem only

<400> SEQUENCE: 9
ccgcugcugc ugggcaaccu gcugcugcgg                                     30
```

```
<210> SEQ ID NO 10
<211> LENGTH: 19
<212> TYPE: RNA
<213> ORGANISM: Artificial
<220> FEATURE:
<223> OTHER INFORMATION: CUG-CAG based-paired stem

<400> SEQUENCE: 10
ccagcuggca accagcugg                                                 19
```

```
<210> SEQ ID NO 11
<211> LENGTH: 14
<212> TYPE: RNA
<213> ORGANISM: Artificial
<220> FEATURE:
<223> OTHER INFORMATION: CUG loop sequence

<400> SEQUENCE: 11
cgcgcugcug cgcg                                                      14
```

```
<210> SEQ ID NO 12
<211> LENGTH: 9
<212> TYPE: DNA
<213> ORGANISM: Artificial
<220> FEATURE:
<223> OTHER INFORMATION: repeat sequence associated with diabetes
      mellitus
<220> FEATURE:
<221> NAME/KEY: misc_feature
<222> LOCATION: (9)..(9)
<223> OTHER INFORMATION: N at position 9 is G or C

<400> SEQUENCE: 12 acaggggtn                                                             9
```

```
<210> SEQ ID NO 13
<211> LENGTH: 12
<212> TYPE: DNA
<213> ORGANISM: Artificial
<220> FEATURE:
<223> OTHER INFORMATION: repeat sequence associated with myoclonus
      epilepsy

<400> SEQUENCE: 13
ccccgccccg cg                                                        12
```